(12) United States Patent
Bishop et al.

(10) Patent No.: US 10,925,731 B2
(45) Date of Patent: Feb. 23, 2021

(54) METHOD AND APPARATUS FOR TRANSVASCULAR IMPLANTATION OF NEO CHORDAE TENDINAE

(71) Applicant: Pipeline Medical Technologies, Inc., Wilmington, DE (US)

(72) Inventors: Gordon B. Bishop, Santa Rosa, CA (US); Randall T. Lashinski, Windsor, CA (US); Erik Griswold, Penngrove, CA (US)

(73) Assignee: Pipeline Medical Technologies, Inc., Wilmington, DE (US)

( * ) Notice: Subject to any disclaimer, the term of this patent is extended or adjusted under 35 U.S.C. 154(b) by 270 days.

(21) Appl. No.: 15/858,671

(22) Filed: Dec. 29, 2017

(65) Prior Publication Data

US 2018/0185153 A1    Jul. 5, 2018

Related U.S. Application Data

(63) Continuation-in-part of application No. 15/638,176, filed on Jun. 29, 2017, now Pat. No. 9,877,833.
(Continued)

(51) Int. Cl.
| | | |
|---|---|---|
| *A61F 2/24* | (2006.01) | |
| *A61B 17/04* | (2006.01) | |
| *A61B 17/00* | (2006.01) | |

(52) U.S. Cl.
CPC .......... *A61F 2/2457* (2013.01); *A61F 2/2466* (2013.01); *A61B 17/0401* (2013.01);
(Continued)

(58) Field of Classification Search
CPC ................. A61F 2/2457; A61F 2/2466; A61F 2220/0075; A61F 2220/0016;
(Continued)

(56) References Cited

U.S. PATENT DOCUMENTS

| | | |
|---|---|---|
| 5,329,923 A | 7/1994 | Lundquist |
| 5,456,708 A | 10/1995 | Doan et al. |

(Continued)

FOREIGN PATENT DOCUMENTS

| | | |
|---|---|---|
| CN | 101184454 | 10/2010 |
| CN | 103491901 | 1/2014 |

(Continued)

OTHER PUBLICATIONS

International Search Report and Written Opinion issued in PCT/US2017/069046, dated Jun. 14, 2018, 10 pages.
(Continued)

*Primary Examiner* — Ashley L Fishback
(74) *Attorney, Agent, or Firm* — Knobbe, Martens Olson & Bear, LLP

(57) ABSTRACT

Methods and devices for transvascular prosthetic chordae tendinea implantation are disclosed. A catheter is advanced into the left atrium, through the mitral valve, and into the left ventricle. A ventricular anchor is deployed from the catheter and into a wall of the left ventricle, leaving a ventricular suture attached to the ventricular anchor and extending proximally through the catheter. A leaflet anchor is deployed to secure a mitral valve leaflet to a leaflet suture, with the leaflet suture extending proximally through the catheter. The leaflet suture is secured to the ventricular suture to limit a range of travel of the leaflet in the direction of the left atrium. Also disclosed is an assembled in situ mitral valve leaflet restraint, having a neo papillary muscle and a neo chordae tendinea.

42 Claims, 69 Drawing Sheets

Related U.S. Application Data

(60) Provisional application No. 62/441,031, filed on Dec. 30, 2016.

(52) U.S. Cl.
CPC ....... *A61B 17/0467* (2013.01); *A61B 17/0482* (2013.01); *A61B 2017/00243* (2013.01); *A61B 2017/00309* (2013.01); *A61B 2017/0406* (2013.01); *A61B 2017/0409* (2013.01); *A61B 2017/0417* (2013.01); *A61B 2017/0441* (2013.01); *A61B 2017/0443* (2013.01); *A61B 2017/0464* (2013.01); *A61B 2017/0496* (2013.01); *A61F 2210/0014* (2013.01); *A61F 2220/0016* (2013.01); *A61F 2250/0098* (2013.01)

(58) Field of Classification Search
CPC ......... A61F 2230/0091; A61B 17/0469; A61B 2017/0406; A61B 2017/0409; A61B 2017/0441; A61B 2017/0464
See application file for complete search history.

(56) References Cited

U.S. PATENT DOCUMENTS

| | | |
|---|---|---|
| 5,674,217 A | 10/1997 | Wahlstrom et al. |
| 6,269,819 B1 | 8/2001 | Oz et al. |
| 6,458,107 B1 | 10/2002 | Ockuly |
| 6,461,366 B1 | 10/2002 | Seguin |
| 6,626,930 B1 | 9/2003 | Allen et al. |
| 6,629,534 B1 | 10/2003 | St. Goar et al. |
| 6,743,239 B1 | 6/2004 | Kuehn et al. |
| 6,752,813 B2 | 6/2004 | Goldfarb et al. |
| 6,770,083 B2 | 8/2004 | Seguin |
| 6,840,246 B2 | 1/2005 | Downing |
| 6,978,176 B2 | 12/2005 | Lattouf |
| 7,048,754 B2 | 5/2006 | Martin et al. |
| 7,083,628 B2 | 8/2006 | Bachman |
| 7,191,545 B2 | 3/2007 | Yi |
| 7,226,467 B2 | 6/2007 | Lucatero et al. |
| 7,288,097 B2 | 10/2007 | Séguin |
| 7,464,712 B2 | 12/2008 | Oz et al. |
| 7,563,267 B2 | 7/2009 | Goldfarb et al. |
| 7,604,646 B2 | 10/2009 | Goldfarb et al. |
| 7,608,091 B2 | 10/2009 | Goldfarb et al. |
| 7,632,308 B2 | 12/2009 | Loulmet |
| 7,635,386 B1 | 12/2009 | Gammie |
| 7,637,903 B2 | 12/2009 | Lentz et al. |
| 7,655,015 B2 | 2/2010 | Goldfarb et al. |
| 7,666,204 B2 | 2/2010 | Thornton et al. |
| 7,682,369 B2 | 3/2010 | Seguin |
| 7,736,388 B2 | 6/2010 | Goldfarb et al. |
| 7,871,368 B2 | 1/2011 | Zollinger et al. |
| 7,871,433 B2 | 1/2011 | Lattouf |
| 7,887,552 B2 | 2/2011 | Bachman |
| 7,914,515 B2 | 3/2011 | Heideman et al. |
| 7,914,545 B2 | 3/2011 | Ek |
| 8,075,570 B2 | 12/2011 | Bolduc et al. |
| 8,100,923 B2 | 1/2012 | Paraschac et al. |
| 8,172,872 B2 | 5/2012 | Osypka |
| 8,241,304 B2 | 8/2012 | Bachman |
| 8,252,050 B2 | 8/2012 | Maisano et al. |
| 8,273,054 B2 | 9/2012 | St. Germain et al. |
| 8,303,622 B2 | 11/2012 | Alkhatib |
| 8,409,273 B2 | 4/2013 | Thornton et al. |
| 8,465,500 B2 | 6/2013 | Speziali |
| 8,475,472 B2 | 7/2013 | Bachman |
| 8,475,525 B2 | 7/2013 | Maisano et al. |
| 8,480,730 B2 | 7/2013 | Maurer et al. |
| 8,545,551 B2 | 10/2013 | Loulmet |
| 8,545,553 B2 | 10/2013 | Zipory et al. |
| 8,603,066 B2 | 12/2013 | Heidman et al. |
| 8,690,939 B2 | 4/2014 | Miller et al. |
| 8,718,794 B2 | 5/2014 | Helland |
| 8,778,016 B2 | 7/2014 | Janovsky et al. |
| 8,814,824 B2 | 8/2014 | Kauphusman et al. |
| 8,852,213 B2 | 10/2014 | Gammie et al. |
| 8,940,042 B2 | 1/2015 | Miller et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,594 B2 | 2/2015 | Maisano et al. |
| 8,961,596 B2 | 2/2015 | Maisano et al. |
| 9,011,520 B2 | 4/2015 | Miller et al. |
| 9,023,065 B2 | 5/2015 | Bolduc et al. |
| 9,050,187 B2 | 6/2015 | Sugimoto et al. |
| 9,131,939 B1 | 9/2015 | Call et al. |
| 9,180,007 B2 | 11/2015 | Reich et al. |
| 9,198,649 B2 | 12/2015 | Karapetlan et al. |
| 9,241,702 B2 | 1/2016 | Maisano et al. |
| 9,259,218 B2 | 2/2016 | Robinson |
| 9,277,994 B2 | 3/2016 | Miller et al. |
| 9,307,980 B2 | 4/2016 | Gilmore et al. |
| 9,314,242 B2 | 4/2016 | Bachman |
| 9,474,606 B2 | 10/2016 | Zipory et al. |
| 9,492,264 B2 | 11/2016 | Fifer et al. |
| 9,572,667 B2 | 2/2017 | Solem |
| 9,636,205 B2 | 5/2017 | Lee et al. |
| 9,636,224 B2 | 5/2017 | Zipory et al. |
| 9,668,860 B2 | 6/2017 | Kudlick et al. |
| 9,681,864 B1 | 6/2017 | Gammie et al. |
| 9,681,964 B2 | 6/2017 | MacKenzie |
| 9,693,865 B2 | 7/2017 | Gilmore et al. |
| 9,724,195 B2 | 8/2017 | Goodwin et al. |
| 9,750,493 B2 | 9/2017 | Robinson et al. |
| 9,788,948 B2 | 10/2017 | Gilmore et al. |
| 9,801,720 B2 | 10/2017 | Gilmore et al. |
| 9,814,454 B2 | 11/2017 | Sugimoto et al. |
| 9,877,833 B1 | 1/2018 | Bishop et al. |
| 9,907,547 B2 | 3/2018 | Gilmore et al. |
| 9,907,681 B2 | 3/2018 | Tobis et al. |
| 10,022,114 B2 | 7/2018 | Gilmore et al. |
| 10,039,643 B2 | 8/2018 | Gilmore et al. |
| 10,039,644 B2 | 8/2018 | Navia et al. |
| 10,052,095 B2 | 8/2018 | Gilmore et al. |
| 10,058,323 B2 | 8/2018 | Maisano |
| 10,076,327 B2 | 9/2018 | Ellis et al. |
| 10,076,658 B2 | 9/2018 | Hastings et al. |
| 10,130,791 B2 | 11/2018 | Heideman et al. |
| 10,159,571 B2 | 12/2018 | de Canniere |
| 10,206,673 B2 | 2/2019 | Maisano et al. |
| 10,231,727 B2 | 3/2019 | Sutherland et al. |
| 10,238,491 B2 | 3/2019 | Tobis |
| 10,285,686 B2 | 5/2019 | Gammie et al. |
| 10,543,090 B2 | 1/2020 | Griswold et al. |
| 10,548,733 B2 | 2/2020 | Purcell et al. |
| 10,595,994 B1 | 3/2020 | Christianson et al. |
| 10,617,523 B2 | 4/2020 | Purcell et al. |
| 10,624,743 B2 | 4/2020 | Keidar et al. |
| 10,660,753 B2 | 5/2020 | Pham et al. |
| 10,667,910 B2 | 6/2020 | Bishop et al. |
| 10,675,150 B2 | 6/2020 | Bishop et al. |
| 10,682,230 B2 | 6/2020 | Bishop et al. |
| 2003/0105519 A1 | 6/2003 | Fasol et al. |
| 2003/0120341 A1 | 6/2003 | Shennib et al. |
| 2004/0044365 A1 | 3/2004 | Bachman |
| 2004/0049207 A1 | 3/2004 | Goldfarb et al. |
| 2005/0177132 A1 | 8/2005 | Lentz et al. |
| 2005/0177180 A1 | 8/2005 | Kaganov et al. |
| 2005/0251210 A1* | 11/2005 | Westra ............... A61B 17/0401 606/232 |
| 2007/0118151 A1 | 5/2007 | Davidson |
| 2007/0123979 A1 | 5/2007 | Perier et al. |
| 2007/0219565 A1 | 9/2007 | Saadat |
| 2008/0177304 A1 | 7/2008 | Westra et al. |
| 2008/0195126 A1 | 8/2008 | Solem |
| 2008/0228165 A1 | 9/2008 | Spence et al. |
| 2008/0228223 A1 | 9/2008 | Alkhatib |
| 2008/0288061 A1 | 11/2008 | Maurer et al. |
| 2008/0294188 A1 | 11/2008 | Appling et al. |
| 2009/0043153 A1 | 2/2009 | Zollinger et al. |
| 2009/0069847 A1 | 3/2009 | Hashiba et al. |
| 2009/0088837 A1 | 4/2009 | Gillinov et al. |

(56) References Cited

U.S. PATENT DOCUMENTS

| | | |
|---|---|---|
| 2009/0287304 A1 | 11/2009 | Dahlgren et al. |
| 2009/0312790 A1 | 12/2009 | Forsberg et al. |
| 2010/0023118 A1 | 1/2010 | Medlock et al. |
| 2010/0161043 A1 | 6/2010 | Maisano et al. |
| 2010/0280604 A1 | 11/2010 | Zipory et al. |
| 2011/0011917 A1 | 1/2011 | Loulmet |
| 2011/0022083 A1 | 1/2011 | DiMatteo et al. |
| 2011/0040326 A1 | 2/2011 | Wei |
| 2011/0060407 A1 | 3/2011 | Ketai et al. |
| 2011/0301698 A1 | 12/2011 | Miller et al. |
| 2012/0065464 A1 | 3/2012 | Ellis et al. |
| 2012/0095505 A1 | 4/2012 | Shluzas |
| 2012/0116418 A1 | 5/2012 | Belson et al. |
| 2012/0172915 A1 | 7/2012 | Fifer et al. |
| 2013/0035757 A1 | 2/2013 | Zentgraf et al. |
| 2013/0046380 A1 | 2/2013 | Maisano et al. |
| 2013/0190741 A1 | 7/2013 | Moll et al. |
| 2013/0253639 A1 | 9/2013 | Alkhatib |
| 2014/0142687 A1 | 5/2014 | De Canniere et al. |
| 2014/0142689 A1 | 5/2014 | De Canniere et al. |
| 2014/0243877 A9 | 8/2014 | Lee et al. |
| 2014/0243963 A1 | 8/2014 | Sheps et al. |
| 2014/0350417 A1* | 11/2014 | Van Bladel ........... A61F 2/2487 600/486 |
| 2015/0032127 A1 | 1/2015 | Gammie et al. |
| 2015/0119979 A1 | 4/2015 | Maisano et al. |
| 2015/0182255 A1 | 7/2015 | Shivkumar |
| 2015/0230919 A1 | 8/2015 | Chau et al. |
| 2015/0250590 A1 | 9/2015 | Gries et al. |
| 2015/0313620 A1 | 11/2015 | Suri |
| 2015/0342737 A1 | 12/2015 | Biancucci et al. |
| 2015/0359632 A1 | 12/2015 | Navia et al. |
| 2016/0058557 A1 | 3/2016 | Reich et al. |
| 2016/0143737 A1 | 5/2016 | Zentgraf et al. |
| 2016/0174964 A1 | 6/2016 | Tobis |
| 2016/0192925 A1 | 7/2016 | Bachman |
| 2016/0228117 A1 | 8/2016 | Borden |
| 2016/0240941 A1 | 8/2016 | Stavrianoudakis |
| 2016/0256269 A1 | 9/2016 | Cahalane et al. |
| 2016/0262741 A1 | 9/2016 | Gilmore et al. |
| 2016/0310701 A1 | 10/2016 | Pai |
| 2016/0354082 A1 | 12/2016 | Oz et al. |
| 2016/0367367 A1 | 12/2016 | Maisano et al. |
| 2017/0042658 A1 | 2/2017 | Lee et al. |
| 2017/0043120 A1 | 2/2017 | Heideman et al. |
| 2017/0079797 A1 | 3/2017 | Maisano et al. |
| 2017/0086975 A1 | 3/2017 | Gilmore et al. |
| 2017/0119368 A1 | 5/2017 | Solem |
| 2017/0156719 A1 | 6/2017 | Tobis |
| 2017/0156861 A1 | 6/2017 | Longoria et al. |
| 2017/0202657 A1 | 7/2017 | Lee et al. |
| 2017/0202669 A1 | 7/2017 | Schaffner et al. |
| 2017/0252032 A1 | 9/2017 | Hiorth et al. |
| 2017/0258464 A1 | 9/2017 | Gammie et al. |
| 2017/0258588 A1 | 9/2017 | Zipory et al. |
| 2017/0258594 A1 | 9/2017 | Gilmore et al. |
| 2017/0273681 A1 | 9/2017 | Gilmore et al. |
| 2017/0304050 A1 | 10/2017 | Keidar et al. |
| 2017/0304051 A1 | 10/2017 | Tobis et al. |
| 2017/0340433 A1 | 11/2017 | Berra et al. |
| 2017/0340443 A1 | 11/2017 | Stearns et al. |
| 2018/0064535 A1 | 3/2018 | Gilmore et al. |
| 2018/0185150 A1 | 7/2018 | Bishop et al. |
| 2018/0185151 A1 | 7/2018 | Bishop et al. |
| 2018/0185152 A1 | 7/2018 | Bishop et al. |
| 2018/0185179 A1 | 7/2018 | Murphy et al. |
| 2018/0206992 A1 | 7/2018 | Brown |
| 2018/0221148 A1 | 8/2018 | Guidotti et al. |
| 2018/0249993 A1 | 9/2018 | Denti et al. |
| 2018/0289480 A1 | 10/2018 | D'ambra et al. |
| 2018/0303614 A1 | 10/2018 | Schaffner et al. |
| 2018/0311007 A1 | 11/2018 | Tyler, II et al. |
| 2018/0318079 A1 | 11/2018 | Patel et al. |
| 2018/0318083 A1 | 11/2018 | Bolling et al. |
| 2018/0344311 A1 | 12/2018 | Gilmore et al. |
| 2018/0353297 A1 | 12/2018 | Griffin |
| 2018/0360439 A1 | 12/2018 | Niland et al. |
| 2019/0000624 A1 | 1/2019 | Wilson et al. |
| 2019/0015205 A1 | 1/2019 | Rajagopal et al. |
| 2019/0069891 A1 | 3/2019 | Gilmore et al. |
| 2019/0083085 A1 | 3/2019 | Gilmore et al. |
| 2019/0105027 A1 | 4/2019 | Gilmore et al. |
| 2019/0117401 A1 | 4/2019 | Cortez, Jr. et al. |
| 2019/0151090 A1 | 5/2019 | Gross et al. |
| 2019/0175345 A1 | 6/2019 | Schaffner et al. |
| 2019/0175346 A1 | 6/2019 | Schaffner et al. |
| 2019/0183480 A1 | 6/2019 | Hiorth et al. |
| 2019/0183648 A1 | 6/2019 | Trapp et al. |
| 2019/0216599 A1 | 7/2019 | Alkhatib |
| 2019/0216601 A1 | 7/2019 | Purcell et al. |
| 2019/0240023 A1 | 8/2019 | Spence et al. |
| 2019/0314155 A1 | 10/2019 | Franklin et al. |
| 2019/0328526 A1 | 10/2019 | Purcell et al. |
| 2019/0328527 A1 | 10/2019 | Pham et al. |
| 2019/0328528 A1 | 10/2019 | Purcell et al. |
| 2019/0328529 A1 | 10/2019 | Griswold et al. |
| 2019/0328530 A1 | 10/2019 | McDaniel et al. |
| 2019/0365539 A1 | 12/2019 | Rabito et al. |
| 2019/0380699 A1 | 12/2019 | Bak-Boychuk et al. |

FOREIGN PATENT DOCUMENTS

| | | |
|---|---|---|
| CN | 103635160 | 3/2014 |
| CN | 103813757 | 5/2014 |
| EP | 1898802 A1 | 3/2008 |
| EP | 2979647 A1 | 2/2016 |
| WO | WO 2007/061834 | 5/2007 |
| WO | WO 2008/005747 | 1/2008 |
| WO | 2010128502 A1 | 11/2010 |
| WO | WO 2012/040865 | 4/2012 |
| WO | WO 2013/179295 | 12/2013 |
| WO | WO 2017/066888 | 4/2017 |
| WO | WO 2017/066889 | 4/2017 |
| WO | WO 2017/066890 | 4/2017 |
| WO | 2017117560 A1 | 7/2017 |
| WO | WO 2018/035378 | 2/2018 |
| WO | WO 2018/126188 | 7/2018 |
| WO | WO 2018/148324 | 8/2018 |
| WO | WO 2018/148364 | 8/2018 |
| WO | WO 2018/160456 | 9/2018 |
| WO | WO 2018/227048 | 12/2018 |
| WO | WO 2019/013994 | 1/2019 |
| WO | WO 2019/074815 | 4/2019 |
| WO | WO 2019/177909 | 9/2019 |
| WO | WO 2019/195860 | 10/2019 |
| WO | WO 2019/231744 | 12/2019 |
| WO | WO 2019/236654 | 12/2019 |
| WO | WO 2020/106705 | 5/2020 |
| WO | WO 2020/109594 | 6/2020 |
| WO | WO 2020/109596 | 6/2020 |
| WO | WO 2020/109599 | 6/2020 |
| WO | WO 2020/123719 | 6/2020 |

OTHER PUBLICATIONS

Alain Carpentier, Cardiac valve surgery—"the French Correction". 86 The Journal of Thoracic and Cardiovascular Surgery 323-337, Sep. 1983.

Junior, et al., "Surgical repair of chordae tendineae rupture after degenerative valvular regurgitation using stardardized bovine percardium", Jan. 2013, Rev. Bras Cir Cardiovascular 2013; 28(1):36-46.

International Search Report for International Application No. PCT/US16/69567 dated Mar. 23, 2017.

Kobayashi et al. "Ten Year Experience of Chordal Replacement with Expanded Polytetrafluoroethylene in Mitral Valve Repair." Circulation. American Heart Association. Nov. 7, 2000. pp. III-30-III-34.

International Search Report and Written Opinion received in PCT Application No. PCT/US2019/021480, dated Jul. 15, 2019 in 16 pages.

(56) References Cited

OTHER PUBLICATIONS

International Search Report and Written Opinion received in PCT Application No. PCT/US2019/065814, dated Apr. 1, 2020 in 14 pages.

* cited by examiner

METHOD AND APPARATUS FOR TRANSVASCULAR IMPLANTATION OF NEO CHORDAE TENDINAE

INCORPORATION BY REFERENCE TO ANY PRIORITY APPLICATIONS

This application is a continuation-in-part of U.S. application Ser. No. 15/638,176, filed Jun. 29, 2017, which claims priority to U.S. Provisional Application 62/441,031, filed on Dec. 30, 2016, the entirety of each of these applications is hereby incorporated by reference herein for all purposes. Any and all applications for which a foreign or domestic priority claim is identified in the Application Data Sheet as filed with the present application are hereby incorporated by reference under 37 CFR 1.57.

BACKGROUND

Field

The disclosure relates generally to mitral valve repair devices and techniques, and in particular, to transvascular methods and devices for chordae tendinae replacement to reduce mitral regurgitation.

Description of the Related Art

The heart includes four heart valves, which allow blood to pass through the four chambers of the heart in one direction. The four valves are the tricuspid, mitral, pulmonary and aortic valves. The four chambers are the right and left atria (upper chambers) and right and left ventricle (lower chambers).

The mitral valve is formed by two leaflets, which are known as the anterior leaflet and the posterior leaflet, which open and close in response to pressure placed on the leaflets by the pumping of the heart. There are several problems that can develop or occur with respect to the mitral valve. Such problems include mitral valve regurgitation (MR), in which the mitral valve leaflets do not close properly, which can cause leakage of the mitral valve. Severe mitral regurgitation can adversely affect cardiac function and compromise a patient's quality of life and life-span.

Several techniques have been developed, for correcting mitral valve regurgitation. These include heart transplant, valve replacement or repair, chordae tendinea shortening or replacement and mitral annular repair also known as annuloplasty, depending upon the stage and underlying etiology.

As it relates to chordae tendinea replacement or repair, certain surgical and trans apical approaches have been proposed. Despite those efforts, however, there remains a need for a transvascular approach for chordae tendinea replacement or repair, to reduce or eliminate MR.

SUMMARY OF THE INVENTION

There is provided in accordance with one aspect of the present disclosure, a method of transvascular prosthetic chordae tendinea implantation. The method can comprise the steps of advancing a catheter into the left atrium, through the mitral valve, and into the left ventricle, and deploying a ventricular anchor from the catheter and into a wall of the left ventricle, leaving a ventricular suture attached to the ventricular anchor and extending proximally through the catheter. A leaflet anchor is deployed to secure a mitral valve leaflet to a leaflet suture, with the leaflet suture extending proximally through the catheter. The leaflet suture is secured to the ventricular suture to limit a range of travel of the leaflet in the direction of the left atrium.

The deploying a leaflet anchor step may comprise securing the leaflet anchor to the leaflet within the range of from about 3 mm to about 10 mm from a leaflet coaptive edge. The deploying a ventricular anchor step may comprise attaching the anchor to the ventricular septum or the ventricle wall, preferably spaced apart from the apex. The deploying a ventricular anchor step may comprise advancing an anchor driver through the mitral valve, rotating the driver to secure the ventricular anchor, and proximally retracting the anchor driver to expose the ventricular suture carried by the ventricular anchor.

The deploying a leaflet anchor step may comprise positioning a needle guide in contact with the leaflet and advancing a needle from the needle guide and through the leaflet. The method may further comprise deflecting a distal portion of the needle guide through an angle of at least about 160 degrees to position a distal end of the needle guide against the ventricle side of the leaflet. The needle guide may comprise a slotted tube and deflecting the needle guide may be accomplished by proximally retracting a pull wire.

The securing step may comprise applying a suture lock to the ventricular suture and the leaflet suture. The method may further comprise applying tension to the leaflet suture prior to the securing step, to improve leaflet function. The method may further comprise applying sufficient tension to the leaflet suture to pull the limit of leaflet travel during systole to approximately to the level of the annulus. The securing step may comprise engaging a knot to secure the leaflet suture and the ventricular suture. The method may additionally comprise the step of cutting the leaflet suture and the ventricular suture proximally of the suture lock or knot, leaving the leaflet suture and the ventricular suture to function as a native chordae.

The method may additionally comprise the initial step of identifying a patient including at least three characteristics selected from the group consisting of: the patient has been diagnosed with primary or degenerative mitral regurgitation; the patient has been diagnosed with secondary or functional Mitral Regurgitation; the patient has been diagnosed with Mixomotous Mitral Regurgitation; the patient has been diagnosed with a flail leaflet, ruptured chordae, or leaflet prolapse; the patient has Mitral regurgitation grade 1 or more; the patient has annular diameter from A2 leaflet to P2 leaflet at least 5 mm less than sum of length of P2+A2 leaflet; the patient has annular diameter from A2 to P2 leaflet of at least 10 mm; and the patient has an access vessel diameter of at least 2 mm.

The patient may additionally have at least one characteristic selected from the group consisting of: the patient has been evaluated by a heart team including at least one cardiac surgeon and determined not to be an appropriate candidate for conventional open surgical repair; the patient has STS predicted operative mortality (STS Score) of 2 or greater; the patient was offered and refused open surgical repair; the patient is age between 18 and 90; the patient will not accept blood transfusion; the patient has had prior open chest surgery; and the patient has an ejection fraction of at least 10 percent.

In accordance with a further aspect of the present disclosure, there is provided a method of increasing mitral valve leaflet coaptive area during systole. The method comprises the steps of securing at least a first ventricular tension element to a wall of the ventricle and securing at least a first leaflet tension element to a mitral valve leaflet. The leaflet tension element is proximally retracted to move the limit of travel of the leaflet during systole in the direction of the ventricle, thereby increasing mitral valve leaflet coaptive area during systole. The leaflet tension element is thereafter secured to the ventricular tension element.

The ventricular tension element may comprise a neo papillary muscle having a distal end facing the ventricular anchor, and a proximal end approximately at the height of the top of the native papillary muscle, and the securing step may comprise securing the leaflet tension element to the ventricular tension element at the proximal end of the neo papillary muscle. The neo papillary muscle may comprise an elongate, atraumatic body, and may comprise ePTFE.

The securing a leaflet tension element step may comprise advancing a needle guide having a distal end through the mitral valve and into the left ventricle, and deflecting the needle guide through an angle of at least 160 degrees to place the distal end into contact with the leaflet during diastole. The method may further comprise advancing a leaflet anchor deployment needle out of the distal end of the needle guide and through the leaflet, and deploying an anchor from the needle. The deploying an anchor step may comprise deploying an anchor from a first, reduced cross section within the deployment needle, to a second, enlarged cross section for seating against the atrial side of the leaflet. The deploying an anchor step may comprise deploying a pledget.

The proximally retracting the leaflet tension element step may comprise positioning an aperture in the left ventricle, with at least the leaflet tension element extending through the aperture, and proximally retracting the leaflet tension element with the aperture functioning as a fulcrum so that the tension element draws the leaflet in the direction of the ventricle. The fulcrum may comprise a distal opening of a catheter and the proximally retracting step may comprise proximally retracting the leaflet tension element through the catheter. The method may further comprise securing a second leaflet tension element to the leaflet and to the ventricular tension element.

In accordance with a further aspect of the present disclosure, there is provided an assembled in situ mitral valve leaflet restraint. The restraint comprises an elongate, flexible neo papillary muscle, having a proximal end and a distal end, and a helical tissue anchor attached to the distal end of the neo papillary muscle. An elongate, flexible neo chordae extends proximally from the neo papillary muscle, and a leaflet anchor is attached to a proximal end of the neo chordae. The leaflet anchor is enlargeable from a first reduced cross section for advancing through the leaflet, to a second, enlarged cross section for contacting an atrial side of the leaflet. The neo chordae may be attached to a suture extending distally through the neo papillary muscle to the helical tissue anchor.

The helical anchor may comprise a laser cut hypotube. The helical anchor may comprise one or two or more coiled round wires. The neo chordae may comprise a suture extending from a proximal end of the neo papillary muscle to the leaflet anchor. The suture may extend through the neo papillary muscle to the helical tissue anchor.

The neo chordae may comprises a first component extending proximally from the neo papillary muscle and a second component extending distally from the leaflet anchor. A proximal portion of the first component and a distal portion of the second component can be joined together by a locking device. The locking device can have a locked configuration and an unlocked configuration. The locking device may be configured to be advanced over the first component and the second component when in an unlocked configuration and to fixedly clamp the first component and the second component when in a locked configuration.

The leaflet anchor may comprise a pledget. The pledget can be configured to be collapsed by pulling a suture coupled to the pledget so that the pledget assumes the second, enlarged cross section when collapsed. A suture may be threaded through at least two, at least three, or more than three apertures in the pledget. The apertures may be substantially collinear. The leaflet anchor may comprises a T tag bar. The T tag bar may include a bar rotatably coupled to a suture such that rotation of the bar enlarges the leaflet anchor from the first reduced cross section to the second, enlarged cross section. The leaflet anchor may comprise a hub. The hub can include a plurality of flexible radially extending spokes. The spokes may be configured to bend into alignment along a longitudinal axis so as to be confined within a delivery needle. The spokes may be biased to expand radially outward when unconfined to enlarge the leaflet anchor from the first reduced cross section to the second, enlarged cross section.

The helical anchor may comprises a hub configured for receiving and frictionally securing a suture. The helical anchor may comprise a loop for securing the neo papillary muscle to the helical anchor. The neo papillary muscle may comprise a soft ribbon.

In accordance with a further aspect of the present disclosure, a neo chordae tendinae deployment system can include an elongate, flexible tubular body, having a proximal end and a distal end. A helical ventricular anchor can be positioned within the tubular body, having a rotational driver extending proximally through the tubular body. A radially enlargeable leaflet anchor within the tubular body, having a suture extending proximally through the tubular body.

In accordance with a further aspect of the present disclosure, there is provided a neo chordae tendinae deployment system. The deployment system comprises a catheter having a proximal end and a distal end; a helical anchor within the catheter; and a radially enlargeable leaflet anchor within the catheter. The helical anchor has a driver configured to rotate the helical anchor and extending proximally through the catheter. The leaflet anchor has a suture extending proximally through the catheter.

The radially enlargeable leaflet anchor may comprise a pledget. The pledget may be transformable from an elongate strip configuration to a radially enlarged, axially shortened configuration by proximal retraction of the suture. The radially enlargeable leaflet anchor may comprise the suture inserted between two sheets of material. The radially enlargeable leaflet anchor may comprise a deflectable deployment tube carried within the catheter.

A distal deflection zone of the deployment tube can be deflectable through an angle of at least about 160 degrees in response to manipulation of a proximal deflection control. The distal deflection zone may be within about 1.5 cm from a distal end of the deployment tube. The distal deflection zone may be deflectable to form a curve having a best fit radius of no more than about 1.5 cm. The deflectable deployment tube may comprise a slotted deflection tube.

The neo chordae tendinae deployment system can be configured to deploy the helical anchor in a distal direction, and to deploy the radially enlargeable anchor in a proximal direction. The enlargeable leaflet anchor can be sequentially inserted into the catheter after the helical anchor and driver have been removed from the catheter. The enlargeable leaflet anchor and the helical anchor and driver can be preloaded within the catheter.

In accordance with a further aspect of the present disclosure, there is provided a leaflet anchor delivery system. The leaflet anchor delivery system comprises a delivery shaft and a tissue piercing element. The delivery shaft has a distal portion, a proximal portion, and a deflection zone positioned at a distal portion of the delivery shaft. The tissue piercing element is configured to be advanced through the distal end of the delivery shaft. The deflection zone is configured for positioning the distal end of the delivery shaft on the ventricular side of the leaflet with the proximal portion of the delivery shaft extending into the left atrium. The deflection zone may comprise a flex tube. The flex tube when deflected can have a best fit radius of curvature of less than about 2 cm.

In accordance with a further aspect of the present disclosure, there is provided a pledget for anchoring to a heart leaflet. The pledget comprises two flat sheets comprising substantially overlapping areas; a suture positioned between the two flat sheets; and one or more apertures extending through the two flat sheets. The suture has a proximal end and a distal end. The proximal end extends from a first side of the two flat sheets. The one or more apertures extending through the two flat sheets are sized to receive the suture. The two flat sheets are joined together over portions of the overlapping areas on both sides of the suture.

The suture may be at least partially flattened between the two sheets. The one or more apertures may extend through the flattened suture. The distal end of the suture may extend to a second side of the two flat sheets, opposite the first side. The suture may extend between the two flat sheets along a substantially straight line. The suture may extend between the two flat sheets along a zig-zag or undulating direction. The two flat sheets may comprise expanded polytetrafluoroethylene. At least one of the two flat sheets may be at least partially sintered.

A proximal end of the suture extending from the first side of the two flat sheets can be threaded through the one or more apertures. The pledget may comprise a collapsed configuration in which the two flat sheets are folded over at least once to form a radially enlarged cross section. The radially enlarged cross section may extend around the suture as it passes through the one or more apertures.

BRIEF DESCRIPTION OF THE DRAWINGS

FIGS. 35I-1 through 35I-4 illustrate deployment of a T tag type leaflet anchor.

FIGS. 35J-1 through 35J-3 illustrate deployment of a radially expandable tissue anchor.

FIG. 36A is a picture of a looped papillary muscle in a configuration it is first captured in.

DETAILED DESCRIPTION OF THE PREFERRED EMBODIMENTS

Figure 1:
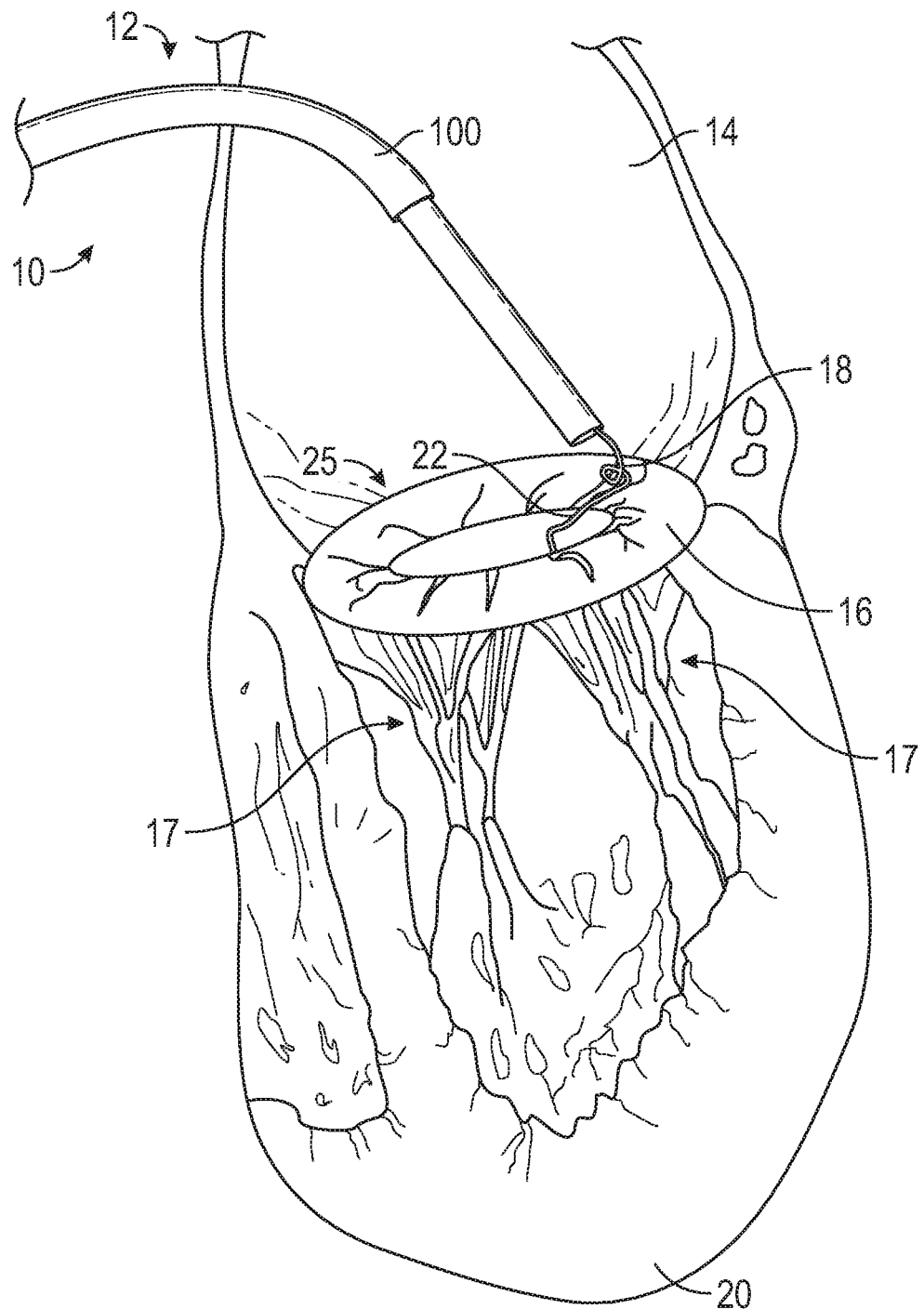
FIG. 1 illustrates the mitral valve annulus with a suture attached as delivered via catheter.

An embodiment to attach a ruptured or flail chord could include a catheter delivered through the femoral vein and traversed up into the inferior vena cava (IVC) and transseptal to the left atrium where an attachment is made to the mitral annulus. This attachment could be a single suture loop through the mitral annular tissue or an anchor inserted into the annulus either rotated, pierced into or threaded to the local tissue where the mitral leaflet meets the atrial tissue at or near the mitral annulus. The anchor could be constructed of a coiled-wire anchor which would be rotated into the tissue with a suture receiver for chordal replacement or a pre-attached chordal affixed to the anchor.

A connection to the mitral annulus can provide a secure and positive attachment point as a stable anchor through a piercing, hook or corkscrew anchoring device. To this attachment point a chord can be connected to drape over the mitral valve leaflet and further attached or anchored into the apex of the left ventricle. It could also be pierced through the anterior or posterior mitral leaflets at any position. The chord can be made of round, flat PTFE, PE or nylon as conventionally used in surgery for chordal repair.

In some embodiments, the chord may serve as a neochord or prosthetic chord. The chord may be a standard suture in certain embodiments. In some embodiments, one or more additional prosthetic elements may be secured over the chord. For example, tubular structures may be advanced (e.g., slid) over the cord through the delivery device. The structures may be configured to self-position themselves as appropriately along the length of the chord or the structures may be secured to the chord along at an appropriate position (e.g., by placing locking members proximally and/or distally of the structure). Any suitable locking members may be used to position structures in place. Locking members may be crimpable, may comprise mechanical locking mechanisms, and/or may frictionally engage the chord require a threshold amount of force to be advanced over the chord. Any suitable type of locking member may be used. Locking members may be similar to suture locks described elsewhere herein. In some embodiments, locking members may be configured to be advanced distally and proximally over the chord. In some embodiments, locking members may be configured to advance in only one direction (e.g., distally over the chord). In some embodiments, additional prosthetic structures may be secured at a proximal end, distal end, or intermittently along the length of the chord. The chord may attach to a proximal or distal end of the prosthetic structure. For example, two chords may be used, one attached to a proximal end of the structure and one attached to a distal end of the structure. In some embodiments, the chord may connect to the structure, for example at a proximal and/or distal end (e.g., inserted through or wrapped around a loop on the structure), and run parallel along the length of the structure. The prosthetic structure may be configured for contact with one or more physiological tissues (e.g., for interfacing with the leaflet) and/or may be configured to replicate the mechanical/structural properties of physiological structures (e.g., the papillary muscle).

Anchoring to the annulus can provide an attachment point which is positive and immobile with respect to the mitral leaflets which are difficult to capture with a ruptured chord due to the movement at each heartbeat. This movement can be halted with a grasping of the flail leaflet by a mechanical gripper tool, suction tube or a cryo-catheter to freeze-grab the leaflet as will described in more detail below in relation to certain illustrated embodiments. As the upper anchor is positively attached to the mitral annulus it can be draped over the mitral leaflet and between the existing chords to limit the location laterally with respect to the leaflet. Locating the leaflet between existing chords provides the artificial chord a positive anchor at the upper anchor point, a secured angular location passing through the existing chords and another positive location at the apex of the left ventricle. The replacement chord can be a single suture strand or a plurality of chords traversing up and down the pathway as described above allowing the load to be carried by a plurality of chords.

The lower apical anchor that can be located in the left ventricle can be secured via a rotational screw or plug to hold the chord positively. The anchor could be short in height and close to the base of the apex or have an extended length to better match the native papillary muscles of about 20-22 millimeters above the apex of the left ventricle. In some embodiments, the anchor extend about less than 5 mm, 5 mm, 10 mm, 15 mm, 20 mm, 25 mm, 30 mm, 35 mm, 40 mm, 45, mm, 50 mm, or more than 50 mm above the apex and/or a range between the afore-mentioned values. A single chord or plurality of chords could be attached to one or more anchors at the base of the left ventricle. The anchor could be constructed of an implantable grade of stainless steel, Nitinol or other metallic material that would be visible on fluoroscopy or a polymeric material such as PEEK, PTFE or other implantable materials. These polymers could be doped with a radiopaque marker for visibility if needed.

An embodiment for the anchoring system could comprise of the apical tissue anchor which couples or attaches to the left ventricle, a riser which projects the attachment from the apical tissue anchor and could be constructed from a monolithic material or a combination of materials including polymers and metallic components. The construction could be rigid throughout or have flexible joints to allow movement or an elastic zone or zones for controlled motion and flexibility. It could be constructed of a round crossing profile or any other profile including a varying shape longitudinally. The diameter could be about 6 to 24 French (2 to 8 millimeters) and length about 20 to 40 millimeters and delivered via steerable catheter with or without a guidewire generally along the central axis. Once the upper leaflet anchor is attached to the mitral annulus or leaflet and draped over the mitral leaflets and further coupled to the lower anchor a tension force would allow for an adjustment via real time imaging/monitoring (e.g., under live echo) while monitoring the leaflet motions and regurgitant flow reduction. The final step could be to tension, lock and disconnect the chord from the delivery system. A tension of the chord would apply tension to the connected mitral valve leaflet strain relief and a locking device such as a Cor-Knot from LSI Solutions could be advanced down the chord and lastly the suture tail could be cut.

According to one embodiment (see FIGS. 1-7), the steps of the replacement chord delivery could include:
1. Trans-venous, trans-femoral entry of the delivery catheter 100
2. Catheter 100 advancement to the right atrium 10
3. Trans-septal advancement 12 of catheter 100 into the left atrium 14
4. Catheter 100 advancement to the mitral annulus 16 for the strain relief anchor 18 positioning and delivery
5. Positioning of a grasping tool of the mitral leaflet
6. Strain relief anchor 18 attachment to the mitral annulus 16
7. Replacement Chord 22 advancement over the mitral valve 25 and between the existing chords 17
8. Chord 22 advancement to the apex 20 of the left ventricle and distal attachment into the apex 20
9. Tensioning of the chord 22 while monitoring the mitral valve leaflet motion Alternatively, in certain embodiments (see e.g., FIGS. 26-34), the delivery could be in a somewhat opposite order:
1. Trans-femoral entry of the delivery catheter 100
2. Catheter 100 advancement to the right atrium 10
3. Trans-septal advancement 12 of Catheter 100 into the left atrium 14
4. Advancement of the delivery catheter 100 through the mitral valve 24 to the apex 20 of the left ventricle
5. Delivery of the distal ventricular anchor (e.g., rotational anchor 32) into the apex 20
6. A withdrawal of the delivery catheter 100 to expose the lower apex anchor 30
7. Pulling the delivery catheter 100 proximal to expose the new chord suture line 22 or lines 22
8. Over each new chord 22 a mitral leaflet strain relief can be delivered through the mitral leaflet and on the ventricular side of the leaflet
9. An advancement of a suture lock 26 over the suture tail 28 to lock the position of the suture to the position of the strain relief anchor
10. A cutting of the suture tail at the mitral leaflet anchor
11. An advancement of a suture lock 26 over the suture tail from the catheter handle to the mitral leaflet anchor
12. An advancement of a suture lock 26 over the suture tail from the catheter handle to the distal apex anchor locking the tension as applied from the distal most suture tail outside the catheter handle
13. A cutting of the suture tail at the distal apex anchor Some of the steps of these methods may be optional. Additional steps may be included where appropriate. Furthermore, the steps may be rearranged into any feasible order.

Figure 2:
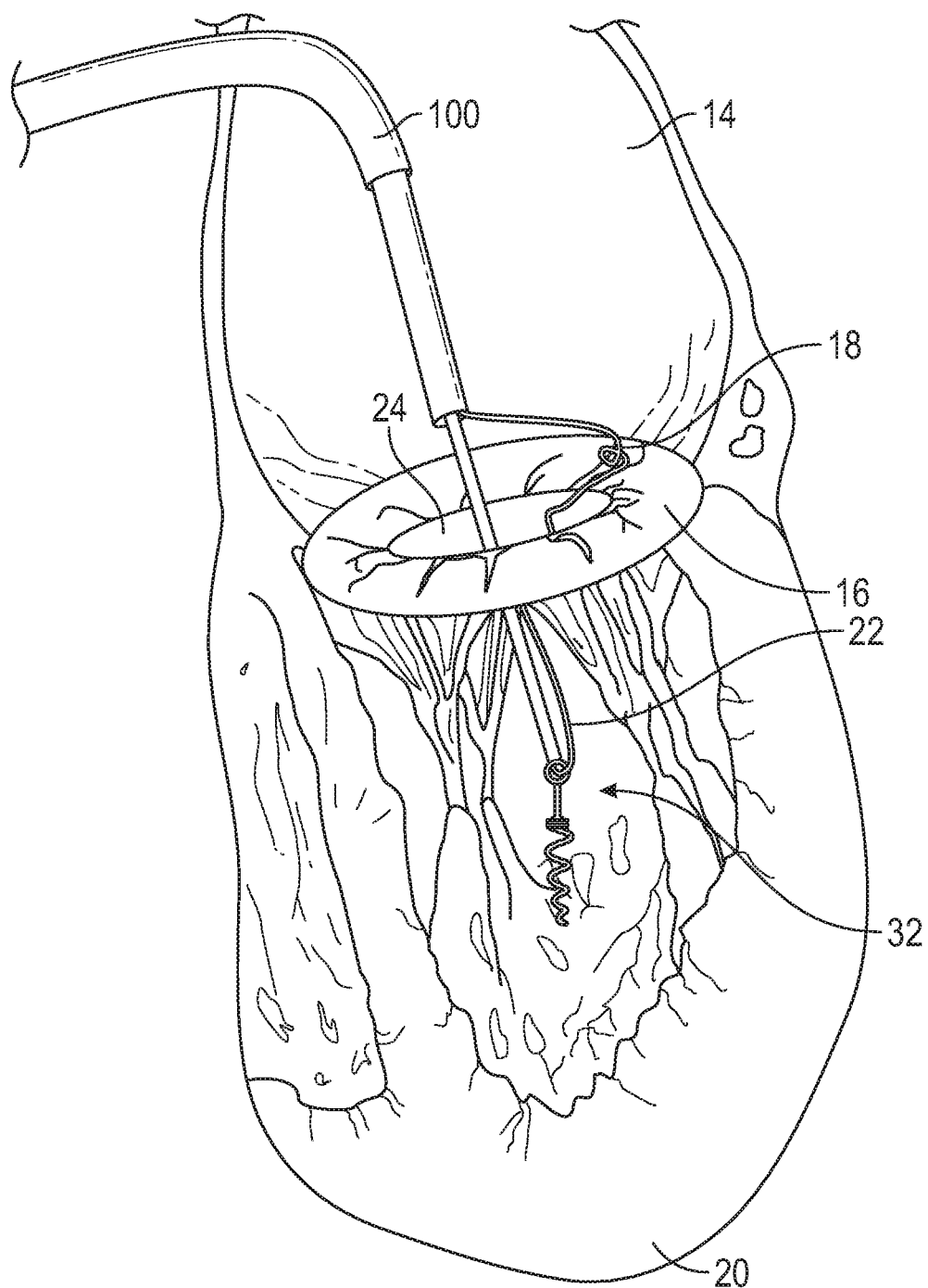
FIG. 2 illustrates the distal anchor being delivered via catheter and attached to a suture further connected to the mitral annulus.
Figure 3:
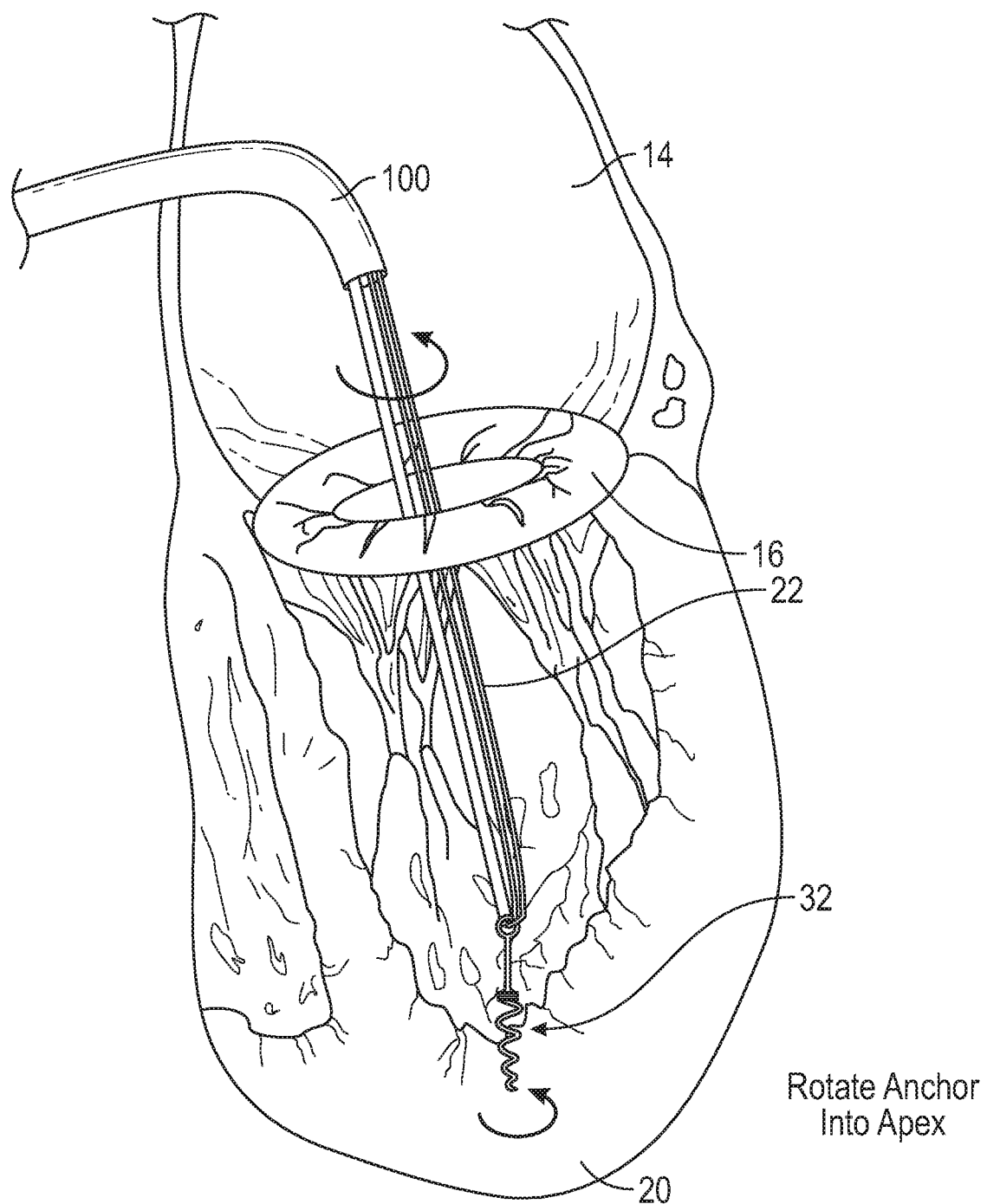
FIG. 3 illustrates the distal anchor being rotated into the apex of the heart with suture lines attached for later attachment to the mitral leaflet or the mitral annulus.
Figure 4:
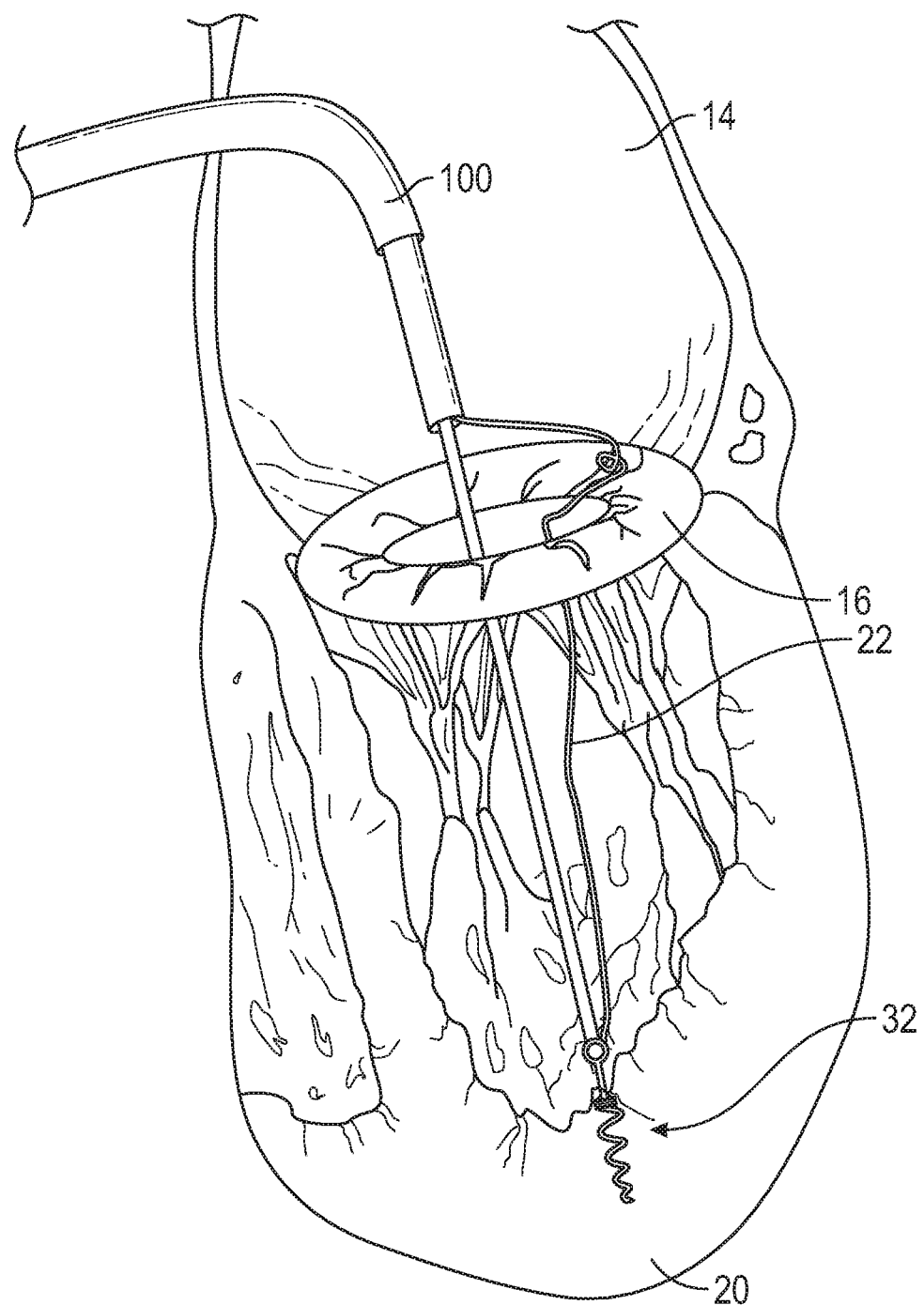
FIG. 4 illustrates the distal anchor rotated into the apex of the heart with suture lines attached to the mitral leaflet or the mitral annulus.
Figure 5:
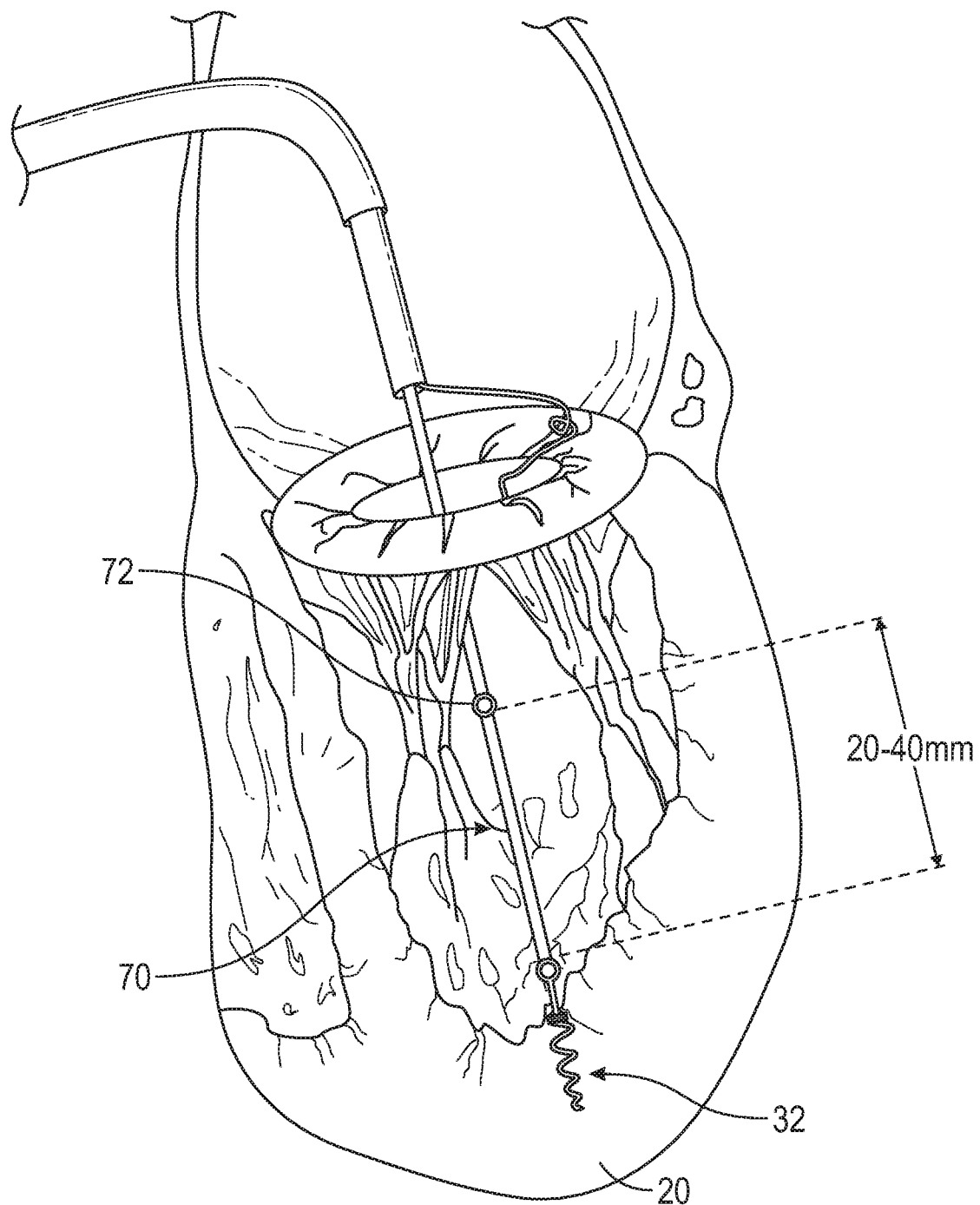
FIG. 5 illustrates the distal anchor attached and projected above the apex of the heart approximately the same height as the top of the papillary muscles.
Figure 6:
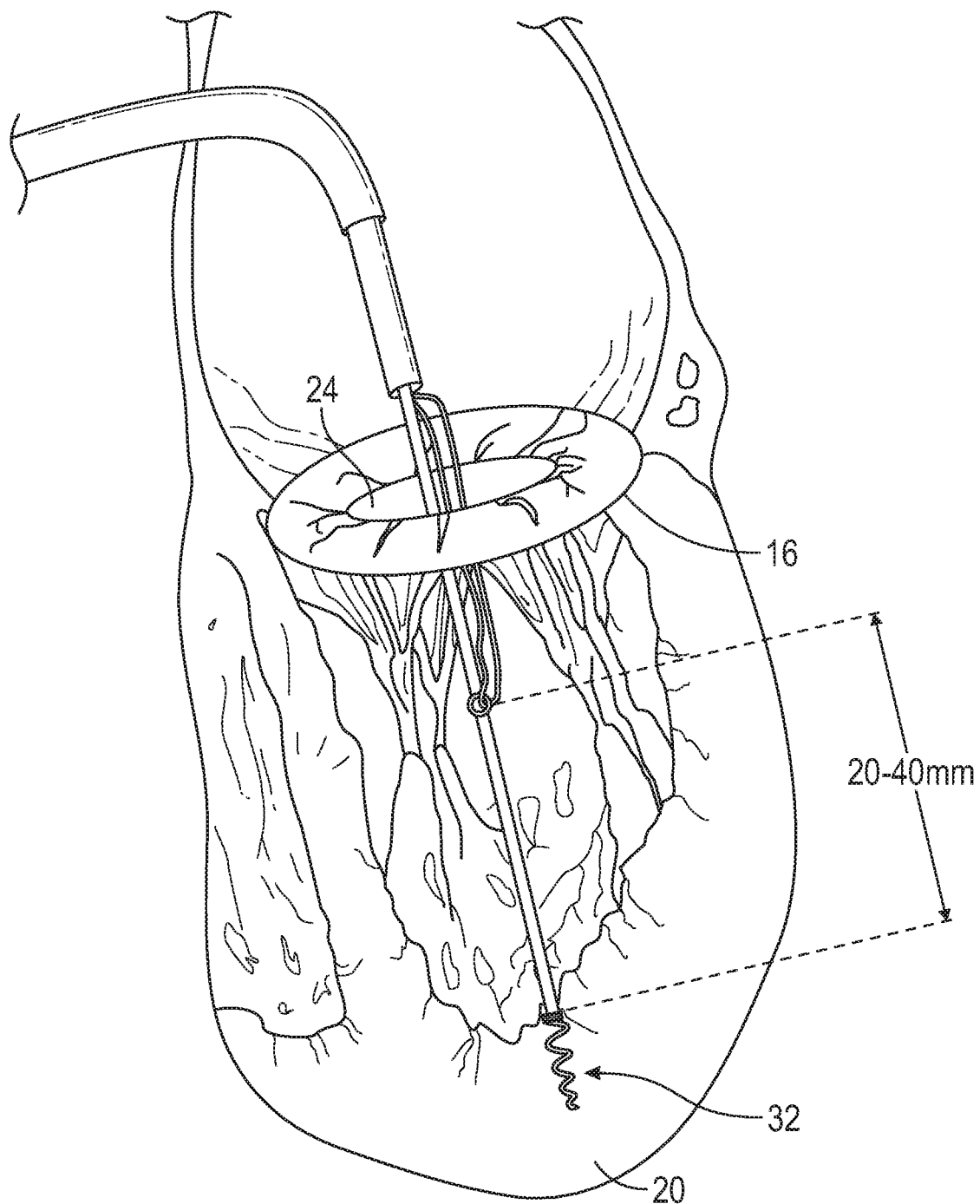
FIG. 6 illustrates the distal anchor attached and projected above the apex of the heart approximately the same height as the top of the papillary muscles and attached to the mitral annulus and or mitral leaflet.
Figure 7:
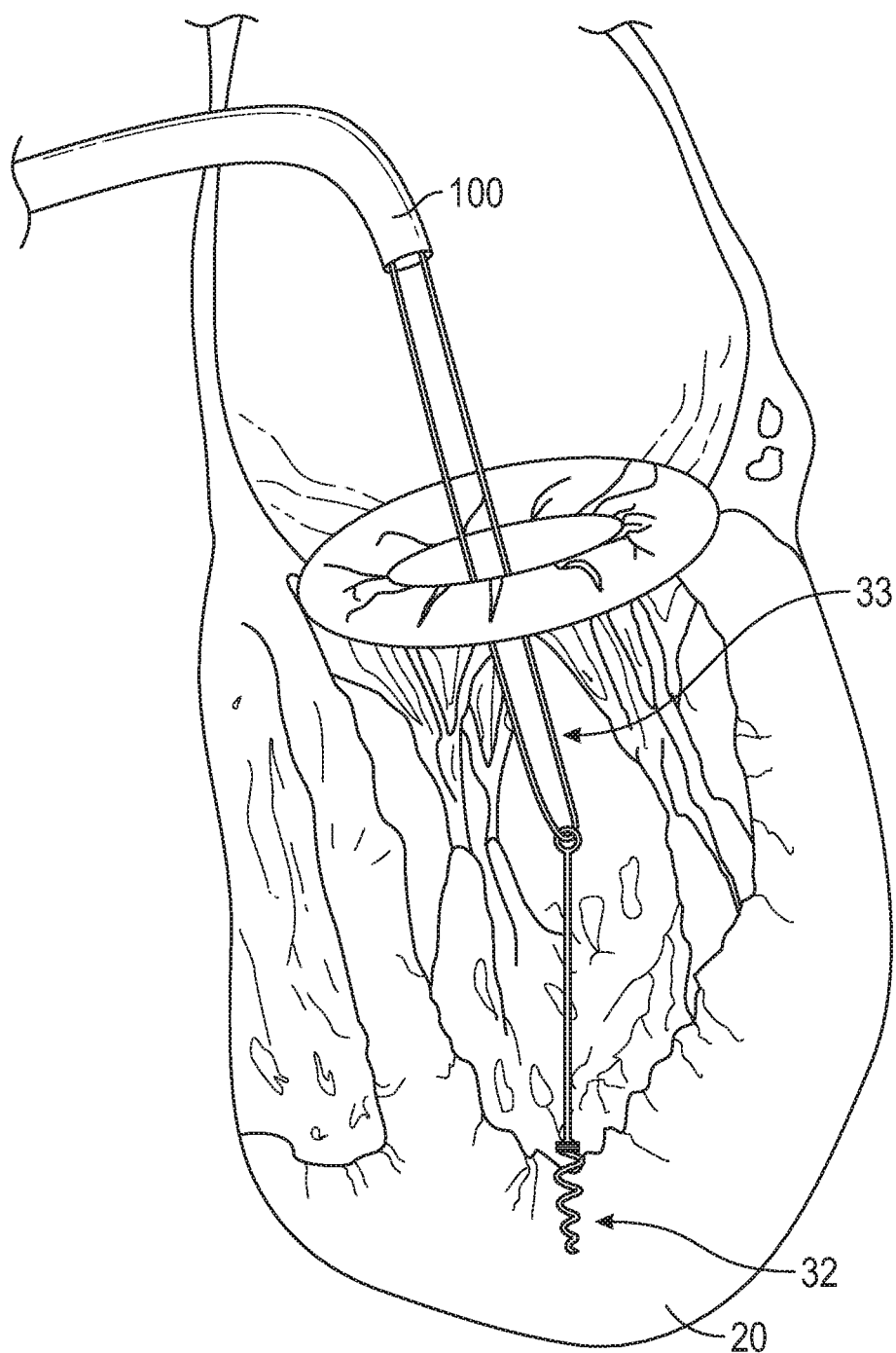
FIG. 7 illustrates the distal anchor attached and projected above the apex of the heart approximately the same height as the top of the papillary muscles and attached to a loop suture traversing through the catheter.

An embodiment according to FIGS. 1-7 will now be described with additional detail. FIG. 1 illustrates the mitral valve annulus 16 with the suture 22 attached as delivered via the catheter 100. FIG. 2 illustrates the distal anchor 32 being delivered via the catheter 100 and attached to the suture 22 further connected to the mitral annulus 16. FIG. 3 illustrates the distal anchor 32 being rotated into the apex 20 of the heart with suture lines 22 attached for later attachment to the mitral leaflet 24 or the mitral annulus 16. FIG. 4 illustrates the distal anchor 32 rotated into the apex 20 of the heart with suture lines 22 attached to the mitral leaflet 24 or the mitral annulus 17. FIG. 5 illustrates the distal anchor 32 attached and projected above the apex 20 of the heart approximately the same height as the top of the papillary muscles. The anchor 32 can include a riser 70 connected to a connection point 72 having a length of about 20-40 mm in certain embodiments. The riser 70 may be of a same or different material, diameter, stiffness, etc. as the remainder of the anchor 32. The riser 70 may be in longitudinal alignment with the remainder of the anchor 32 or may be positioned at an angle to the remainder of the anchor 32. The riser 70 may be rigidly fixed or integrated to the remainder of the anchor 32, coupled in an articulable manner (e.g., joint/socket), or flexibly joined (e.g., interconnecting loops). The tension placed on the anchor 32 upon installation of the neo chordae may determine or alter the orientation of the riser 70 with respect to the heart and/or remainder of the anchor 32. FIG. 6 illustrates the distal anchor 32 attached and projected above the apex 20 of the heart approximately the same height as the top of the papillary muscles. The distal anchor 32 may be attached via one or more suture lines to the mitral annulus 16 and or mitral leaflet 24. FIG. 7 illustrates the distal anchor 32 attached and projected above the apex 20 of the heart approximately the same height as the top of the papillary muscles and attached to a suture 33 in a form of a loop traversing through the catheter 100.

Figure 8:
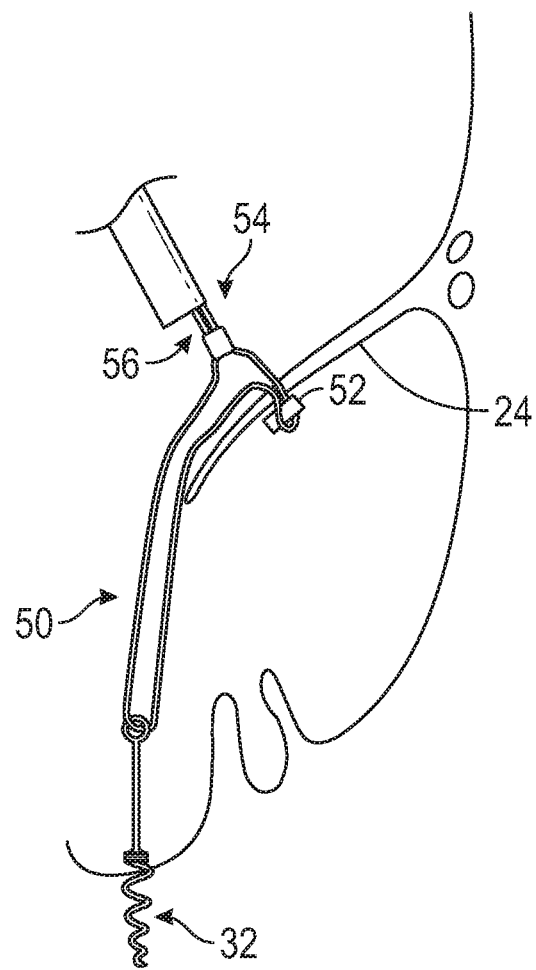
FIG. 8 illustrates a catheter delivered suture loop pierced through the mitral leaflet with a strain relief on the ventricular side of the mitral leaflet and a distal anchor in the bottom of the left ventricle with the final suture tension adjustment being held with a suture lock advanced over the suture tails.

FIG. 8 illustrates an embodiment in which a catheter delivered suture 50 in a form of a loop can be pierced through the mitral leaflet 24 with a strain relief 52 on the ventricular side of the mitral leaflet 24 and a distal anchor 32 in the bottom of the left ventricle with the final suture tension adjustment being held with a suture lock 54 advanced over the suture tails 56. The single suture loop 50 may join the distal anchor 32 to the strain relief 52, directly to the distal anchor, and/or to another leaflet anchor. More than one loop may also be used. In some embodiments, the suture 50 may pass through a loop structure in the distal anchor 32 and/or the strain relief 52 such that it effectively doubles back on itself. In some embodiments, the suture 50 may pass through a channel in the distal anchor 32 and/or strain relief 52 such that a proximal end of the suture 50 enters at one opening and a distal end of the suture 50 exits at another opening. The openings may be positioned on the same side of the distal anchor 32 and/or strain relief 52. The openings may be positioned on opposite sides of the distal anchor 32 and/or strain relief 52. The relative length of the suture tails 56 extending from the distal anchor 32 and the strain relief 52 may determine the effective final positioning of the suture lock 56. For example, by minimizing the length of the suture tail 56 extending from the strain relief 52, the suture lock 54 may be effectively positioned on the atrial side of the mitral leaflet 24, such as directly over the strain relief 52. By minimizing the length of the suture tail 56 extending from the proximal end of the distal anchor 32, the suture lock 54 may be effectively positioned just above the distal anchor 32. The suture lock 54 may be any suitable type of suture locking mechanism, including those described elsewhere herein. The strain relief 52 may comprise an expandable conformation, such that the strain relief 52 is inserted through the leaflet 24 in a collapsed conformation (e.g., a reduced cross-section conformation) and expanded (e.g., to an expanded cross-section conformation) on the ventricular side of the leaflet 24. The strain relief 52 may be self-expanding. In some embodiments, the strain relief 52 may be a pledget as described elsewhere herein. The strain relief 52 may be inserted via a needle or other suitable implement for piercing the leaflet 24 tissue, such as those described elsewhere herein. The strain relief 52 may be stored inside and advanced through an internal lumen of the needle. The needle may constrain the strain relief 52 in a collapsed conformation. The strain relief 52 may be inserted through the leaflet 24 with the suture 50 pre-loaded (e.g., looped through the strain relief) such that both the proximal end and distal end of the suture 50 extending from the strain relief remain extending through the puncture through the leaflet 24 when the strain relief 52 is installed. The suture lock 54 can prevent the suture tails 56 from advancing or retracting through the suture lock 54, thereby, holding the suture chords in a state of tension after the suture lock 54 engaged, allowing the tails 56 to be severed proximal to the suture lock 54. The tails 56 of the suture 50 may be severed directly adjacent to the suture lock 54 or proximally distant to the suture lock 54 allowing a length of the tails 56 to freely extend from the suture lock 54. The strain relief 52 and the distal anchor may be loaded onto the suture loop 50 outside of the body and sequentially installed through the catheter 100 in any order.

Figure 9:
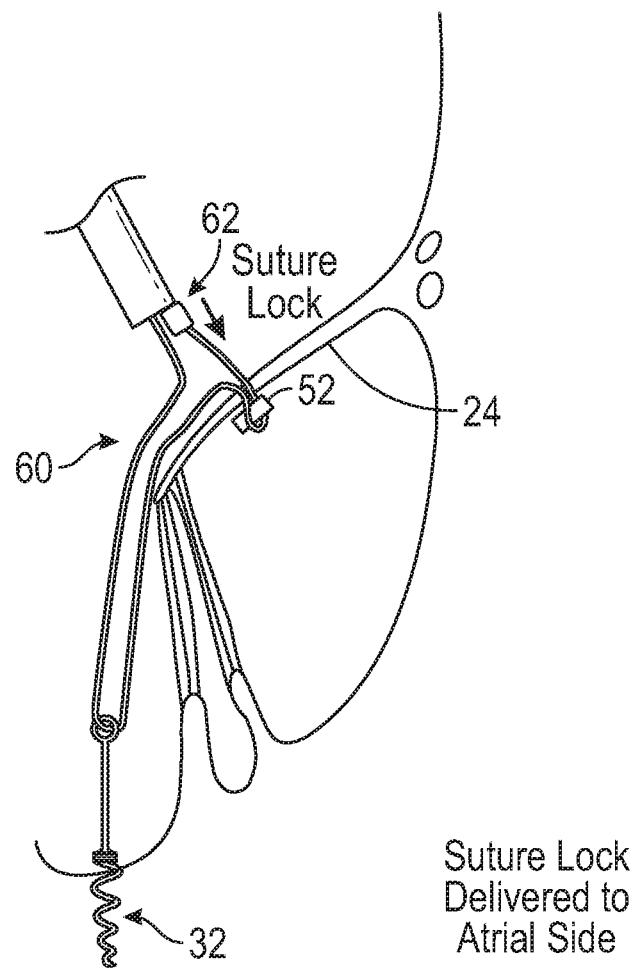
FIG. 9 illustrates a catheter delivered suture line pierced through the mitral leaflet with a strain relief on the ventricular side of the mitral leaflet and a suture lock being advanced to the atrial side of the mitral leaflet to secure the suture tail before cutting of the suture.

FIG. 9 illustrates an embodiment in which a catheter delivered suture line or loop 60 can be pierced through the mitral leaflet 24 with a strain relief 52 on the ventricular side of the mitral leaflet 24. The strain relief 52 may be inserted as described with respect to FIG. 8. In this embodiment, a suture lock 62 can be advanced to the atrial side of the mitral leaflet 24 to secure the suture tail before cutting of the suture 60. The suture lock 62 can be advanced along only one tail of the suture 60, such that it does not secure the suture tail extending from the distal anchor 32, only the tail extending from the strain relief 52. The suture lock 62 can be configured (e.g., size and/or shaped) to prevent the suture lock from being pulled through the puncture in the mitral leaflet 24 when under tension. The suture tail extending from the distal anchor 32 may be secured as described with respect to FIG. 10.

Figure 10:
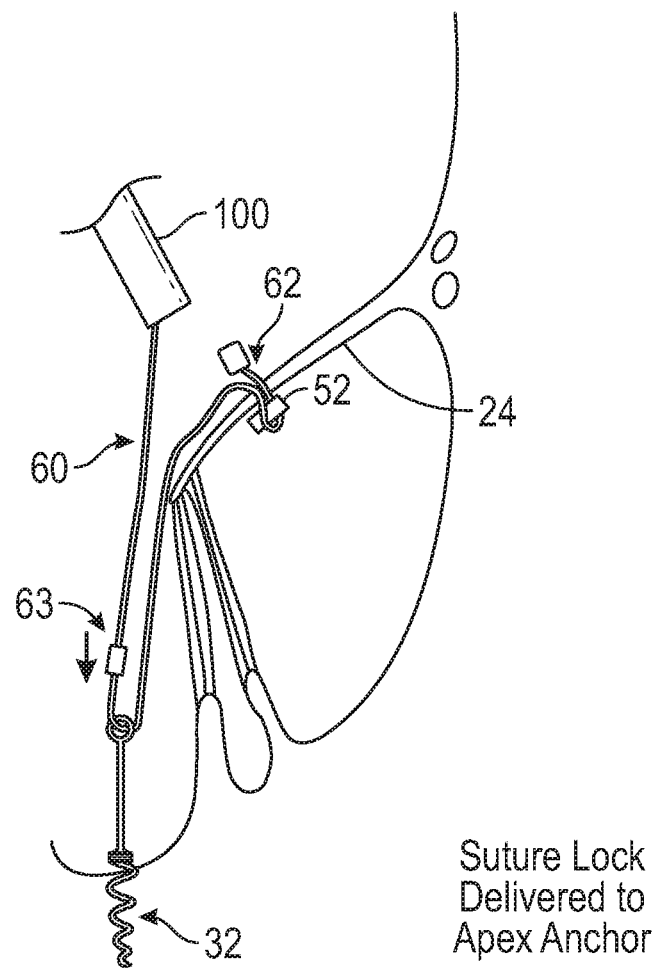
FIG. 10 illustrates a catheter delivered suture line pierced through the mitral leaflet with a strain relief on the ventricular side of the mitral leaflet and a suture lock advanced to the atrial side of the mitral leaflet to secure the suture tail. The other end of the suture tail extends from the catheter handle through the catheter traversing about the distal anchor located in the bottom of the left ventricle for tensioning of the suture. A second suture lock is advanced over the final suture tail once the suture tension is adjusted by the user.

FIG. 10 illustrates an embodiment in which a catheter delivered suture line 60 can be pierced through the mitral leaflet 25 with a strain relief 52 on the ventricular side of the mitral leaflet 25 and a suture lock 62 advanced to the atrial side of the mitral leaflet to secure the suture tail, as described with respect to FIG. 9. The other end of the suture tail extends from the catheter handle through the catheter 100 traversing about the distal anchor 32 located in the bottom of the left ventricle for tensioning of the suture. A second suture lock 63 can be advanced over the final suture tail and locked in position on the final suture tail once the suture tension is adjusted by the user. The second suture lock 62 may be configured (e.g., sized and/or shaped) to prevent the suture lock 62 from being pulled through the distal anchor 32 when under tension.

Figure 11:
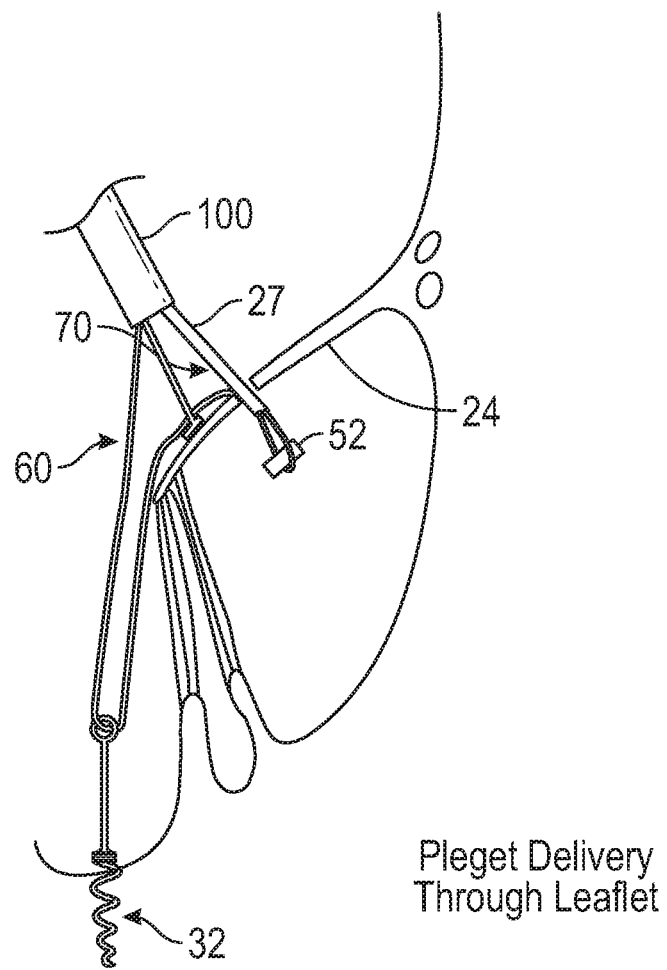
FIG. 11 illustrates a catheter delivered suture loop pierced through the mitral leaflet with a strain relief on the ventricular side of the mitral leaflet in a looped configuration about the strain relief and a distal anchor in the bottom of the left ventricle with the final suture tension adjustment being held with a suture lock advanced over the suture tails. Holding the leaflet steady and counteracting the piercing force of the strain relief is illustrated a cryo-catheter sticking to the mitral leaflet.

FIG. 11 illustrates an embodiment in which a catheter delivered suture loop 60 can be pierced with a piercing element 27 (e.g., a needle) through the mitral leaflet 24 with a strain relief 52 on the ventricular side of the mitral leaflet 24 in a looped configuration about the strain relief 52 and a distal anchor 32 in the bottom of the left ventricle with the final suture tension adjustment being held with a suture lock advanced over the suture tails. The configuration of this embodiment may be similar to that illustrated in FIGS. 8-10. Holding the leaflet steady and counteracting the piercing force of the strain relief can be accomplished using a cryo-catheter 70 sticking to the mitral leaflet 24. The cryo-catheter 70 can be delivered through the same catheter 100 or through a separate catheter. The cryo-catheter may transiently apply a cooling effect to the mitral leaflet 24 causing tissue of the leaflet 24 to temporarily adhere to the catheter. Other retention devices may be used as well, alone or in combination, including suction devices, tissue-grasping devices, additional piercing devices, etc. Providing a retention force to the leaflet 24 may advantageously assist in applying a counter force to the leaflet during insertion of the piercing element 27.

Figure 12:
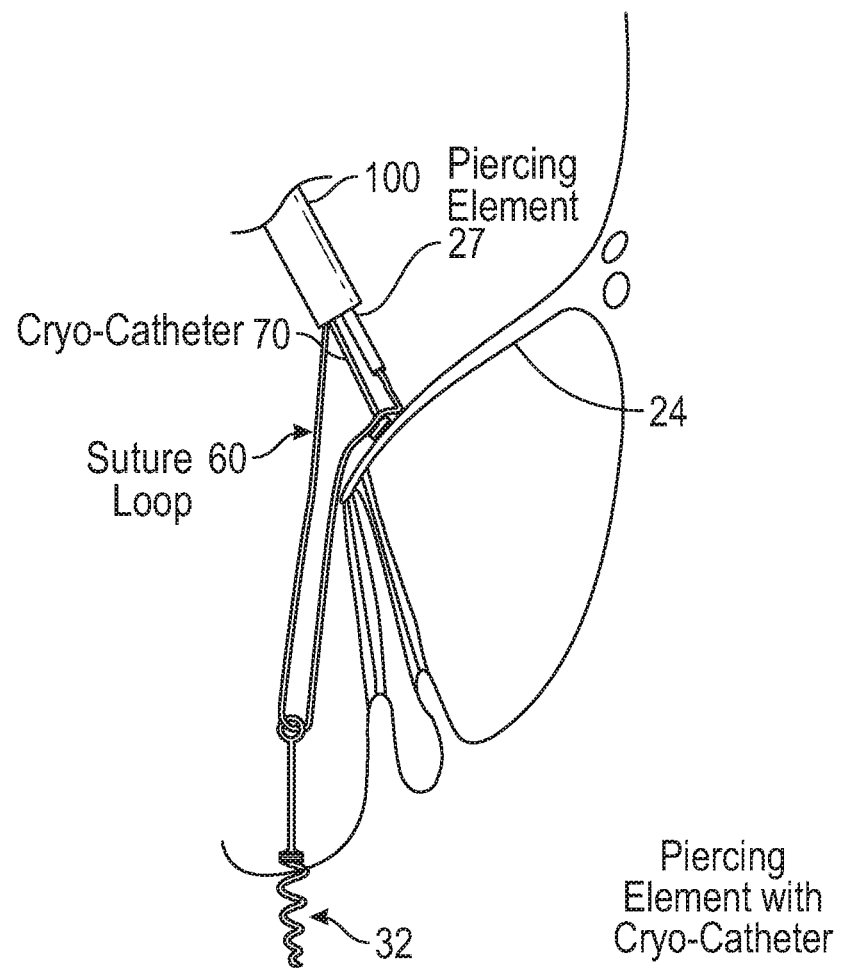
FIG. 12 illustrates a catheter delivered suture loop pierced through the mitral leaflet with a strain relief to be delivered on the ventricular side of the mitral leaflet in a looped configuration about the strain relief and a distal anchor in the bottom of the left ventricle with the final suture tension adjustment being held with a suture lock advanced over the suture tails. Holding the leaflet steady and counteracting the piercing force of the strain relief is illustrated a cryo-catheter sticking to the mitral leaflet.

FIG. 12 illustrates a catheter delivered suture loop 60 pierced through the mitral leaflet 24 with a strain relief to be delivered on the ventricular side of the mitral leaflet in a looped configuration about the strain relief and a distal anchor 32 in the bottom of the left ventricle with the final suture tension adjustment being held with a suture lock advanced over the suture tails. Holding the leaflet steady and counteracting the piercing force of the strain relief is illustrated a cryo-catheter 70 sticking to the mitral leaflet. The embodiment illustrated in FIG. 12 may be similar to the embodiment illustrated in FIG. 11, with the piercing element 27 retracted from the tissue.

Figure 13:
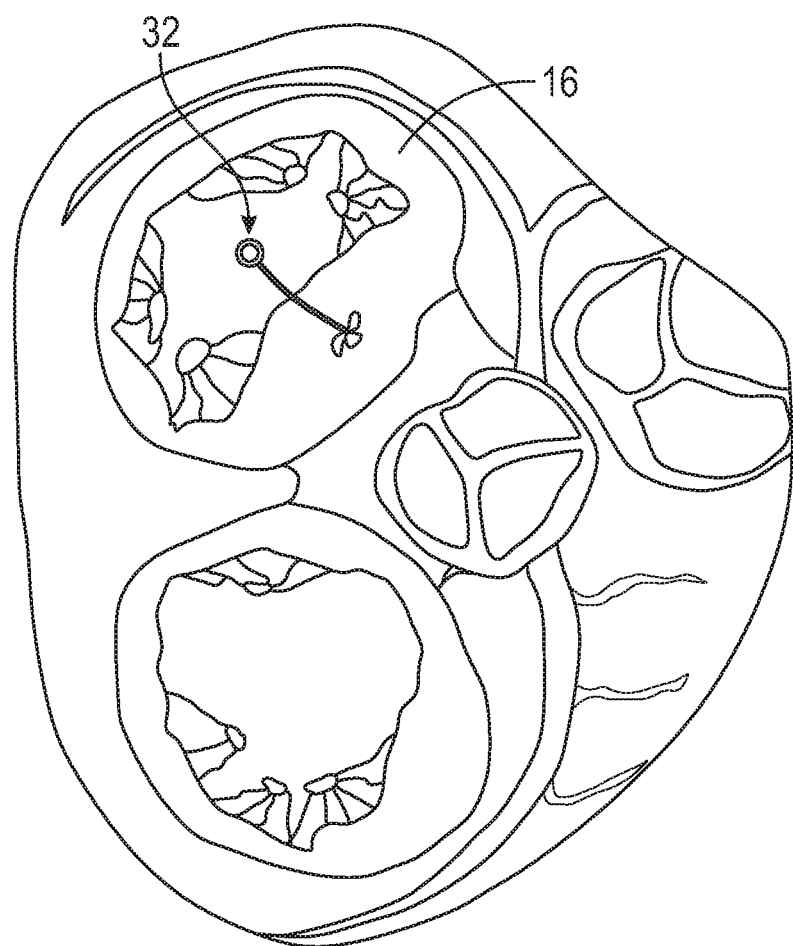
FIG. 13 illustrates a view from the atrial side showing where the mitral annulus is pierced and where the distal anchor is located with respect to the native papillary muscles.
Figure 14:
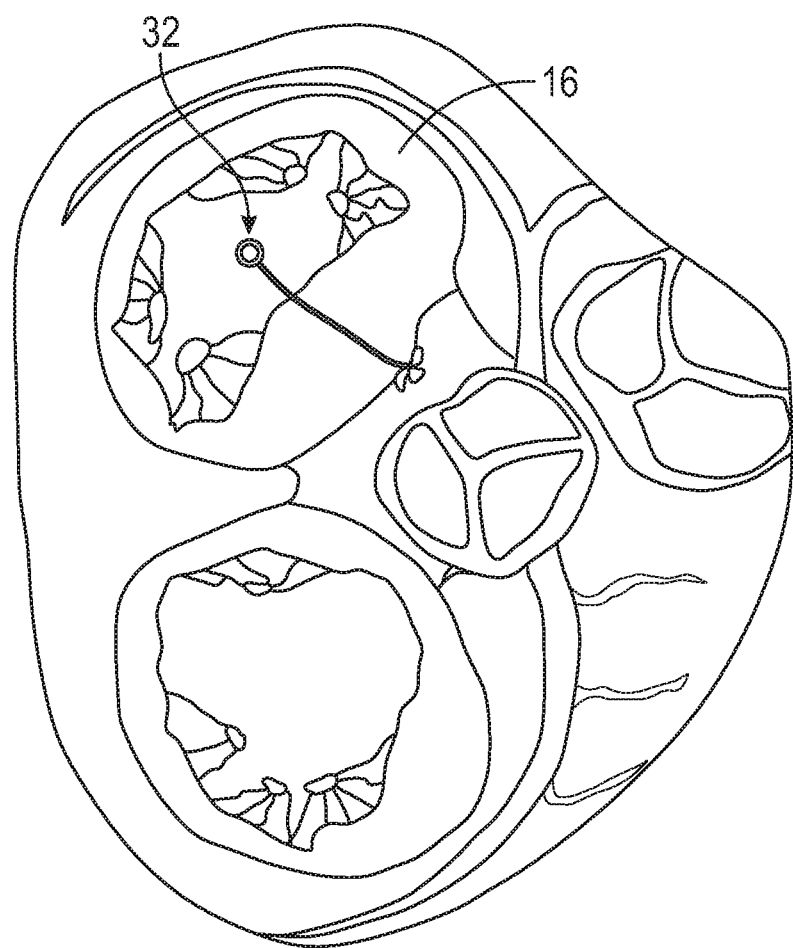
FIG. 14 illustrates a view from the atrial side showing where the mitral annulus is pierced and where the distal anchor is located with respect to the native papillary muscles.

FIGS. 13 and 14 illustrates a views from the atrial side showing where according to certain embodiments the mitral annulus 16 is pierced and where the distal anchor 32 is located with respect to the native papillary muscles. In some embodiments, either the anterior or posterior leaflet or the annular tissue adjacent thereto may be pierced. The positioning of the piercing and installation of a strain relief or leaflet anchor may be used to affect the amount of tension exerted on the leaflet.

Figure 15:
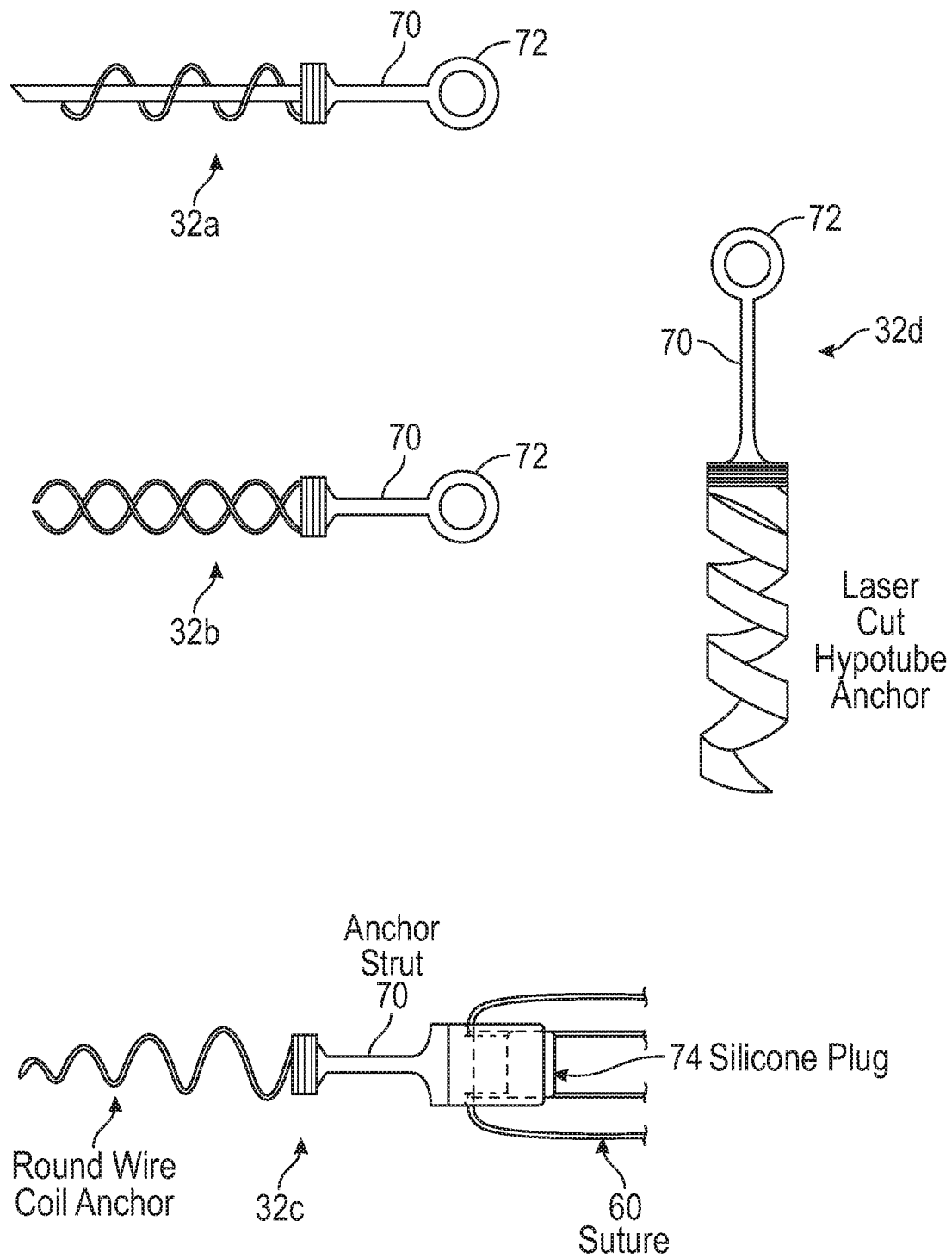
FIG. 15 illustrates a variety of anchors for attachment into the apex of the left ventricle including coiled round wire and laser cut hypo-tube with vertical risers adjusting the connection point closer to the height of the papillary muscles to better simulate the correct angle and match the new chordal connections.

FIG. 15 illustrates a variety of anchors embodiments 32a, 32b, 32c, 32d, for attachment into the apex of the left ventricle including coiled round wire 32a, 32b, 32c and laser cut hypo-tube 32d with vertical risers 70 adjusting the connection point 72 closer to the height of the papillary muscles to better simulate the correct angle and match the new chordal connections. Anchor 32a comprises a single helical coil extending around the outside of a longitudinally aligned pointed shaft. In some embodiments, the shaft may be excluded. Anchor 32b comprises two helical coils, having substantially the same pitches, extending in opposite directions. In some embodiments, a pointed shaft, such as in 32a, may extend between the coils. Anchor 32c includes a single helical coil that reduces in its outer diameter from the proximal end of the coil to the distal end of the coil. Anchor 32d includes a single coil formed from the laser cut hypo-tube. In some embodiments, the connection point 72 may be a single closed loop. Sutures may be looped through or otherwise attached to the loop. In some embodiments, other types of connections to the suture or other type of chord may be used. The anchor 32c includes a riser 70 in the form of a strut and the connection point 72 that can receive the suture 60, which can be secured within the connection point 72 by a silicone plug 74. Any suitable material may be used for the plug. The connection point 72 may have a channel configured (e.g., sized and shaped) for receiving the plug 74. The connector may include one or more apertures extending through a sidewall of the channel for allowing a suture to pass through. The plug 74 may frictionally engage the channel. The one or more sutures may extend through the channel and through an aperture in the sidewall as shown in FIG. 15. The suture may freely slide through the aperture during installation when the plug 74 is absent, allowing adjustment of the length of the suture and the tension in the suture. The plug 74 may be inserted into the channel and form a tight frictional fit with the channel. The plug 74 may frictionally secure the one or more sutures between an outer surface of the plug 74 and an inner surface of the sidewall, thereby effectively locking the suture in place with respect to the anchor 32*c*. The plug 74 may be installed after adjusting the length and tension of the one or more sutures. In other embodiments, the suture may extend through a loop a distal end of the channel, allowing the suture to slide there through. Proximal and distal ends of the suture may extend through the proximal opening of the channel. The plug 74 may frictionally secure the suture as described above and preventing further sliding of the suture with respect to the anchor 32*d*. The various features of the anchors 32*a*-32*d* disclosed herein may be employed in any suitable combination.

Figure 16:
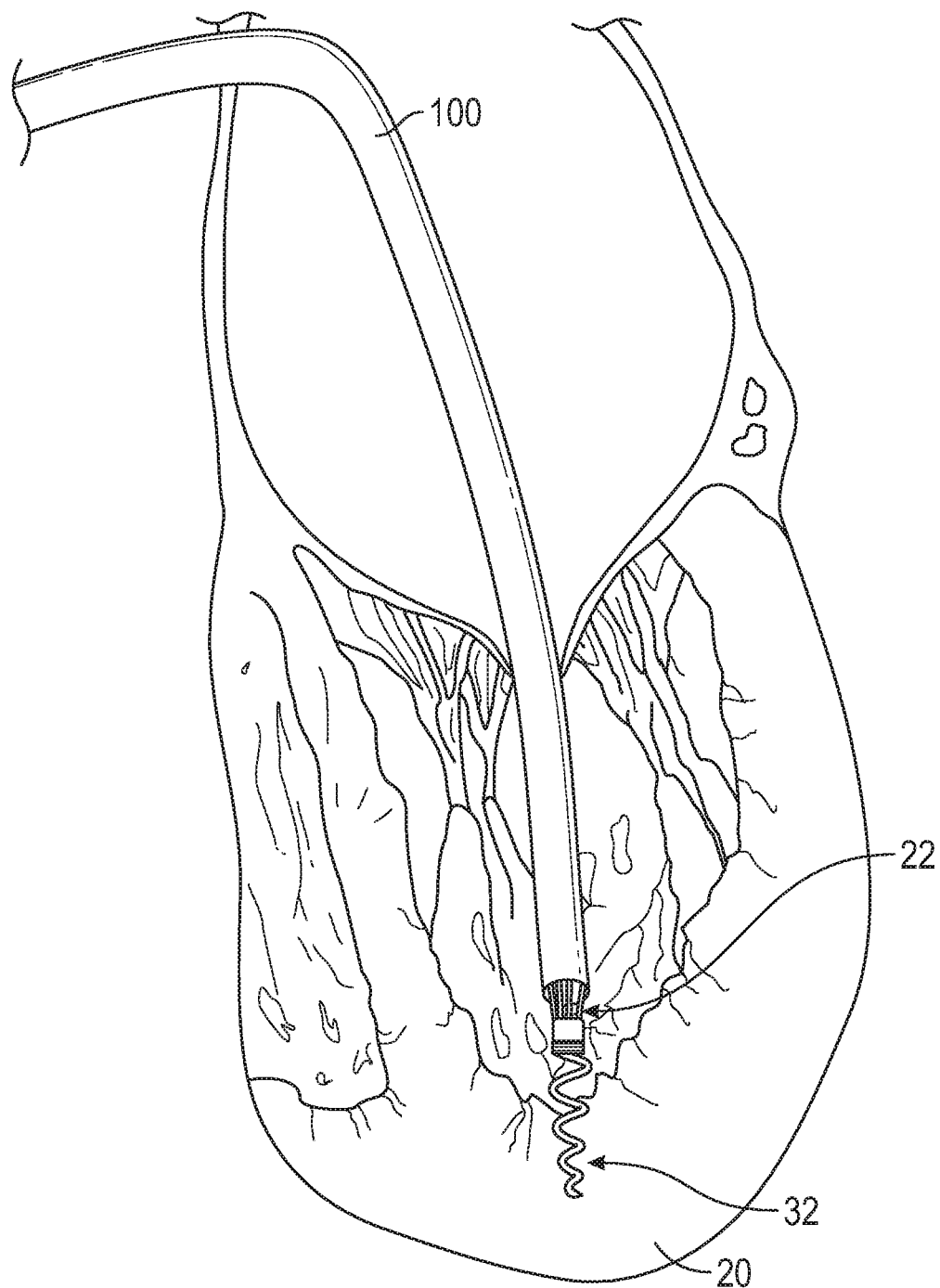
FIG. 16 illustrates a trans-septal catheter delivering an anchor in the apex of the left ventricle with a plurality of replacement chords attached and extending out the handle of the catheter.
Figure 17:
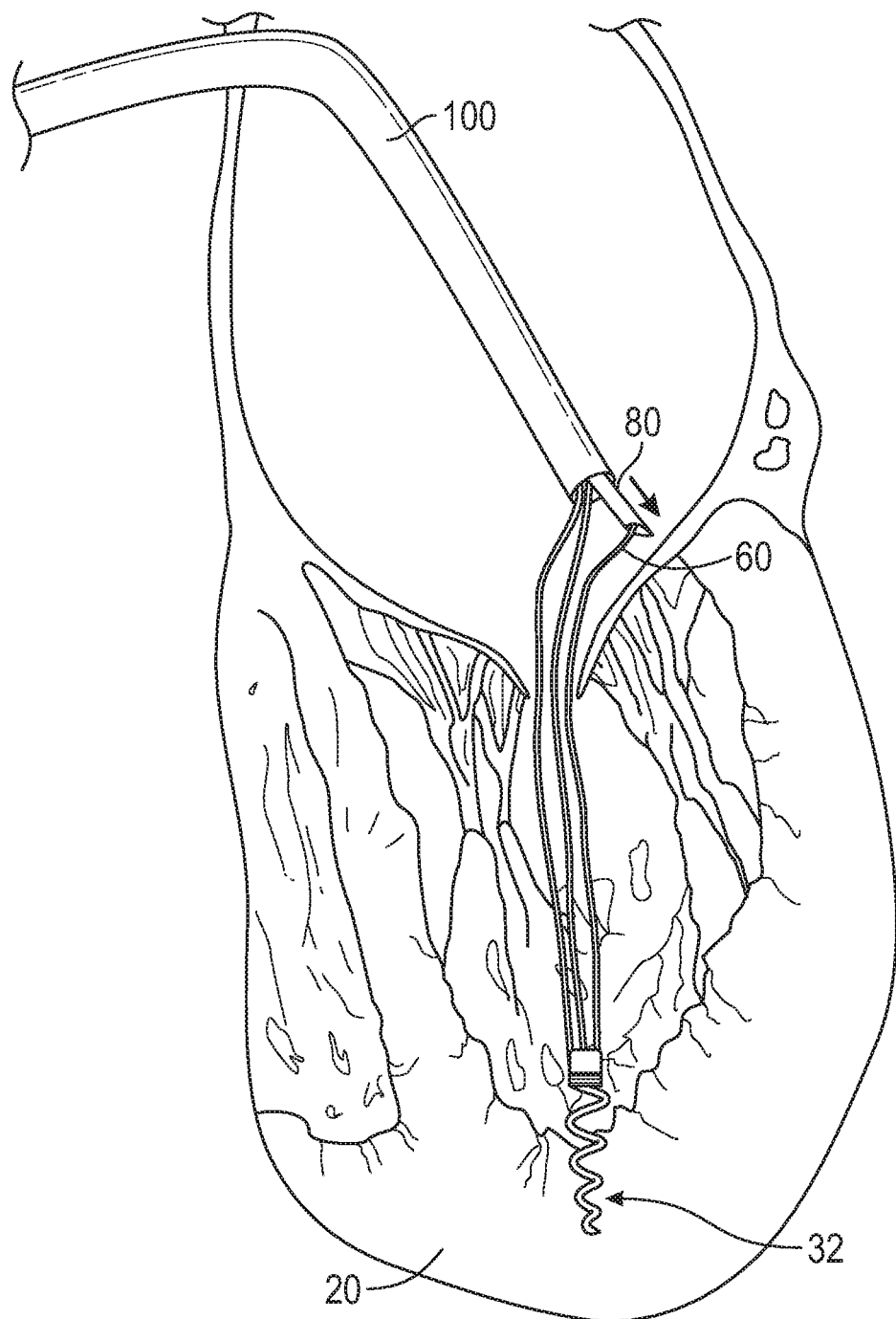
FIG. 17 illustrates a trans-septal catheter delivering a piercing tool through the mitral leaflet to deliver a strain relief anchor connected to a suture loop.
Figure 18:
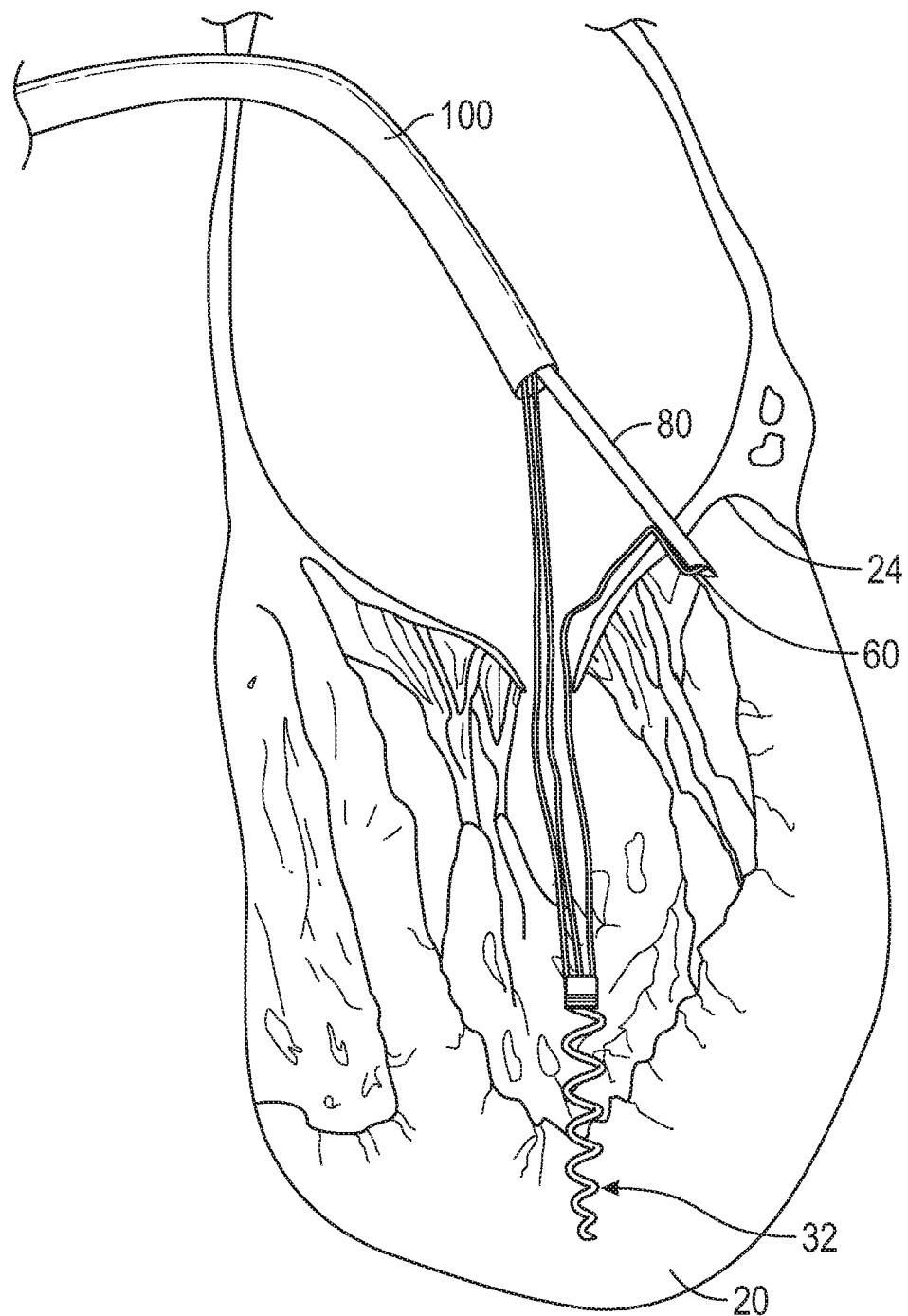
FIG. 18 illustrates a trans-septal catheter delivering a suture loop through the mitral leaflet piercing through the leaflet with the suture loop.
Figure 19:
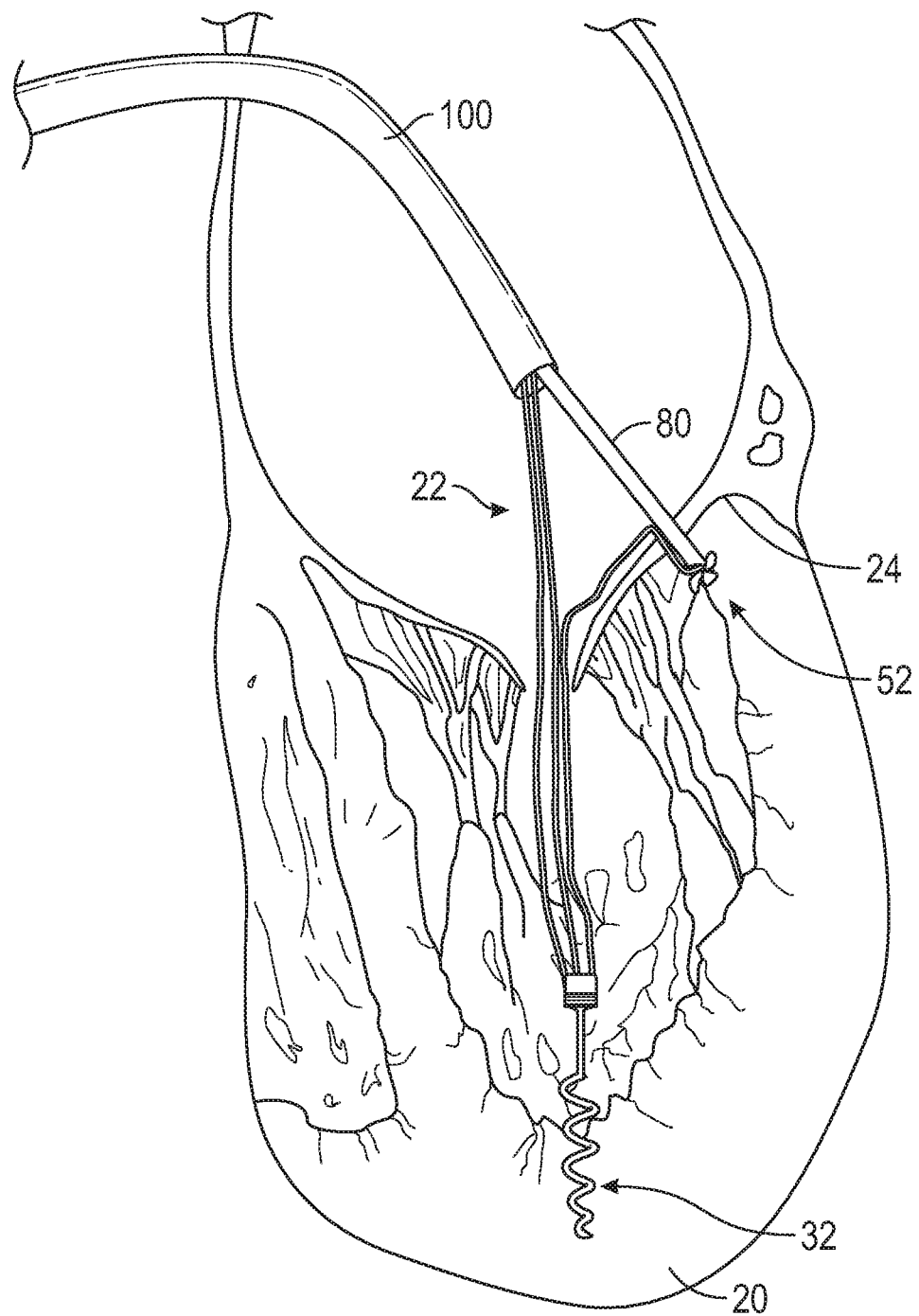
FIG. 19 illustrates a trans-septal catheter delivering the strain relief to the ventricle side of the mitral leaflet exposing it for delivery through or with the piercing tool
Figure 20:
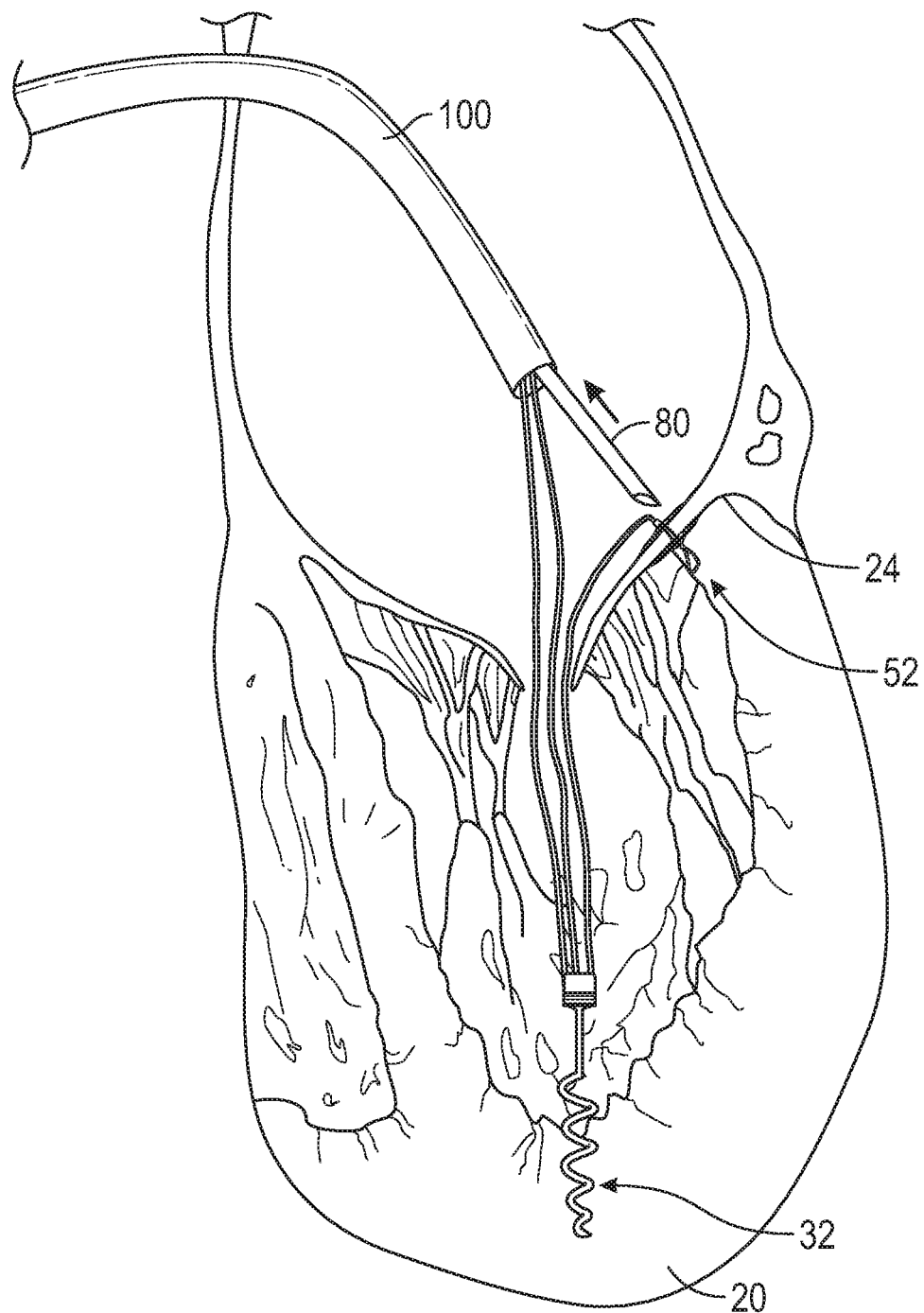
FIG. 20 illustrates a trans-septal catheter delivering the strain relief and the piercing tool being withdrawn for the mitral leaflet.
Figure 21:
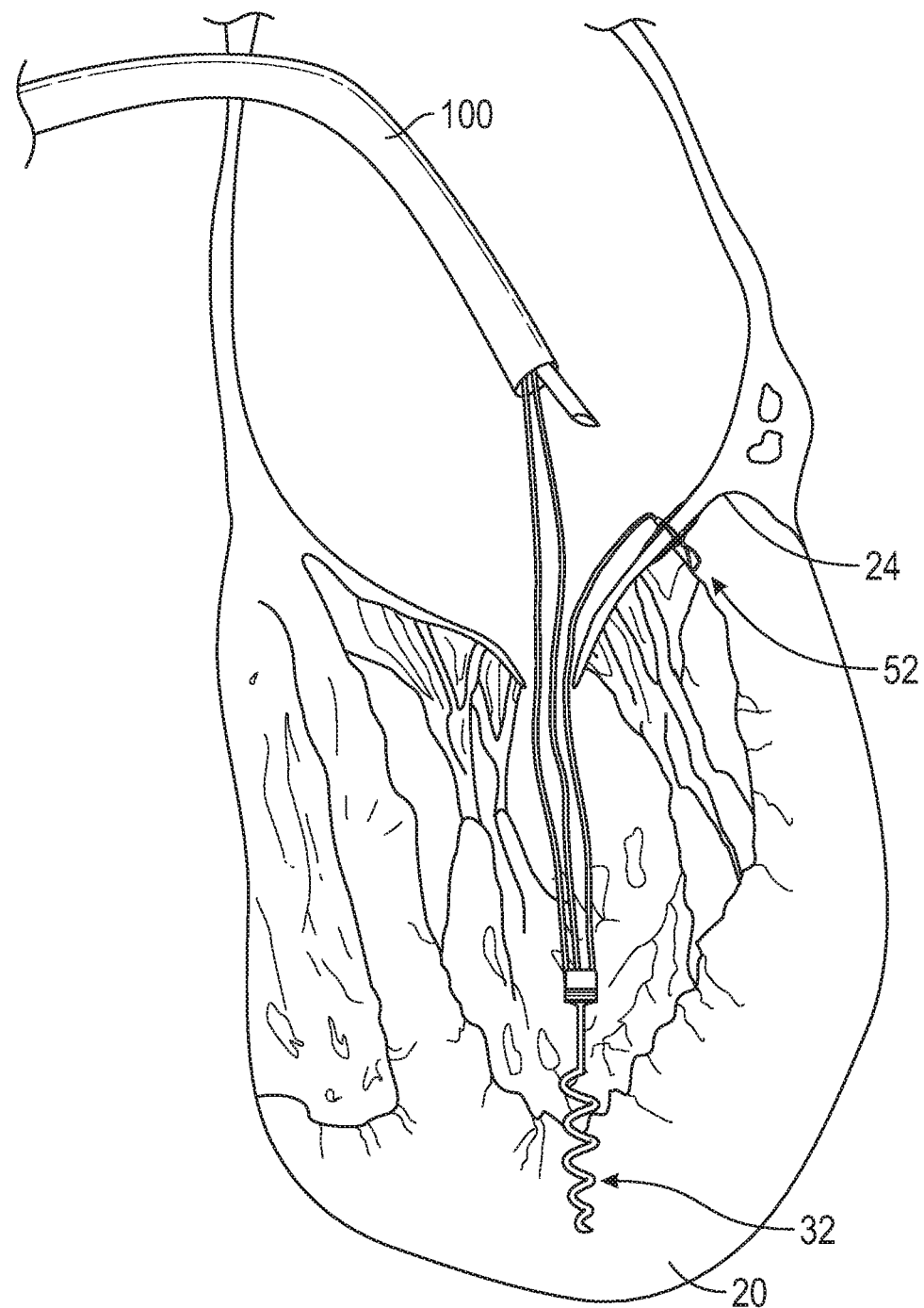
FIG. 21 illustrates a trans-septal catheter delivering the strain relief with the connection to the distal anchor and the suture loop extending back out the catheter handle.
Figure 22:
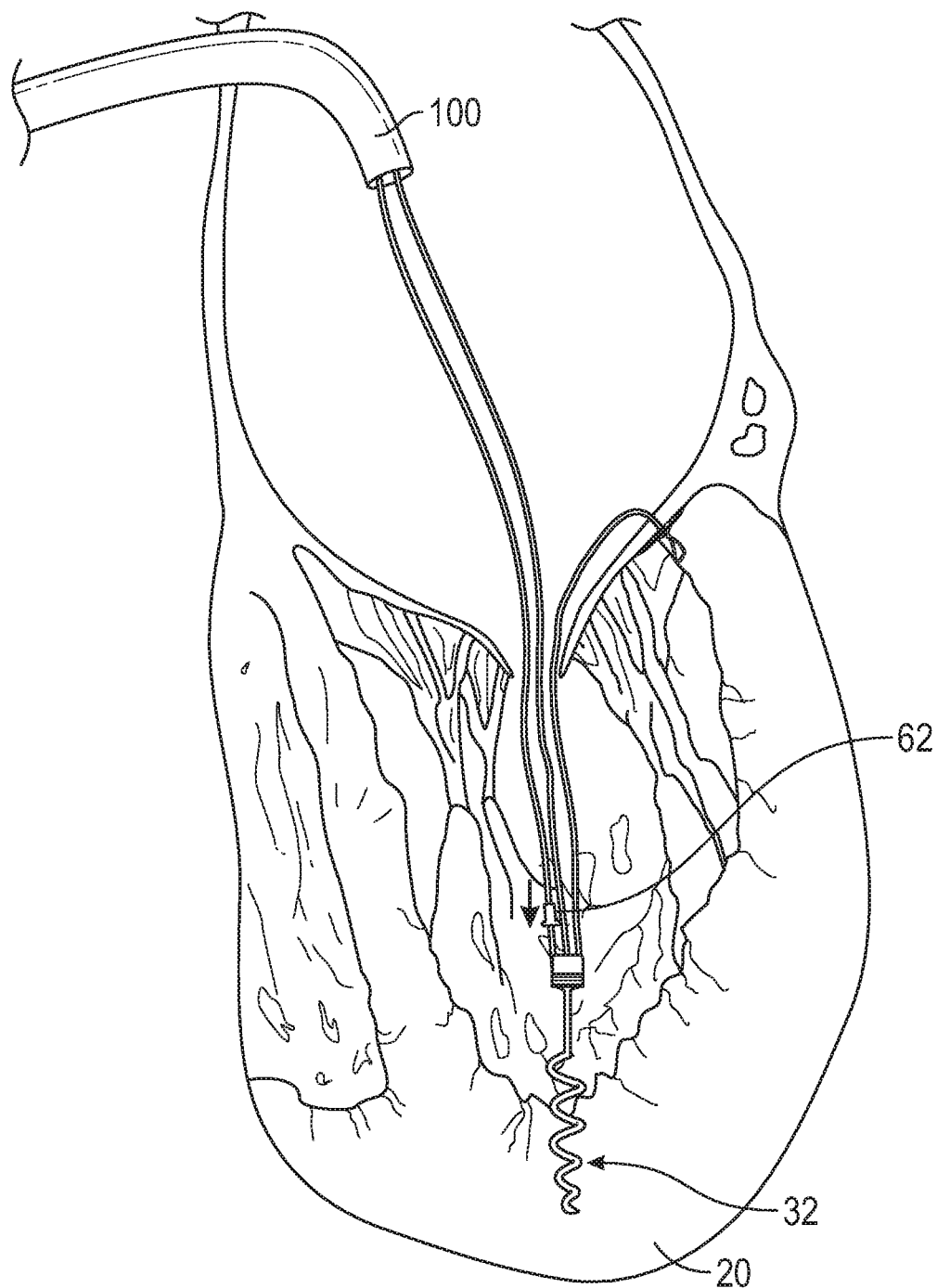
FIG. 22 illustrates a trans-septal catheter delivering a suture lock to the distal anchor being advanced over the suture tail while tension is applied from the proximal end of the suture back our the catheter handle to adjust the position and tension of the final implant suture connected now to the mitral leaflet and the distal apex anchor.

FIGS. 16-22 illustrate another method according to certain embodiments. FIG. 16 illustrates a trans-septal catheter delivering an anchor 32 in the apex 20 of the left ventricle with a plurality of replacement chords 22 attached and extending out the handle of the catheter 100. FIG. 17 illustrates the trans-septal catheter 100 of FIG. 16 delivering a piercing tool 80 through the mitral leaflet 24 to deliver a strain relief anchor connected to a suture loop 60. FIG. 18 illustrates the trans-septal catheter 100 delivering a suture loop 60 through the mitral leaflet 24 piercing through the leaflet 24 with the suture loop 60. FIG. 19 illustrates the trans-septal catheter 100 delivering the strain relief 52 to the ventricle side of the mitral leaflet 24 exposing it for delivery through or with the piercing tool 80. In some embodiments, the strain relief 52 may self-expand upon exposure, as described elsewhere herein. FIG. 20 illustrates the trans-septal catheter delivering the strain relief 52 and the piercing tool 80 being withdrawn from the mitral leaflet 24. FIG. 20 shows an embodiment in which two strain reliefs are positioned on opposite sides of the mitral leaflet 24. The leaflet may be sandwiched between atrial-side and ventricular-side strain reliefs. The atrial-side strain relief may be advanced over the suture after the ventricular-side strain relief 52 is positioned in place and tension applied to the suture to put the ventricular-side strain relief 52 into flush contact with the leaflet 24. The atrial side strain relief may be configured to be locked or secured to the suture to prevent slack from generating between the strain reliefs, which could interfere with the contact between the strain reliefs and the leaflet 24 tissue and take pressure off of the strain reliefs. In some embodiments, a suture lock may be advanced behind the atrial-side strain relief and force the atrial-side strain relief into flush contact with the leaflet 24 tissue. In some instances, using dual strain reliefs may reduce the strain on the puncture point through the leaflet 24 and mitigate any damage to the leaflet 24 tissue. FIG. 21 illustrates the trans-septal catheter 100 delivering the strain relief 52 with the connection to the distal anchor 32 and the suture loop 60 extending back out the catheter handle FIG. 22 illustrates the trans-septal catheter delivering a suture lock 62 to the distal anchor 32. The suture lock 22 is being advanced over the suture tail while tension is applied from the proximal end of the suture back out through the catheter handle to adjust the position and tension of the final implant suture, which is connected now to the mitral leaflet 24 and the distal apex anchor 32.

Figure 23:
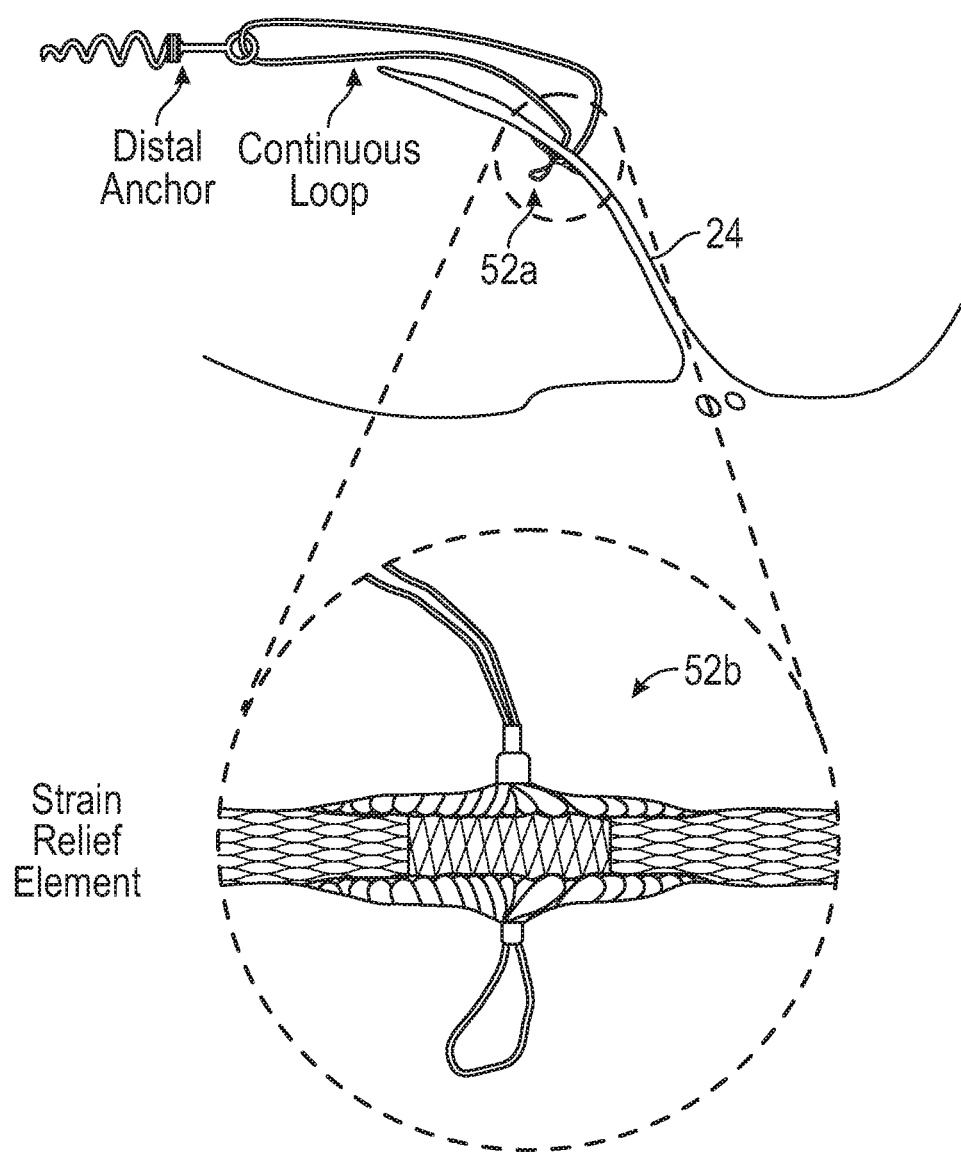
FIG. 23 illustrates a final suture loop anchoring the distal apex anchor to the mitral leaflet noting the mitral anchor can be single sided flange or a single side as shown in the unexploded view.

FIG. 23 illustrates an embodiment in its final position, in which a continuous suture loop anchors the distal apex anchor 32 to a strain relief element 52 on the mitral leaflet 24. In some embodiments, the continuous loop may be formed by applying suture locks to tails of the looped suture. Any other suitable means for forming a continuous loop suture may be used as well. In some embodiments, the mitral leaflet anchor or strain relief element 52 can be double-sided (e.g., comprise a double-sided flange 52*b*), as shown in the exploded view, or a singlesided flange 52*a* as shown in the unexploded view. The double-sided flange 52*b* may comprise expandable elements (e.g., expandable flanges) configured to be positioned on opposite sides of the mitral leaflet tissue. In some embodiments, the two opposing flanges may be fixedly coupled to each other through an intermediate element that traverses the leaflet 24 puncture. The flanges may comprises a plurality of strain relief elements (e.g., flexible/deformable loops) configured to distribute the strain across a larger surface area of the leaflet 24.

Figure 24:
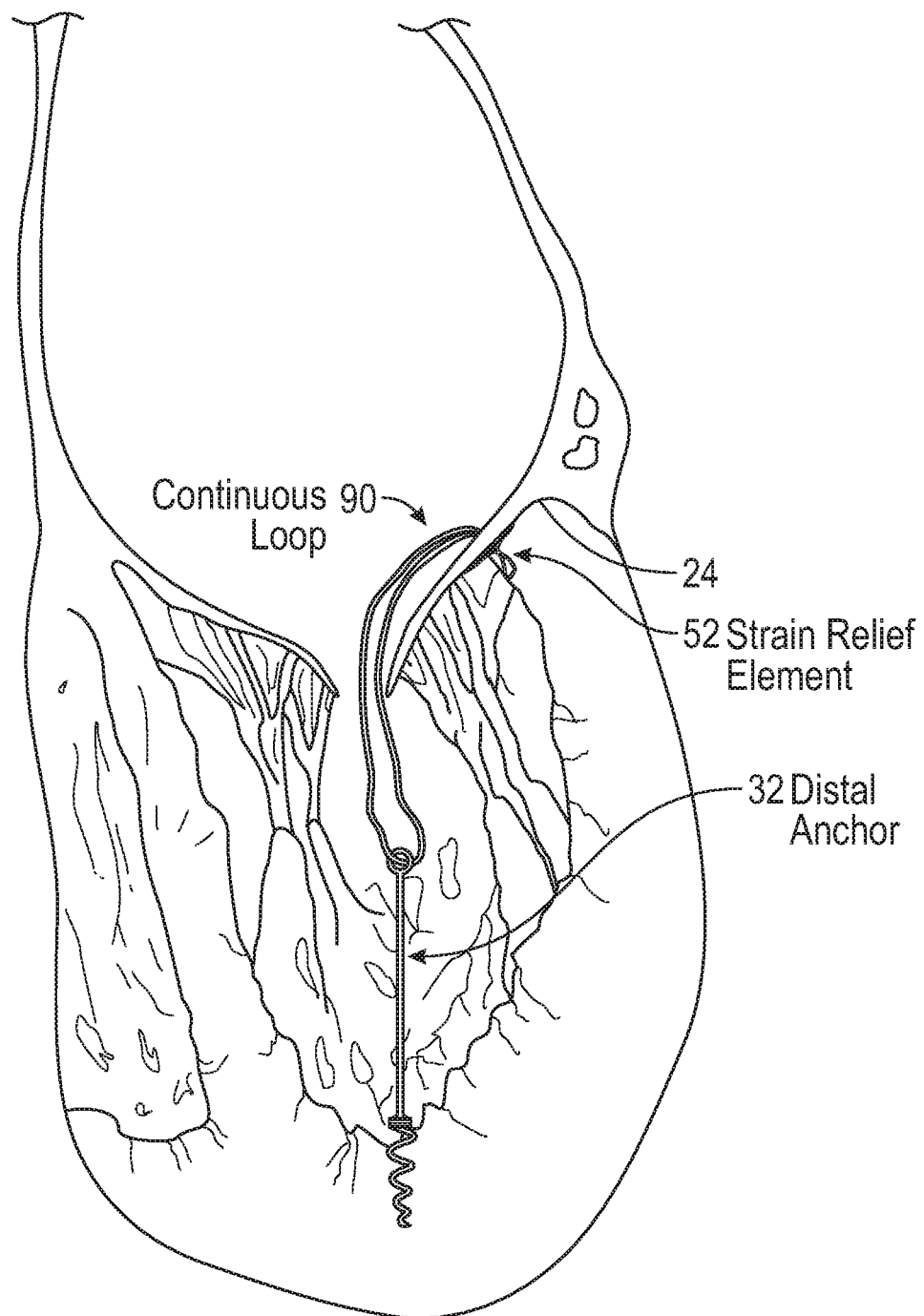
FIG. 24 illustrates a continuous loop anchor delivered in its final position with a distal apex anchor and a strain relief element on the mitral leaflet.

FIG. 24 illustrates an embodiment in which a continuous loop 90 is delivered in its final position with a distal apex anchor 32 and a strain relief element 52 on the mitral leaflet 24. The embodiment may be similar to that illustrated in FIG. 23.

Figure 25:
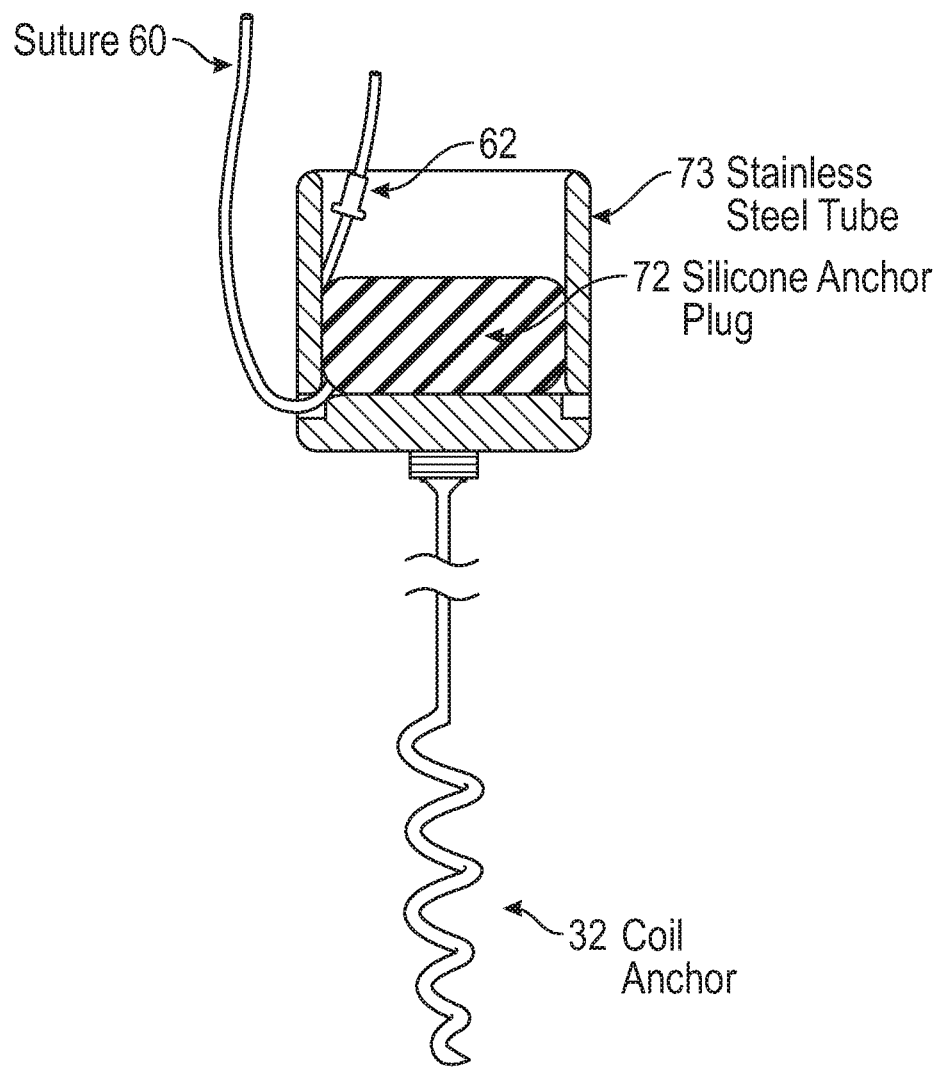
FIG. 25 illustrates an example of a distal apex anchor constructed of a stainless tube and a silicone anchor plug//to limit the suture movement before delivery of the suture lock for final positioning. The materials can be varied and changed to accommodate size and material enhancements.

FIG. 25 illustrates an example of a distal apex anchor 32 constructed of a stainless steel tube 73 and a silicone anchor plug 72 configured to limit the suture movement before delivery of the suture lock 62 for final positioning. In some embodiments, the plug 72 may be used as a temporary suture lock. In other embodiments, the plug may serve as a temporary suture lock in addition to or alternatively to suture lock 62, which is advanced over the suture. Where the plug 72 is temporarily used, it may be removed prior to completion of the implant installation. The materials can be varied and changed to accommodate size and/or material enhancements. In some implementations, the anchor 32 may be the same or similar to the anchor 32*c* illustrated in FIG. 15.

Figure 26:
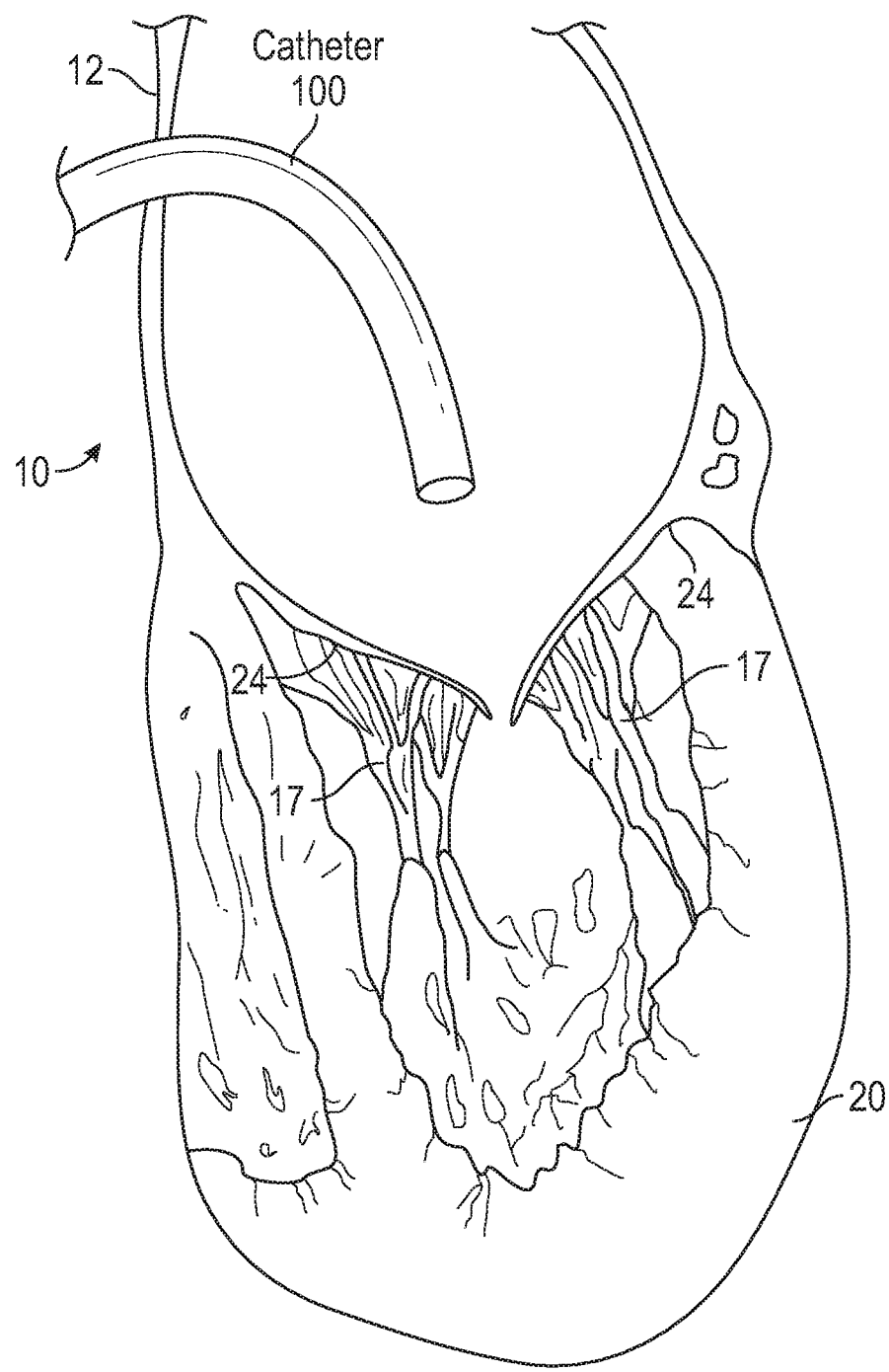
FIG. 26 illustrates a catheter penetrating the septum from the right atrial and the left atrium.

FIGS. 26-34 illustrate an embodiment in which order of the placement distal apex anchor 32 can be modified. As shown, FIG. 26 shows a catheter 100 penetrating the septum 12 from the right atrial and the left atrium 14.

Figure 27:
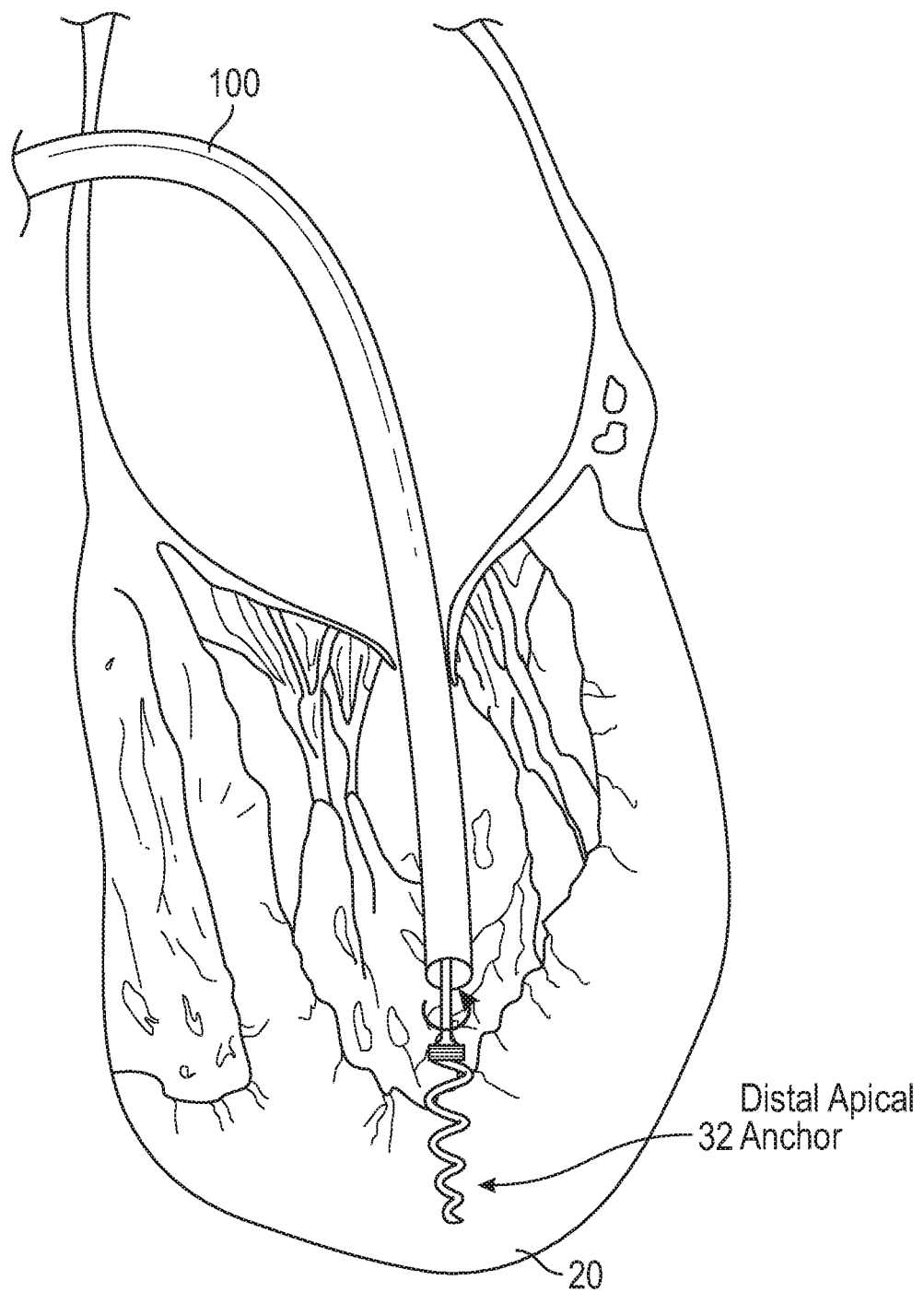
FIG. 27 illustrates an anchor being rotated into the left ventricle.

FIG. 27 illustrates an anchor 32 being rotated into the apex of the left ventricle. The anchor 32 may be rotated clockwise or counterclockwise depending on the configuration of the anchor. The anchor 32 may be rotated by a delivery instrument (e.g., a rotational driver) that can be inserted through the catheter 100, as described elsewhere herein. In addition, while the illustrated embodiment shows the anchor 32 being rotated into the apex of the left ventricle in modified embodiments the anchor 32 can be secured to other locations within the left ventricle. For example, as will be described in more detail below, embodiments of the methods and devices described herein can also be utilized in arrangements in which the anchor 32 is positioned in left ventricle between the papillary muscles. Such an arrangement can advantageously align the suture extending the anchor 32 and the mitral leaflet 24 with one or more of the chordae tendinae extending from the anchored mitral valve leaflet 24.

Figure 28:
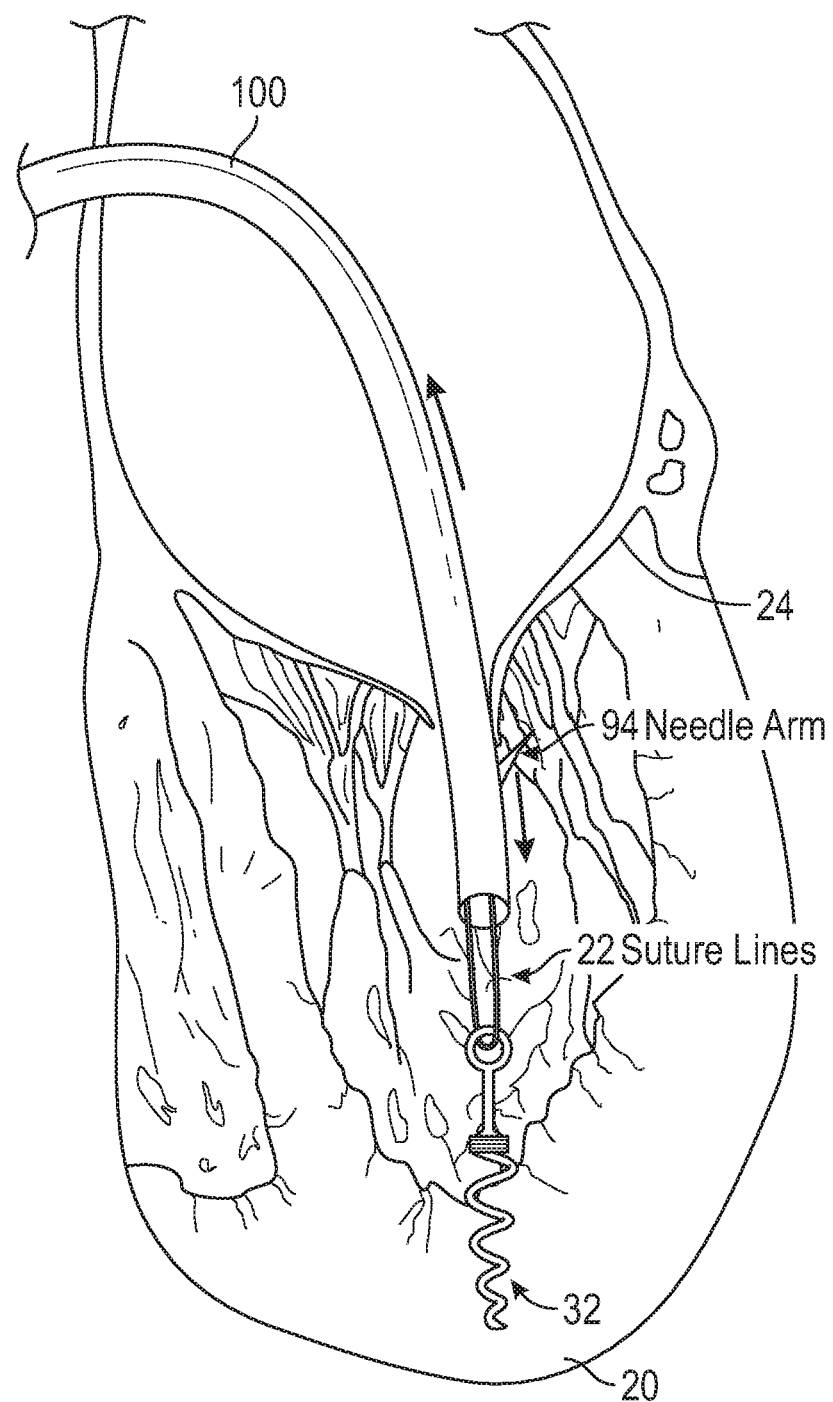
FIG. 28 illustrates the distal apical anchor in place with the suture lines attached and extending back through the catheter and an extension arm exposed to capture the mitral leaflet with a needle to be fired when properly positioned on the leaflet.

FIG. 28 illustrates the distal apical anchor 32 in place with the suture lines 22 attached and extending back through the catheter 100 to a proximal end of the delivery device outside of the body. The suture can be looped through the anchor 32 as described elsewhere herein. An extension arm 94 of the catheter 100 can be exposed on a lateral side of the catheter, somewhat proximal to the distal end of the catheter 100. The extension arm 94 may be angled to extend in a proximal direction from the side of the catheter 100. The extension arm may be configured to capture the mitral leaflet 24, such as on the ventricular side of the leaflet 24. The extension arm 94 may have a pointed tip or may comprise a needle or allow passage of a needle through the catheter 100 and the extension arm 94. The leaflet 24 may be engaged with a needle configured to be fired when properly positioned on the leaflet 24. In some embodiments the extension arm may be formed on a separate catheter which is configured to extend through and be independently distally advanceable and proximally retractable through the catheter 100.

Figure 29:
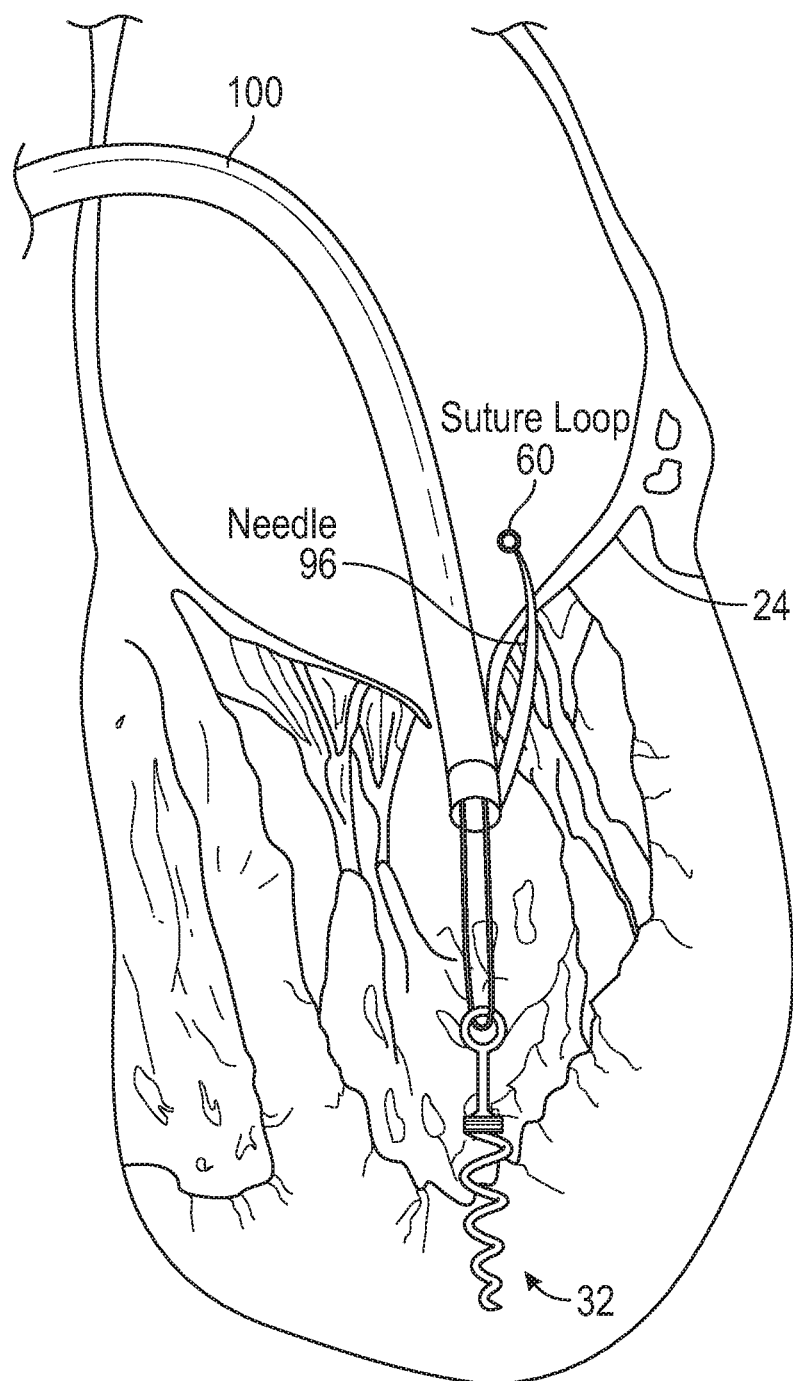
FIG. 29 illustrates the extension arm in contact with the mitral leaflet and the needle connected to a suture loop penetrating the leaflet to expose a suture loop on the atrial side of the mitral leaflet.

FIG. 29 illustrates the extension arm 94 in contact with the mitral leaflet 24 and the needle 96 connected to a suture loop 60 penetrating the leaflet 24 to expose a suture loop 60 on the atrial side of the mitral leaflet 24. In some embodiments, the suture loop may be formed from one tail of the suture extending through the distal anchor 32. The other end may extend proximally through the delivery catheter to a proximal end of the delivery catheter 100 and outside the body. In some embodiments, the suture loop 60 may be a ring through which the suture is looped. In some embodiments, the suture loop 60 may be a loop in the suture which is engaged with the needle 96, and the needle 96 may be configured to retain the suture loop 60 and prevent the suture loop from being retracted proximally through the needle 96. In some embodiments, a continuous suture may be threaded through the distal anchor 32 such that four strands extend from the distal anchor 32, two of which extend through to the proximal end of the catheter 100 and two of which extend to form the suture loop 60.

Figure 30:
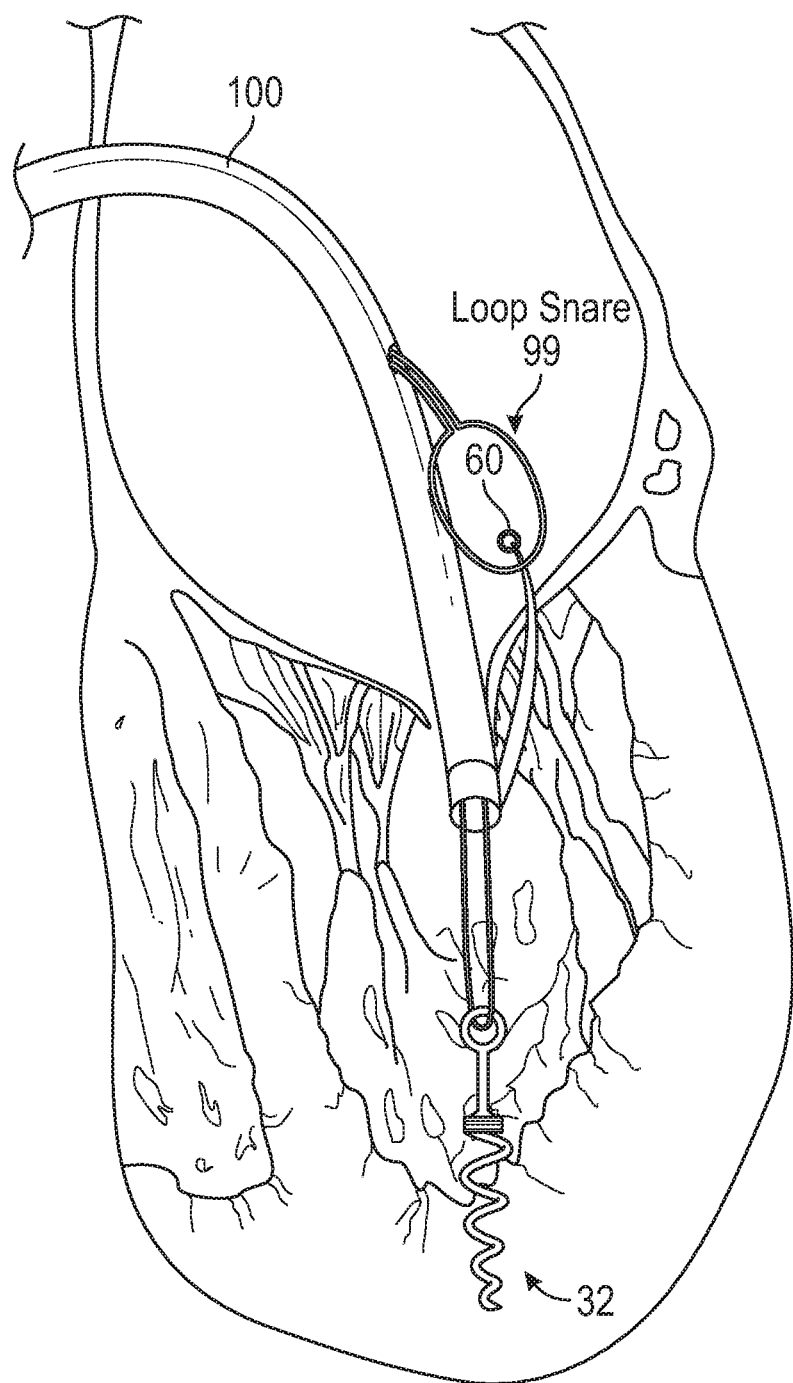
FIG. 30 illustrates the suture loop exposed on the atrial side of the leaflet penetrating through the mitral leaflet to accept a loop-snare for capture of the suture loop and retrieval back through the catheter.

FIG. 30 illustrates the suture loop 60 exposed on the atrial side of the leaflet penetrating through the mitral leaflet to accept a loop-snare 99 for capture of the suture loop 60 and retrieval back through the catheter 100. The loop snare may be delivered through another opening the catheter 100, which is positioned proximally of the extension arm 94. The extension arm 94 and loop snare opening may be positioned on the same lateral side of the catheter 100. The loop snare 99 may be configured to be contracted around the suture loop 60 such that the loop snare 99 may retain the suture loop 60 and retract it proximally into the catheter 100 through the loop snare opening (advancing the suture loop distally through the extension arm 94).

Figure 31:
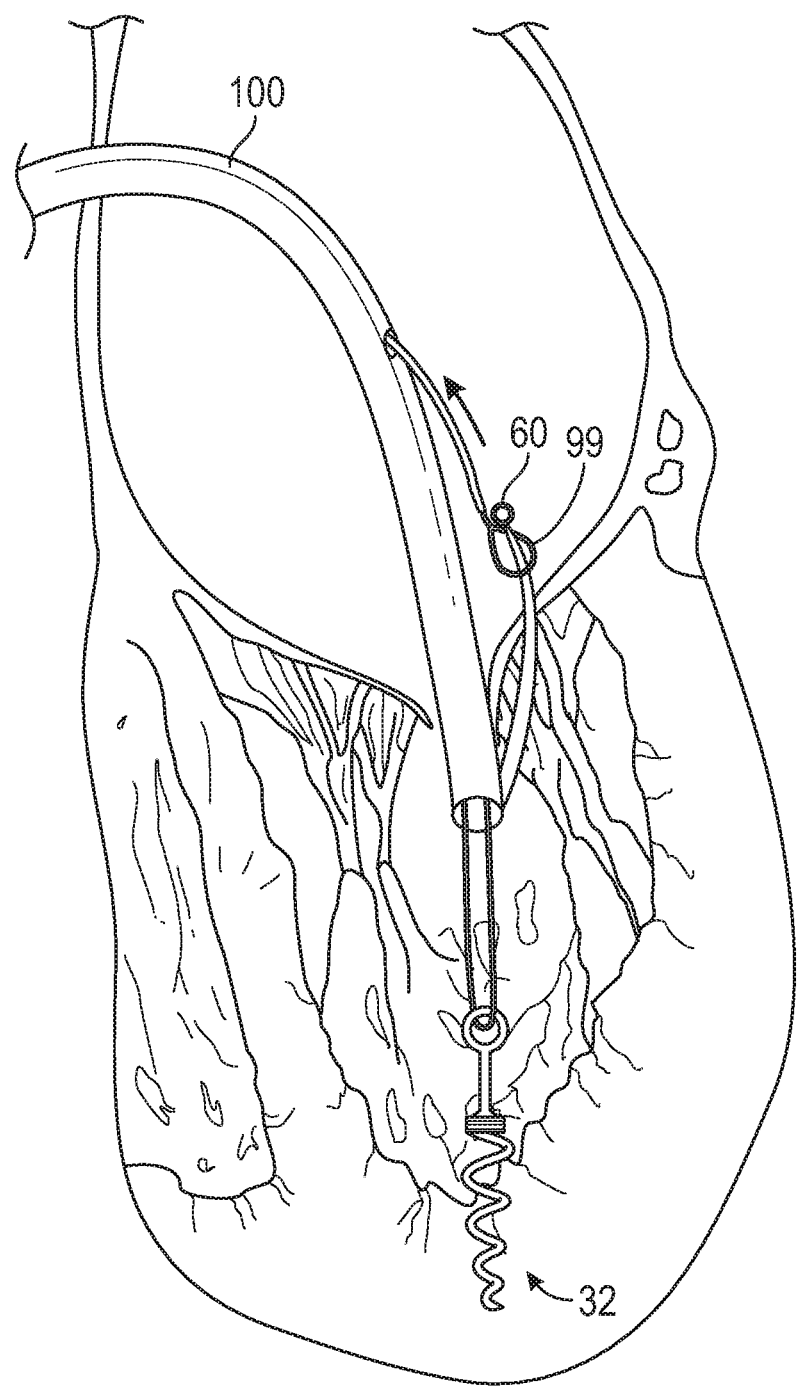
FIG. 31 illustrates the suture loop closed around the suture loop and the suture being withdrawn proximally through the catheter.
Figure 32:
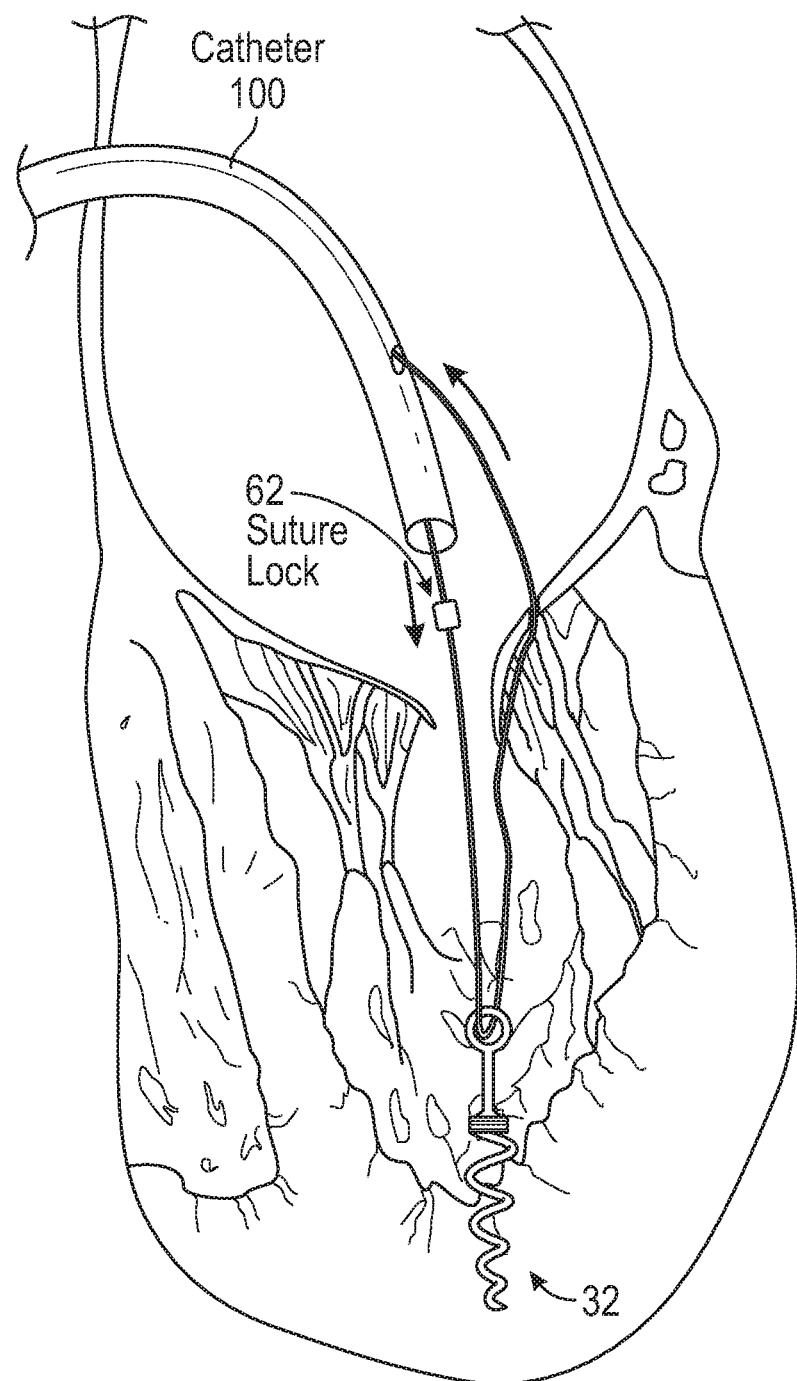
FIG. 32 illustrates the catheter to deliver a suture lock to the backside of the mitral leaflet as the suture is looped around the pathway including the distal apical anchor

FIG. 31 illustrates the suture loop snare 99 closed around the suture loop 60 and the suture being withdrawn proximally through the catheter 100. FIG. 32 illustrates the catheter 100 delivering a suture lock 62 to the backside of the mitral leaflet as the suture is looped around the pathway including the distal apical anchor 32. The suture lock 62 and distal anchor 32 may be configured such that the suture lock 62 may freely pass through the connecting point of the distal anchor 32 to reach the ventricular side of the leaflet 24. For example, the suture lock 62 may be configured to pass through a loop in the distal anchor 32. The extension arm 94 may be retracted prior to or during this step, such that the leaflet 24 is no longer captured by the extension arm 94. In some embodiments, as described elsewhere herein, the extension arm may be formed as part of an internal catheter that is advanced through catheter 100 and can subsequently be withdrawn through catheter 100.

Figure 33:
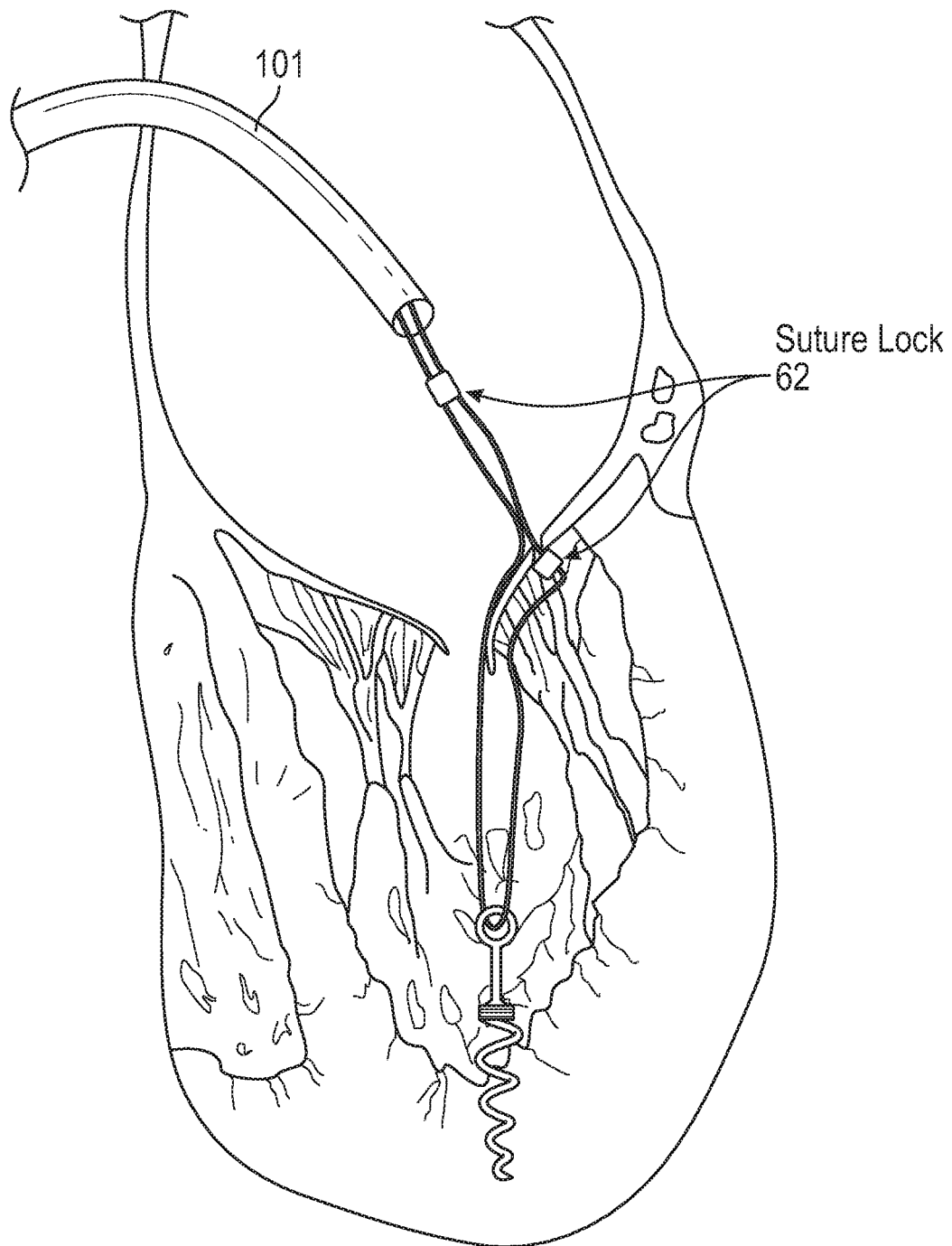
FIG. 33 illustrates a second catheter to contain the suture ends to deliver a suture lock over both leaflets locking the suture together after proper tensioning of the two ends.
Figure 34:
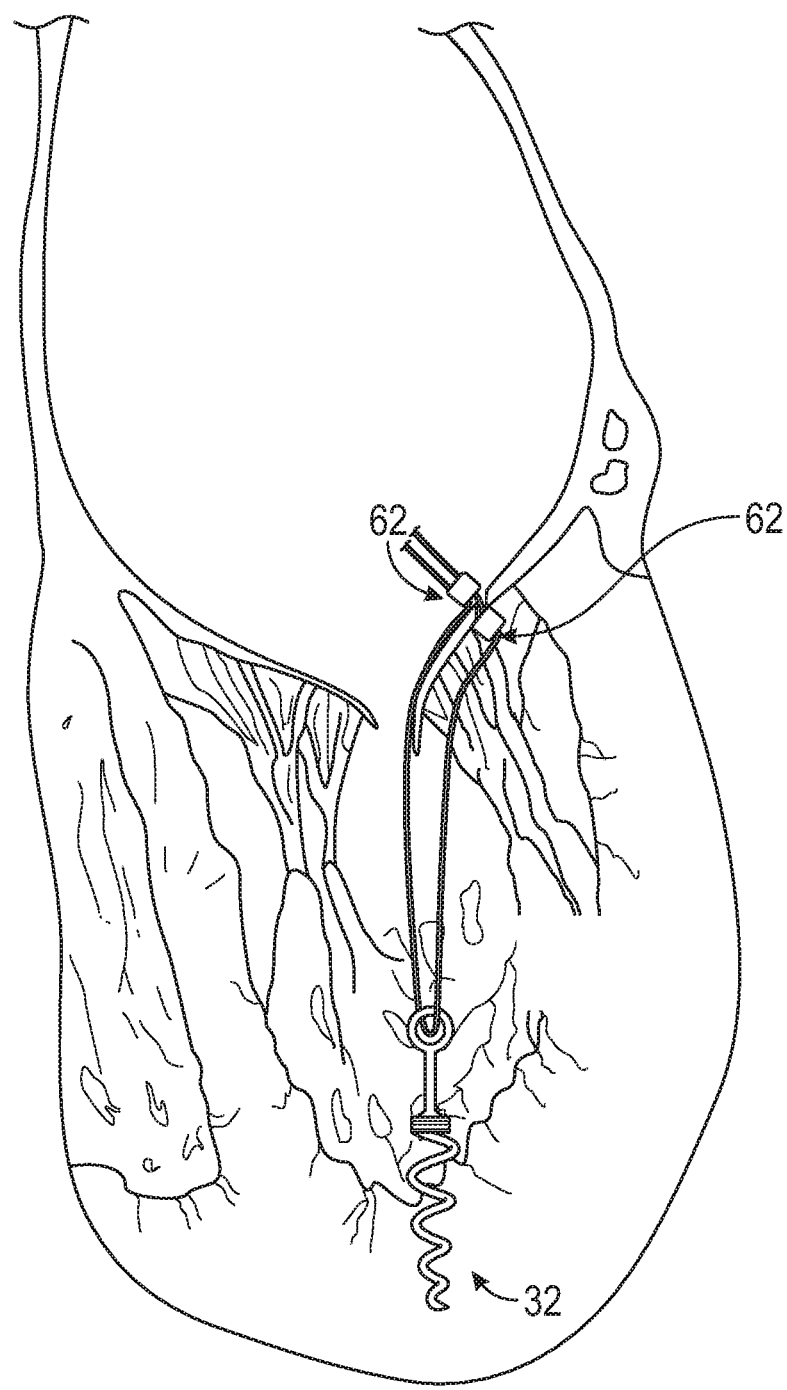
FIG. 34 illustrates the final position of the suture locks in position above and below the mitral leaflet and the suture ends cut to leave a final implant of a distal apical anchor connected to the mitral leaflet.

FIG. 33 illustrates a second catheter 101 to contain the suture ends to deliver a suture lock over both leaflets locking the suture together after proper tensioning of the two ends. Catheter 100 may be withdrawn bringing the suture loop 60 outside of the body, where it may be aligned with the other end of the suture. The second suture lock may be applied over the suture ends and subsequently delivered into the body using the second catheter 101 FIG. 34 illustrates the final position of the suture locks 62 in position above and below the mitral leaflet 35 and the suture ends cut to leave a final implant of a distal apical anchor connected to the mitral leaflet 24. The second suture lock 62 may be positioned in alternative positions as well relative to the leaflet 24, depending on the length of the suture between the two suture locks. Positioning two suture locks on opposite sides of the leaflet 24 may allow the suture locks to serve as strain reliefs. In some embodiments, the first suture lock 62 positioned on the ventricular side of the leaflet 24 may be omitted.

Chordal end termination and suture locking configurations and devices can include one or more of knots, pledgets or other termination techniques to reduce the focal stress at the attachment points. Piercing through annular tissue and leaflets can be achieved via sharpened needle insertion and can be driven via a steerable catheter and core shaft to push, locate and drive the needle through the mitral leaflet. These procedures may be guided under fluoroscopy, echo guidance, or any other suitable visualization or monitoring procedure. Leaflet location and isolation can be achieved by a mechanical technique of grasping or pinching the leaflet or by suction or freeze-grabbing with a cryo-catheter. These techniques would include a cryo-catheter used in ablation procedures to freeze the focal tissue as described, for example, with reference to FIG. 12. These cryoablation-catheters used for atrial fibrillation often attach themselves to the mitral leaflets accidentally and need to be deactivated to release the attached leaflets. This same cryo attachment could be used to locate and isolate the leaflet in question for a reinstallation of the repair. The cryo catheter uses a gaseous exchange (NO or Argon) to drop the temperature of the tip of the catheter, and can reach temperatures as low as minus 75 degrees Celsius.

The lower apical anchor construction could consist of a coiled distal section to rotate into the apex of the left ventricle with a round or flat wire construction or a laser cut tube emulating a cork screw similar to a wine cork as described for example in FIG. 6 and FIG. 15. A variable pitch in the screw will allow for a more secure attachment into the surrounding tissue. Another device for tissue securement could include a swaging or ovalization of the screw anchor to achieve the same securement. The attachment to the anchor riser could be pinned, welded, or joined though other mechanical devices. Alternatively it could be constructed of the same material and laser cut from the same tube of stainless steel, Nitinol or other implantable material. At the proximal most end could be a loop or tube to receive the replacement chord such as illustrated in the connection 72 of FIG. 15 or a plurality replacement chords could be preloaded ready for delivery and extending out the handle of the catheter.

In another embodiment, the distal anchor could be delivered to the apex of the left ventricle with a plurality of replacement chords looped to the anchor and the extending back to most proximal handle section of the catheter. This would allow for a delivery of multiple anchors to a single point of origin extending vertically from the apex of the left ventricle and the free ends of the replacement chord would be extended back out of the delivery catheter for access and advancement of other tools for locking and cutting. Over these free ends a delivery piercing element or tube can be advanced to the mitral leaflet to pierce through and deliver a pledget or restraining element through the leaflet and to the back side (ventricular side) of the leaflet. This could secure a loop and restraining element to hold the loop from being pulled through the leaflet and acting as a strain relief element. Over the same free end of the replacement chord can be delivered a locking element to hold the position of the chord and pledget securely to the leaflet position. Once delivered, this free end can be cut. Finding and holding the leaflet can be achieved by the cryo-catheter to hold the leaflet from the atrial side or a gripping tool to grasp the leaflet from the free edge could also be used. Once the first piercing and pledget is delivered, the other free end can now be tensioned around the distal apex anchor and a second locking element can be delivered to hold the position relative to the end of the apex anchor. The chord or suture anchor can be secured by an interference fit to the distal apex anchor and/or to the other chord line running up to the mitral leaflet. It is important to note the drawings illustrate the delivery and installation of the mitral leaflet anchor to the posterior leaflet but anchors and replacement chords could also be delivered to the anterior leaflet or any position on the mitral leaflet including the free margin, coaptation zone, or annulus.

Another method would be to place the distal rotational anchor in the left ventricle that is connected to a continuous loop of suture similar to a rubber band. One end would be secured to the distal anchor and the other end would pierce the mitral valve leaflet and be connected to a strain relief element to distribute the force on the ventricular side of the mitral leaflet, so as to prevent from pulling the replacement chord through the leaflet or tearing the leaflet. The strain relief element could be a laser cut tube that expands from a small configuration to a larger configuration once passed through the leaflet either through a compressive axial force or it could be constructed of a shape memory metal like Nitinol, where it is pre-set to a shape where the delivery diameter is small and the delivered diameter expands to a larger state. The delivered diameter could be about 0.5 millimeters expanding into about 2-3 millimeters in diameter and have a length of about 2 to 5 millimeters at delivery shortening to about 1-2 millimeters. It could also be constructed of shape memory metal and set to a round shape similar to an Amplatz device or a simple or complex suture knot located on the ventricular side of the leaflet. Another configuration could be a wound looped Nitinol wire that would look like a daisy with Nitinol wire peddles. This device could also be used to adjust the final length of the loop chord by winding or coiling the loop end passed through the leaflet. For example, the number of times the suture or chord is wound around the device could incrementally decrease the free length of the suture or chord. This winding mechanism could also be located at the distal coil anchor located in the left ventricle. The adjustment could be actuated during delivery to adjust the chord length and/or post-procedure where the adjustment is accessed and either shortened or lengthened. A rotational ratcheted drive coupled to a drive shaft or wire could be rotated external to the body by coupling and decoupling when adjustment is needed. The drive shaft could be a round wire constructed of stainless or Nitinol where a hex coupling interface between the drive shaft and winding mechanism could be used to engage and disengage the two elements. The two elements could be delivered in a mated configuration with one another for actuation and could later couple by using a loop snare to grasp the winding mechanism and couple the drive shaft engaging the hex drive device. The winding mechanism could utilize a simple rotational spool with a cog-style stop for anti-rotation or a friction resistance to hold the tensioned position. Alternatively, designing the distal coil anchor to accept an inner matching pitch adjustment screw, which would be coupled to the chord and allow for the outer body of the distal anchor to be driven into the apical tissue and secondarily a rotation of the inner matching pitch screw would allow for a tensioning of the chord by shortening the relative distance between the two screw elements. The simplest configuration would be a coil inside another coil where they both have right or left-hand threading and would couple with one another to provide a rotational motion into a translational or axial motion. Locking the two coils together post-adjustment would provide for a positive location of the chord length between the leaflet and the distal anchor system.

Patient Selection

In an embodiment, the method of treating a patient begins with selecting an appropriate patient. The methods, apparatuses, and systems, disclosed herein, however, are not limited to application only on preferable or otherwise appropriate patients. Preferably, the patient includes at least one three or five of the following characteristics from a first group:

Diagnosed with primary or degenerative mitral regurgitation.

Diagnosed with secondary or functional Mitral Regurgitation.

Diagnosed with Mixomotous Mitral Regurgitation.

Diagnosed with a flail leaflet, ruptured chordae, or leaflet prolapse.

Mitral regurgitation grade 1 or more; 2 or more; 3 or more or; 4 or more.

Annular diameter from A2 leaflet to P2 leaflet at least 5, 10, 15, 20, 30, 50 mm less than sum of length of P2+A2 leaflet. Similar mathematical relationships that ensure adequate redundant coaptation after repair, so as to create a durable repair, may also be used.

Annular diameter from A2 to P2 leaflet 10 to 50 mm, or preferably 24 to 36 mm, or most preferably 26 to 33 mm.

Access vessel diameter at least 2-10 mm diameter.

Preferably the patient has at least 1, 3, or 5 of the following characteristics from a second group:

Evaluated by a heart team including at least one, and preferably two, cardiac surgeons and determined not to be an appropriate candidate for conventional open surgical repair.

STS predicted operative mortality (Society of Thoracic Surgeons' Score or STS Score) of 2-20 or greater.

Patient was offered and refused open surgical repair.

Age between 18 and 90, or preferably between 35 and 85 more preferably between 40 and 85.

Patient will not accept blood transfusion.

Prior open chest surgery

Ejection fraction of at least 10-60 percent

For some embodiments of the device, it is preferable the patient is substantially free from the following conditions (the third group):

Moderate or severe COPD

Hypercoagulative disorder

Systemic degenerative collagen disease (i.e. Marfans syndrome)

Prior septal infarction affecting the anchor area

Ventricular septal defect

Known allergy to contrast media

Prior mitral valve replacement

In one embodiment the patient selected may meet at least 1, 2, or 3 criteria from the first group and at least 1, 2, or 3 criteria from the second group. In one embodiment, the patient selected may meet at least 1, 2, or 3 criteria from the first group and at least 1, 2, or 3 criteria from the second group and does not meet at least 1, 2, or 3 conditions from the third group.

Patients can be screened using echocardiographic imaging and/or CT imaging. MRI imaging is also possible. Preferably, a contrast gated cardiac CT with at least 32, 64, or 128 slices is obtained prior to the procedure and used for patient selection and/or case planning. Using imaging software, the annular diameter can be measured from the hinge point of A2 to hinge point of P2 leaflet, and the free length of the leaflet can be measured. These measurements can be compared to ensure that after the procedure is completed, sufficient redundant coaptation will be present to produce a durable repair. In one embodiment, the annular dimension may be reduced using another device or method such as a trans-catheter annuloplasty device, to create a small enough annular diameter.

Imaging

The present disclosure has the potential to allow excellent real time assessment and adjustment of suture placement and tension during the procedure. Some embodiments of the imaging method offer significant advantages in visualization even compared to what is available during open cardiac surgery.

Optimizing Tension

During open surgical mitral valve repair, the heart is stopped, flaccid and deflated, such that the surgeon has to estimate the movement of the dynamic structure based on his or her experience. The surgeon's initial assessment step involves filling the ventricle with saline to push the mitral leaflets into a closed position and visually assessing areas of leakage, prolapse and/or inadequate coaptation.

This assessment may be limited because it is not performed on a beating heart, but the sutures are tied off and secured based on this assessment, then the atrium is closed the heart is reanimated, and the final echo assessment or other monitoring procedure on the beating heart is performed. If an issue is identified, the surgeon may need to stop the heart again, reopen the atrium, and modify the previously completed repair. Because the sutures are knotted and trimmed they cannot simply be re-tensioned and so are typically replaced or additional artificial chords added. In some embodiments of the present disclosure, real time echocardiographic assessment is possible as the suture tensions are being adjusted individually.

In one embodiment, the method for implanting the artificial chords includes the following steps: First, securing one end of a plurality of artificial chords to a leaflet of the mitral valve or annulus of the surrounding tissue and the other end to an anchor point mechanically connected to the left ventricle; Second, adjusting the tension of the artificial chords while viewing an echocardiographic image other image of the mitral valve.

In some embodiments of the method described above, the echocardiographic image includes color Doppler assessment of velocity and or flow. In some embodiments, the echocardiographic image includes real time 3D or 4D echo. In some embodiments, the color flow Doppler and 3D images are fused or combined. In some embodiments, the Echo probe is placed through the patient's esophagus. In some embodiments, the echo probe is a surface probe on the patient's chest, and in some embodiments, the echo probe is within the patient's vascular system.

In some embodiments at least 1, 2, 3, 4, or 5 of the functions below are confirmed under echocardiography as the artificial chords are being tensioned. In another embodiment, the functions below are confirmed after the artificial chords are tensioned, but before the chords are permanently disconnected from the delivery system, where this may allow simplified re-tensioning if necessary.

Free from Systolic anterior leaflet motion causing obstruction or restriction of Left Ventricular Outflow Tract
Mitral valve gradient
Appearance of regurgitant jets
Velocity of regurgitant jest
Length of regurgitant jets
MR grade
A minimum leaflet coaptation distance of at least 3, 5, 9, 12, or 15 mm is achieved throughout the line of coaptation
Degree of leaflet prolapse or measurement of the height that a portion of the mitral leaflet moves above the plane of the mitral valve
Areas of "smoke" or stasis within the atrium ventricle or atrial appendage
Shunting between left and right ventricles, especially at anchor locations or other turns septal sections Additionally, during the assessment period after initial tensioning of the sutures and before disconnecting the sutures from the delivery system, or before trimming off excess suture, while suture tension is easily read adjustable, at least 1, 2, 3, 4, or 5 of the following are assessed:
Blood pressure
Cardiac output
ACT Actual clotting time
EKG electrocardiogram
Cardiac enzymes ckmb and troponin
Patency of coronary arteries
Fluoroscopic evaluation of ventricular shunt potentially from anchor or trans ventricular access.
Floroscopic appearance of ventricular anchor
Flouroscopic position of delivery system
Atrial pressure or wedge pressure
Oxygen content of patient's blood After the assessment step is completed based on the information obtained from the measurements, the physician or team may decide to make the results permanent or to readjust the tension, add additional repair components, or abort the procedure. In some embodiments the physician also has the option to remove the entire implant. In other embodiments, the physician has the option to remove the artificial chord portion of the implant but the ventricular anchor remains implanted. In some embodiments, the assessment step is further augmented by including a stress echo component where drugs such as pressure regulators are given to the patient to adjust the heart rate, cardiac output and ventricular pressure to further assess how the repair functions in different hemodynamic conditions.

Monitoring

During the procedure, the patient is preferably under conscious sedation. This can make Trans Esophageal Echocardiography more challenging, but minimizes anesthesia risk and allows patients to go home more quickly. With general anesthesia or conscious sedation during the procedure, standard cath lab monitoring procedures should be performed including arterial pressure, EkG, ACT, blood gasses, etc. Additionally, wedge pressure or left atrial pressure may be useful for this procedure. For this procedure, careful monitoring of arterial pressure provides an early indicator of damage to the mitral valve apparatus, entanglement of the device in chordae, and/or damage to the septal wall. Measuring left atrial pressure may provide a simple quantifiable measure of improvement in mitral function without the challenges associated with getting the appropriate echocardiographic view.

Access

A blood vessel is accessed through conventional methods standard in interventional cardiology. Preferably, the vessel is a vein. In one embodiment, the vessel is the femoral vein. In another embodiment, the vessel is the radial brachial or subclavian vein. Access may be by cut-down or percutaneous needle stick. In some embodiments, the vessel is prepared for closure by pre-insertion of a vascular closure device, such as Percolse or Prostar (Abbot Vascular)

A guidewire may be advanced, optionally using a guide catheter, through a valve into the right ventricle. The device of the present disclosure can be advanced over the guidewire to a position near the apex of the ventricle.

A sharp curve may be created at the tip of the device. The curve can be oriented so that the exit lumen points towards the septal wall of the heart. The radius of curvature of the fully curved system is preferably less than about 3-30 mm, and the curvature is preferably positioned less than about 5-50 mm from the tip of the system.

In one embodiment, this curve is created using a steerable catheter. Certain embodiments of a steerable catheter incorporates a pull wire that when pulled creates the inner radius of the catheter. Some embodiments also include a coil, a braid, and/or an axial reinforcement.

In another embodiment, the curve is created using coaxial sheaths with different shapes. For example, an outer sheath substantially straight or with a large radius of curvature near its tip combined with an inner sheath with a small radius of curvature at its distal tip may be used. By advancing the inner sheath out of the outer sheath, the tip of the catheter creates the desired curve. By advancing the more curved sheath further, a greater curved angle is obtained.

In some embodiment, the sheaths have different relative stiffnesses at different points in their length. In certain embodiments, the outer sheath is curved to access the apex of the ventricle and stabilize through the vena cava. The shape that enables this may be about 7 to 50 cm back from the distal tip of the sheath. The inner sheath can be substantially more flexible (e.g., less than about 30, 50, 70, or 90% the bending stiffness by ASTM three point bend test) than the outer sheath in the range at about 7 to 55 cm from its distal tip. This enables the inner sheath to move relative to the outer sheath without substantially changing the orientation of the outer sheath in the heart and vena cava. The distal portion of the inner sheath is preferably stiffer than the previously described section, and stiff enough that as it is extended out of the outer sheath, it assumes its approximate shape despite contact with the structures of the heart.

The device may be oriented so that the exit of the catheter is near the right ventricular apex, pointing into the septal wall, and, preferably, upwards towards the mitral valve. The position of the sheath can be confirmed by imaging. A four chamber echocardiaographic view may be used in some embodiments. A short axis mitral view may be used in other embodiments. Fluoroscopic imaging can be used in some embodiments. Depending on the location of the area in need of repair, the desired puncture site can be selected and the appropriate angle based on the planned orientation of the replacement chords.

In some embodiments, a puncture higher up, closer to the papillary muscle insertions, and away from the ventricular apex is preferred. This location provides the benefit that as the heart remodels and the ventricular volume is reduced to more normal physiological levels, the tension in the chords will change less than with a near apical attachment.

A needle and/or dilator may be advanced through the sheath or sheaths and through the septal wall of the heart. In some embodiments, a needle and dilator are used together. Both the needle and dilator can be pre-shaped with curvature near their distal tip to ensure the needle stays within the left ventricle and avoids the mitral valve apparatus. Presence of the needle in the left ventricle may be confirmed with echocardiography, fluoroscopy, and/or by the presence of red (oxygenated) pulsatile blood at the proximal end of the needle.

After ventricular access is gained, a guidewire can be advanced across the septum. In some embodiments, the guidewire is further advanced across the mitral valve into the atrium, and, in some embodiments, is advanced further into a pulmonary vein. The wire can be confirmed not to be tangled in the mitral apparatus using echocardiography and/or wire manipulation. In some embodiments, a device such as a balloon or sheath is advanced over the wire to confirm that the wire does not pass through the chordal structure.

Ventricular Anchor

The present disclosure include several embodiments of ventricular anchors.

In one embodiment, the ventricular anchor is similar to an Amplatz septal occluder (ST Jude Medical) consisting of a braided section that expands on both sides of the septal wall.

In another embodiment, the anchor is a barbed stent-like structure intended to be deployed within the ventricular wall. The stent structure may be self-expanding or mechanically expandable (i.e. balloon expandable) and may include barbed anchors similar to those found on stent grafts such as Endurant (Medtronic)

In another embodiment, the anchor is a flanged covered stent where the right ventricular side opens into a substantially flat configuration oriented in a plane substantially perpendicular to the axis of the stent.

In another embodiment, the flange is constructed from a ring around the circumference of the flange and the flange itself a layer of fabric. The flange can be collapsed into an elliptical shape and delivered through the lumen. The ring may be constructed from nitinol titanium stainless steel or a cobalt chrome alloy. A fabric lumen can extend through the center of the flange and into the trans-septal puncture. After chord implantation, tension to snug the flange against the septal wall is provided through the chords, in some embodiments. During the procedure, a portion of the delivery system can be used to push the flange against the septal wall. In other embodiments, the fabric sleeve incorporates and anchors such as a stent or a barb to stabilize it within the septal wall.

The ventricular anchor may be deployed over a guidewire. After the anchor is deployed, the chord delivery anchors and their delivery system can be delivered through the ventricular anchor and over the guidewire.

Positioning

Identifying the correct place to place the new chords can be performed substantially using echocardiography. The area of a regurgitant jet or a leaflet prolapse or flail can be identified using 2D or 3D echo and/or color flow Doppler. Preferably, a combination of these imaging modalities is used.

The device to deliver the chords may be advanced across the septal puncture. In some embodiments, the same steerable or shapeable system used to create the septal puncture is advanced across the puncture. In other embodiments, it is a separate device that can pass through the other sheaths.

The position of the distal tip of the device can be oriented relative to the mitral structure as follows. The device may be biased more anteriorly by increasing the curvature of the system where it passes into the left ventricle through the septum. The device may be biased more posteriorly by decreasing the curvature of the system where it passes into the left ventricle through the septum. The device may be biased from commissure to commissure by rotating the curved portion that passes through the sheath. The device may be biased atrially by extending, or ventricularly by retracting, the distal portion of the device.

Primary

To replace primary chords, the chords located near the free edge of the leaflet, several methods of engaging the mitral leaflet are possible. The bulky knot system used by Harpoon Medical may be used in one embodiment. The looped suture used by Neochord Inc. may be used in another embodiment. Both these methods appear to work well in early clinical experience. The preferred embodiments intend to replicate the clinically proven suture tissue interfaces that have been developed in the open surgical experience.

Another embodiment may use a bifurcated catheter. One side of the catheter engages under the leaflet, and this side can be pushed on to help identify the area of the leaflet where the suture will pass. The other side passes into the atrium. A needle or pair of needles puncture the leaflet from the first side of the catheter and a snare captures the needles or the suture from the needles from the second side of the catheter. In some embodiments, a loop end of the suture is passed over the snare such that when the needle end of the suture is pulled back through it forms a girth hitch. In other embodiments, the loop end of the suture is twisted and doubled over twice forming a knot known a prusik or double girth hitch.

Secondary

To replace secondary chords, those that are located farther back from the free edge of the leaflet, some of the devices and methods described to replace primary chords may need adaptation. The bulky knot anchoring method can be appropriate for replacing secondary chords without modification.

The bifurcated catheter method can be appropriate for replacing secondary chords with a minor adaptation to allow the snare side to puncture the leaflet.

Resect Like

During mitral valve repair surgeons often resect some of the leaflet tissue. A similar effect can be created using the bifurcated catheter system described above. By placing suture through a section of leaflet and gathering the tissue together as the suture is tightened a similar effect can be achieved. The suture can be noted close to the leaflet to only resect, or extended and used as a new chord as well.

Partially Annuloplasty

In some cases, it may be desirable to use the dual puncture method into the annulus close to the hinge point of the leaflet to create a result similar to a surgical suture annuloplasty. In some embodiments, a series of suture loops are created, encircling the entire annulus. In some embodiments, suture loops are created only in a safe area away from the aortic valve, coronary arteries, and conduction pathways. In some embodiments, the suture loops are created in the areas where the heart is most likely to dilate (i.e. in an area of prior infarct) or in an area near the mitral commissures.

Assessment

After one or more repair sutures are placed into the mitral structure, the result may be assessed. Tension is applied selectively on each artificial chord until the desired leaflet motion is achieved. Preferably, a target coaptation height is achieved by echocardiography. In some embodiments, as too much and too little tension are balanced, the sutures are slightly over tensioned to allow some remodeling to occur.

Knotting

In one embodiment the sutures are knotted on the right ventricular side of the anchor using a crimpable knot large enough to prevent the crimped knot from passing through an opening in the anchor.

In another embodiment, the artificial cords are crimped directly to a suture-sewn or tied to the anchor.

Suture Adjustment

In some embodiments, the artificial chord tension can be adjusted in a similar procedure. In some embodiments, this can be achieved entirely from the right ventricle without re-crossing the septum. In one embodiment, the crimpable knots are snared, pulled away from their base and twisted. The twisting motion of the suture of pair of sutures forming the artificial chord effectively shortens it. In another embodiment, the crimp knot is snared and pulled and an additional crimp knot placed over it.

Multiple Systems

In some embodiments, it is possible to attach up to 1 to about 10 artificial chords to a single septal anchor. In some embodiments, more than one ventricular anchor is used, either to optimize the direction of pull of the chords, or to minimize the load on the septal anchor.

Alternative Methods

For some patient anatomies, it may be necessary or desirable to anchor the chords to a different area of the left ventricle rather than the septal wall. In one embodiment the anchoring location is at the papillary muscle. Preferably, the suture attachment to the papillary muscle or ventricular wall is made by creating a figure-eight suture, as is commonly done by surgeons during open chordal replacement. This type of anchor can be placed by a trans-catheter method through the trans-septal ventricular puncture described above, or can be placed through a more conventional atrial trans-septal puncture. One embodiment of the system, as adapted to suture to papillary muscles, is a simple change to the bifurcated leaflet suturing system where the needle and snare ends are curved inward towards each other so that when actuated they can place a suture through a papilay muscle. In another embodiment, the ventricular anchor is a cork screw shaped anchor similar to an Aptos Endovascular staple (Medtronic Inc) or any of the configurations used to secure pacemaker leads.

Bailout

In some embodiments, the ventricular anchor is retrievable. One example is a recapturable self-expanding stent, or an Amplatz like device.

In some embodiments, artificial chords are retrievable through a hemodynamic assessment period. In one embodiment, this is achieved by pulling both ends of the suture for assessment, prior to engaging the girth hitch for permanent implantation Concomitant Repair Rings Alfieri In some embodiments, the procedure is performed in conjunction with another mitral valve repair procedure. This simulates the multiple techniques typically used by surgeons. There are several devices in clinical use that simulate annuloplasty rings such as cardiac dimension coronary sinus based approaches, Mitralign and Valtech suture based approaches, etc. Additionally, Mitraclip (Abbott) simulates an Alfieri stitch, a seldom used surgical technique that creates two orifices.

Device

Certain embodiments of the device include and outer sheath that is curved to engage the shape of the vena cava and right ventricle. The proximal end of the outer sheath is connected to the handle of the delivery system. Within the outer sheath is a conventional dilator for gaining vascular access. Once the right ventricle has been accessed, the dilator is changed out for a special trans-ventricular dilator, with a relatively flexible proximal portion and a stiffer sharply curved distal portion with a short tapered radio opaque tip. The handle can include a provision to lock to the dilator, preventing both axial and rotational movement. The internal diameter (ID) of the dilator allows clearance for a long flexible, preferably hollow needle. In some embodiments the needle is curved. The needle can be configured to allow the needle tip to be advanced through the distal tip of the dilator and precisely place the trans-ventricular puncture. In some embodiments, the needle is sized to accommodate a 0.009, 0.014, 0.018, or 0.035 inch diameter guidewire. In other embodiments, the dilator is advanced through the puncture and over the needle and the needle is withdrawn. In some embodiments, the needle is integral to the dilator and can be retracted within the dilator or extended a limited length past the tip of the dilator. In some embodiments, the length may be about 2 to 20 mm. In other embodiments, the length may be about 4 to 40 mm. In some embodiments, the length maybe less than about 2 mm or greater than about 40 mm.

Figure 35A:
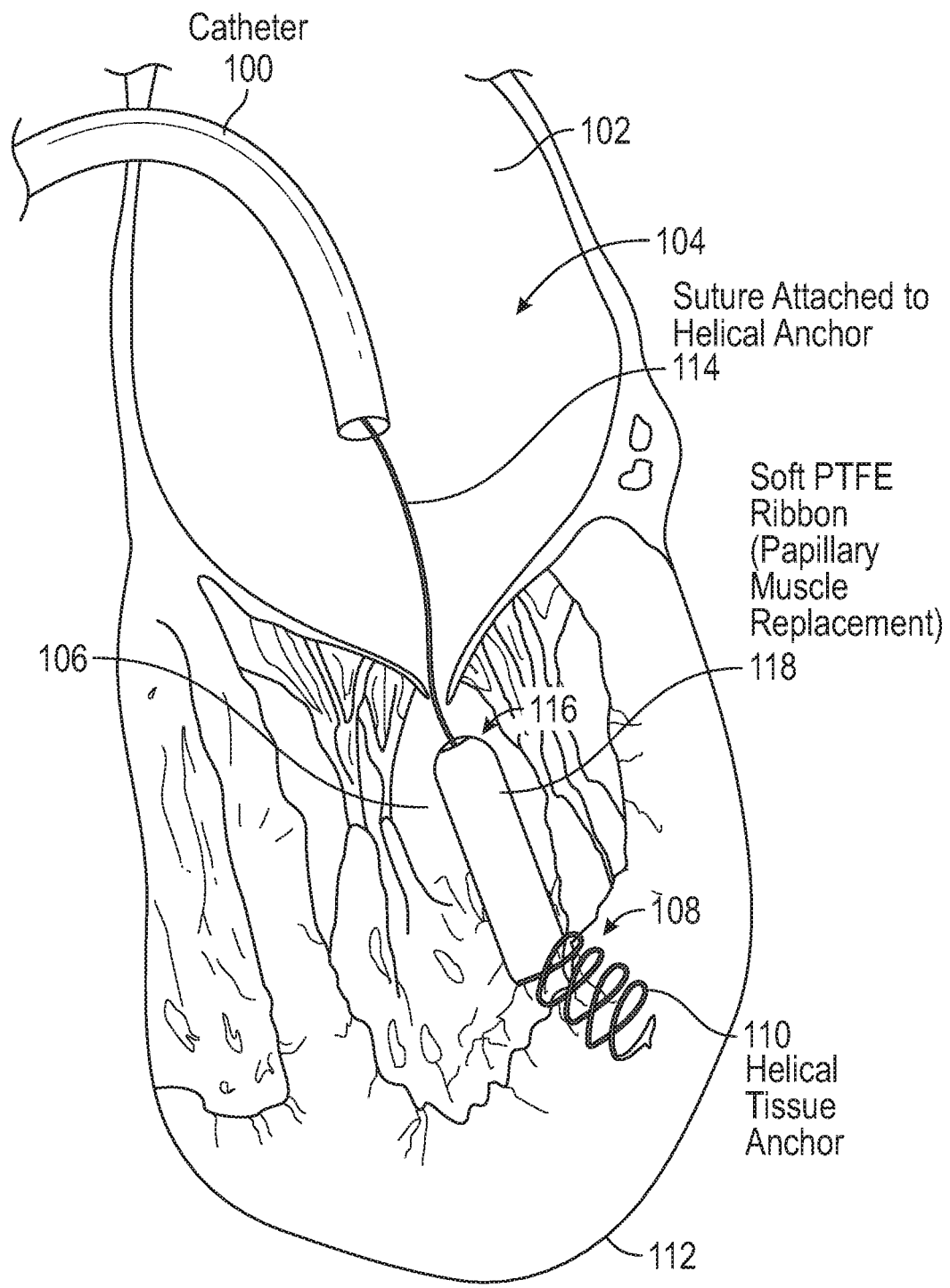
FIG. 35A illustrates attachment of a neo papillary muscle within the left ventricle.

One exemplary application of the foregoing is discussed below, in connection with FIGS. 35A through 35O. Referring to FIG. 35A, a catheter 100 (also referred to herein as an elongate, flexible tubular body) having a distal end and a proximal end. The distal end of catheter 100 has entered the left atrium 102 via conventional techniques. The catheter 100 is advanced through the mitral valve 104 to the vicinity of the apex 112 of left ventricle 106. A tissue anchor 108, such as a helical tissue anchor 110, is rotated into the muscular wall by an anchor driver (not shown), which can be in the form of a rotational driver (not shown) advanced distally through catheter 100. In certain embodiments, the anchor driver or rotational deriver can extend proximally through the catheter 100. After anchoring the tissue anchor 108, the catheter 100 and/or anchor driver is proximally retracted to leave the anchor 110 secured to the wall, and attached to an anchor suture 114 which extends proximally throughout the length of the catheter 100. A distal portion of the anchor suture 114 may carry a neo papillary muscle 116 which may comprise a soft ribbon or body 118, optionally approximating the size of a mitral papillary muscle. The neo papillary muscle 116 may comprise a substantially larger diameter compared to the suture 114. The suture 114 may be configured to extend through the neo papillary muscle 116 (e.g., through a central channel) or may be affixed at a proximal end of the neo papillary muscle, as described elsewhere herein. In certain embodiments, the neo papillary muscle replacement 118 can be formed of soft PTFE material.

Preferably the anchor 108 is attached at a point that is offset from the thin tissue of the apex 112, and is instead implanted in the generally thicker adjacent wall of the ventricle. Positioning the anchor is preferably also such that the longitudinal axis of the implanted neo chord construct is aligned approximately parallel to or concentric with the original path of the native chord. In such arrangements, the tissue anchor 108 can be positioned in left ventricle between the papillary muscles. As noted and described herein, the tissue anchor can be in the form of a helical ventricular anchor.

Figure 35B:
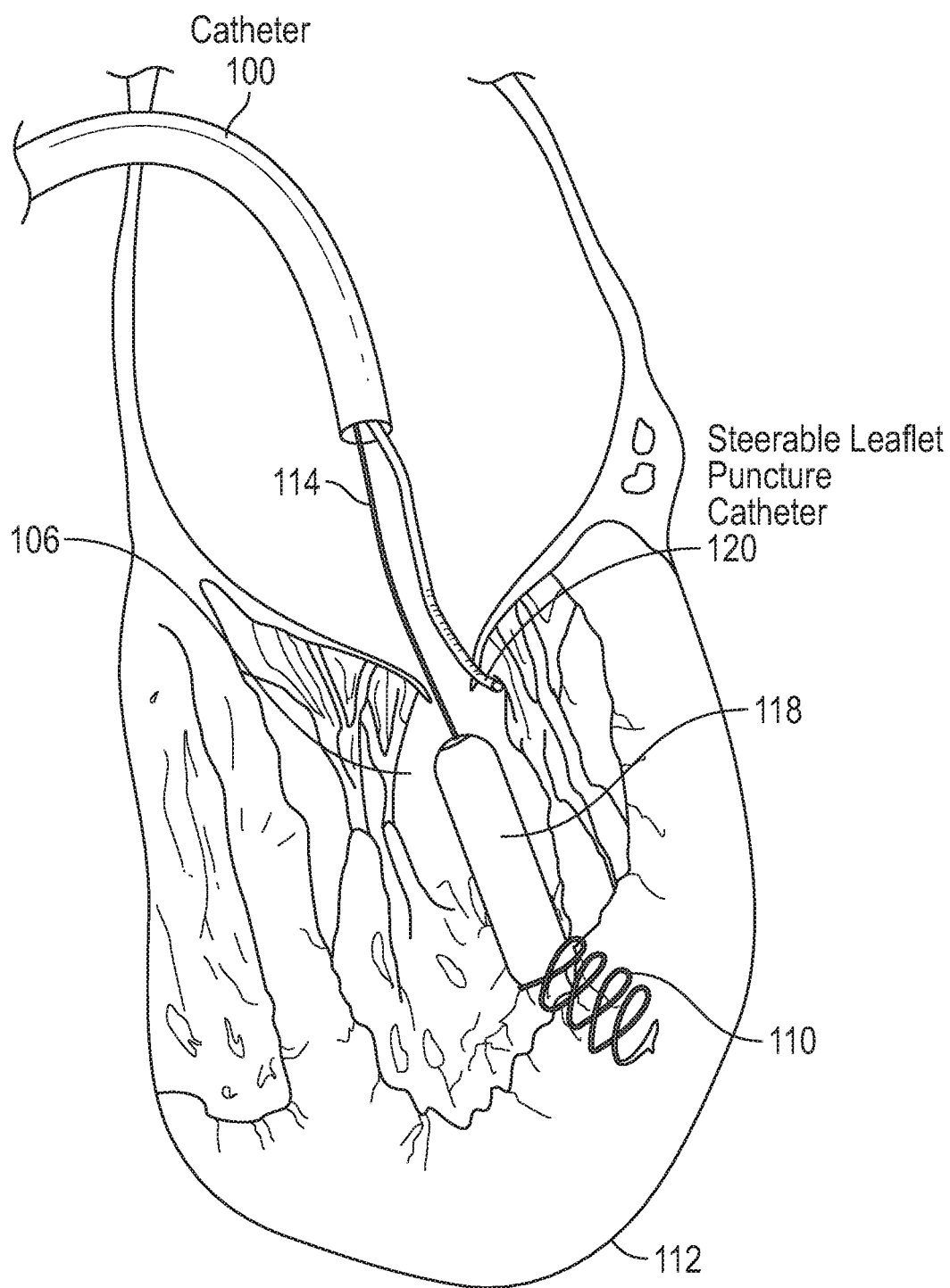
FIG. 35B illustrates a steerable leaflet puncture catheter advancing through the mitral valve.

Referring to FIG. 35B, a steerable leaflet capture catheter 120 can be advanced distally beyond the catheter 100, through the mitral valve 104 and into the left ventricle 106. The steerable catheter 120 may be delivered through the catheter 100. Alternatively the steerable catheter 120 may be delivered alongside catheter 100. In certain embodiments, the steerable leaflet capture catheter 120 can be positioned within the catheter 100 along the driver (e.g., rotational driver) coupled to the tissue anchor (e.g., a helical ventricular anchor). In certain embodiments, the driver (e.g., rotational driver) coupled to the tissue anchor (e.g., a helical ventricular anchor) can be inserted through the catheter 100 and after deployment removed or partially removed from the catheter 100. The steerable leaflet capture catheter 120 can be then be advanced through the catheter 100 to the target site.

A distal portion of leaflet capture catheter 120 can be provided with a deflection zone 122. Deflection zone 122 may comprise any of a variety of deflection mechanisms. For example, a plurality of transverse slots 124 may be spaced apart along a first side of the catheter 120. A second, opposing side 126 of the catheter may comprise an axially incompressible spine. Proximal retraction of one or more pull wires (not shown) may cause axial collapse of the slots 124, thereby deflecting the catheter as shown, for example, in FIG. 35C. The slots 124 may be specifically configured to allow the types and ranges of motions suited for the insertion of the leaflet anchor.

Preferably, the deflection zone 122 may be deflected throughout an angle of at least about 160° and preferably at least about 180° or about 190° or more in a simple or compound curve, and have a best fit radius of curvature of less than about 2 cm, and in one embodiment, less than 1.5 and, preferably, less than about 1 cm in an embodiment. In one implementation, the shortest linear distance D between the distal tip 128 and the catheter shaft is within the range of from about 0.5 cm and about 1.5 cm and optimally approximately 1 cm, to position the leaflet anchor a desired setback from the leaflet coaptive edge.

Figure 35C:
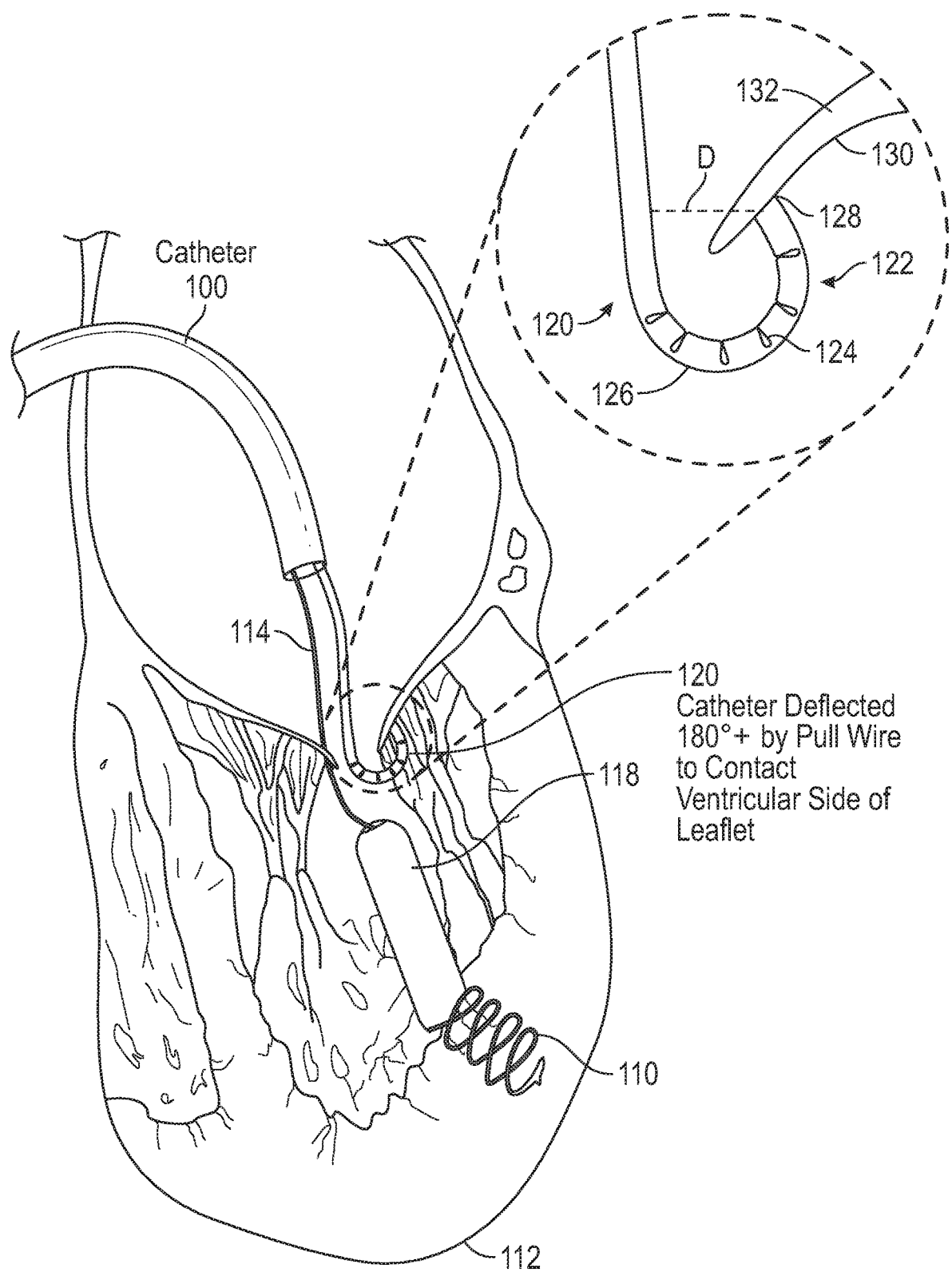
FIG. 35C illustrates the steerable leaflet puncture catheter deflected through an angle of at least about 180°.

The steerable leaflet capture catheter 120 may be advanced through the mitral valve 104 and deflected as illustrated in FIG. 35C to position distal tip 128 in contact with a ventricular side 130 of a flail leaflet 132.

Figures 35D, 35E:
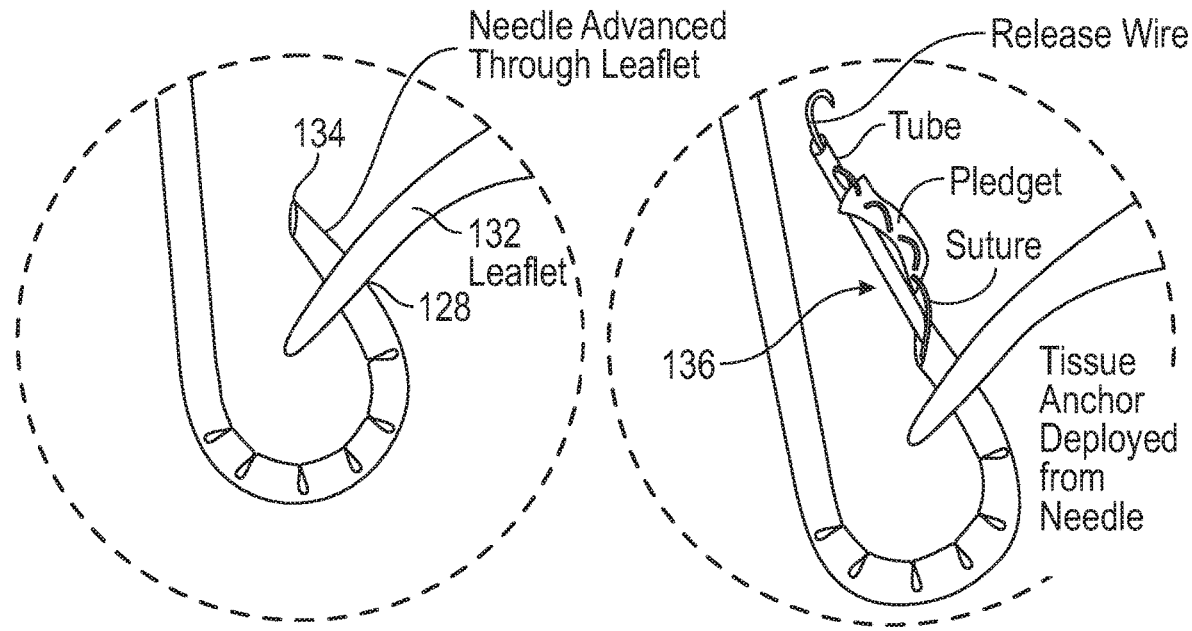
FIGS. 35D through 35G illustrate puncturing the leaflet and deployment of a collapsible pledget type leaflet anchor.

As illustrated in FIG. 35D, a control on a proximal manifold may be manipulated to advance a needle 134 out of the distal end 128 and through the flail leaflet 132. Puncture of leaflet 132 by needle 134 may be accomplished during diastole, when the leaflet 132 is biased in the direction of the left ventricle 106.

Figures 35F, 35G:
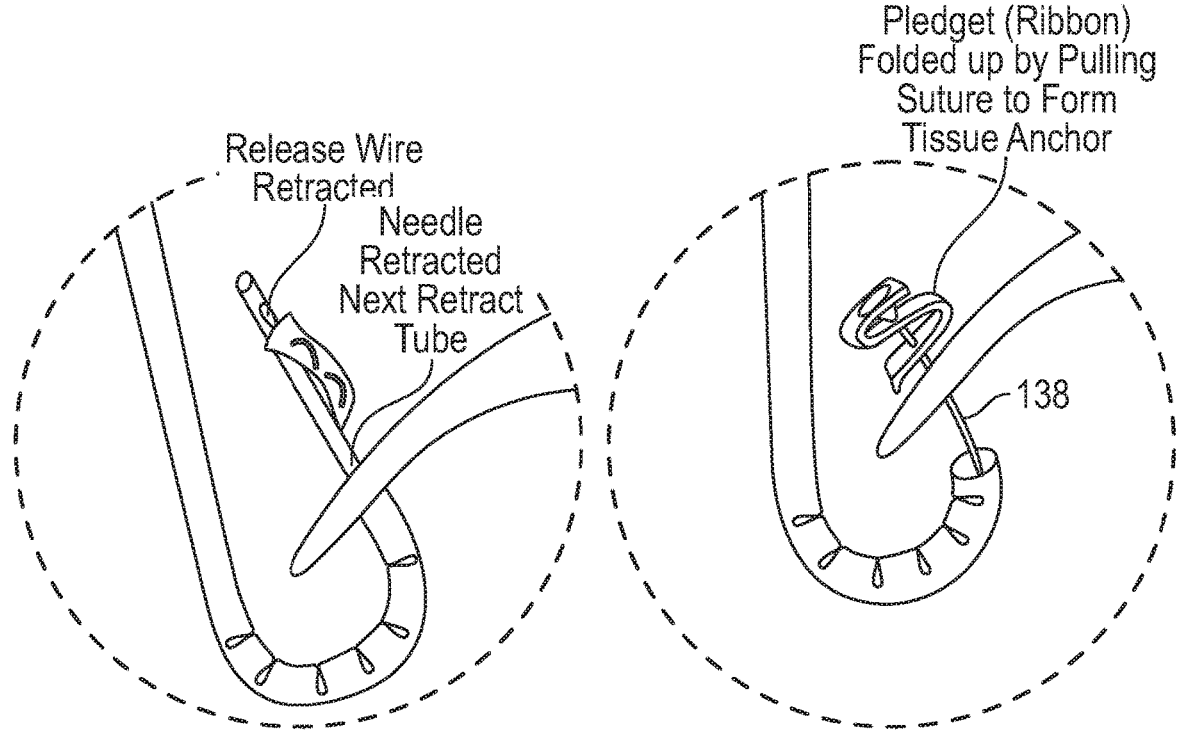

The catheter 120 and/or needle 134 may be utilized to deploy any of a variety of tissue anchors to secure a suture to leaflet 132. In certain embodiments as described herein, the tissue anchor is radially enlargeable leaflet anchor coupled to a suture which can extend proximally through the catheter 100. In the illustrated embodiment, a pledget 136 carried by a leaflet anchor suture 138 is deployed from the needle 134 on the atrium side of the leaflet 132. The pledget is in the form of an elongate ribbon, having a proximal end and a distal end. The distal end is secured with respect to the leaflet anchor suture 138. The leaflet anchor suture 138 may be threaded through one or two or four or more apertures in the elongated ribbon. As seen in FIGS. 35E through 35G, proximal retraction on the leaflet anchor suture 138 causes the ribbon to fold and collapse axially, thereby forming a mass of sufficient transverse area, such that proximal tension on the leaflet suture is insufficient to pull the resulting pledget through the leaflet. Accordingly, in certain arrangements, the pledget 136 is transformable from an elongate strip configuration to a radially enlarged, axially shortened configuration by proximal retraction of the suture 138.

Figure 35H:
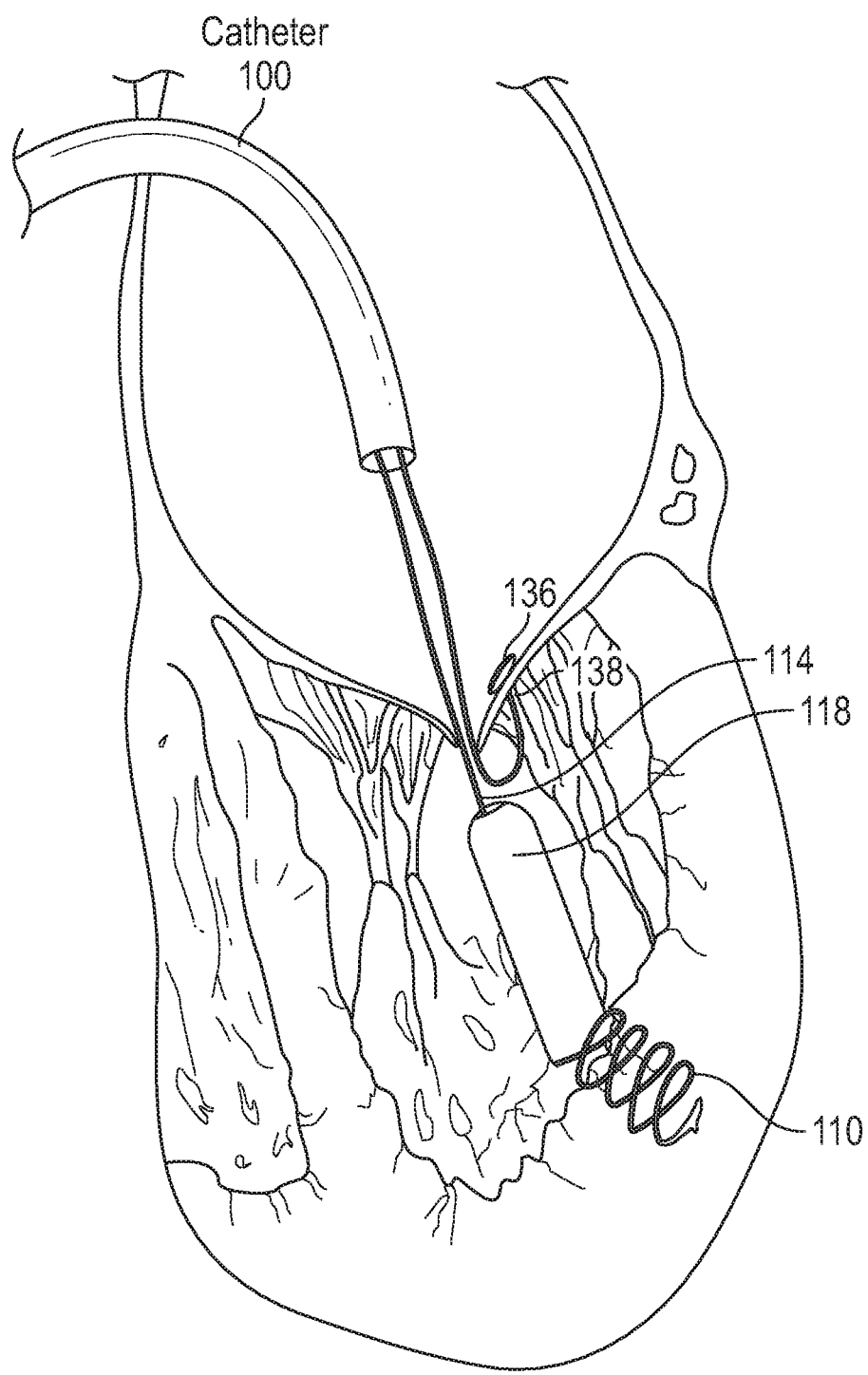
FIG. 35H illustrates a ventricle suture and a leaflet suture extending proximally through the deployment catheter.

The leaflet capture catheter 120 may be thereafter proximally retracted, leaving the construct as illustrated in FIG. 35H.

Any of a variety of leaflet anchors may be utilized, generally sharing the characteristic of being laterally enlargeable from a low crossing profile for crossing the leaflet, to a larger transverse profile for resisting retraction back through the leaflet. Lateral enlargement may be accomplished by tilting a T anchor or by active deformation by a control wire or elastic deformation following release from a constraint.

Figures 1, 35I:
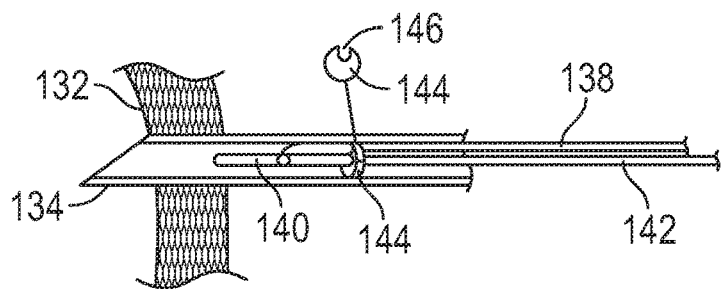
Figures 2, 35I:
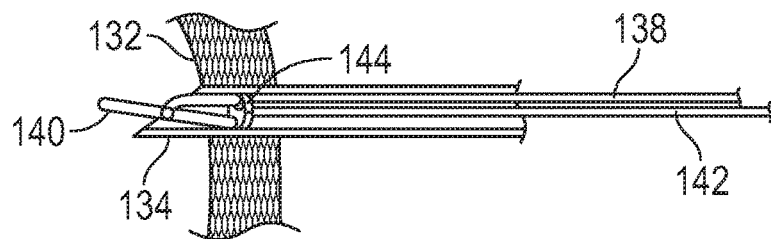
Figures 3, 35I:
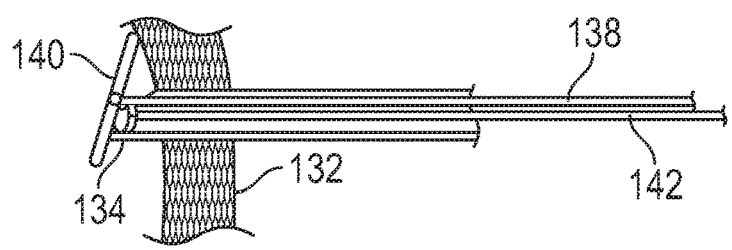
Figures 4, 35I:
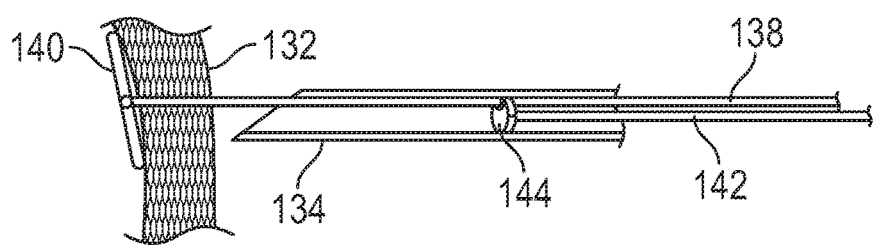

FIGS. 35I-1 through 35I-4 illustrate deployment of a T tag type anchor through the flail leaflet 132. An anchor element such as a single T tag bar 140 secured to suture 138 may be distally advanced through the needle 134 by a push wire 142. Push wire 142 may be provided with a distal pushing platform 144, which may be provided with a cut out 146 for accommodating suture 138. As the bar 140 exits the needle 134, it will rotate about the suture attachment point and seat against the atrium side of the leaflet 132 upon proximal traction on leaflet suture 138. The bar 140 may comprise a single element as illustrated, or an "X" or multi strut construct, depending upon desired performance characteristics.

Figures 1, 35J:
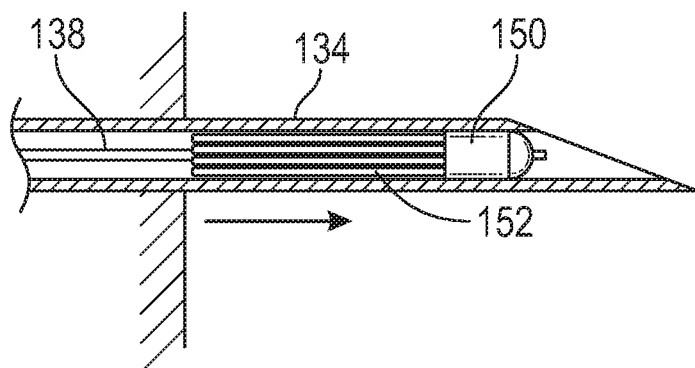
Figures 2, 35J:
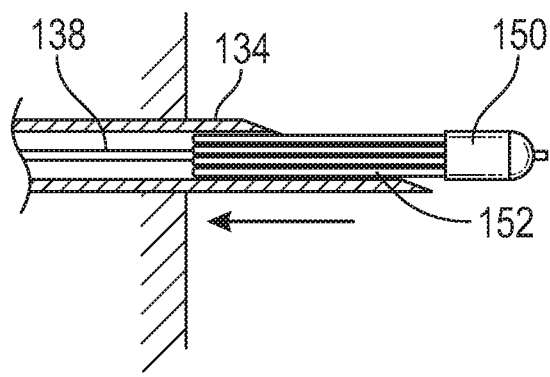
Figures 3, 35J:
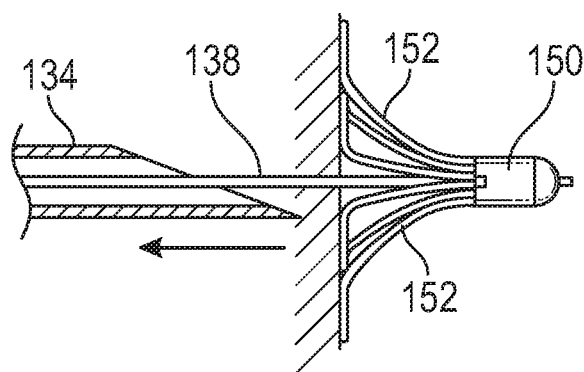

An alternative leaflet anchor is illustrated in the sequence of FIGS. 35J-1 through 35J-3. The tissue anchor comprises a hub 150 secured to the suture 138. Hub 150 carries a plurality of spokes 152 which are enlargeable transversely from a low profile linear configuration when constrained within needle 134, to an expanded configuration illustrated in FIG. 35J-3 for resisting proximal retraction through the leaflet 132. At least two, and preferably four, or six, or more spokes or struts 152 may be provided, extending radially outwardly from the hub 150 in the deployed configuration, for providing a footprint against the leaflet. The struts may be inclined radially outwardly in the proximal direction to provide a force damper allowing hub 150 to be transiently drawn closer to leaflet 132 in response to tension spikes, such as when the leaflet 132 reaches the limit of travel during systole imposed by the implanted neo chord. The spokes 152 and hub 150 may be laser cut from a NiTi tube and adhesively bonded, crimped, or otherwise attached to the leaflet suture 138.

Figure 35K:
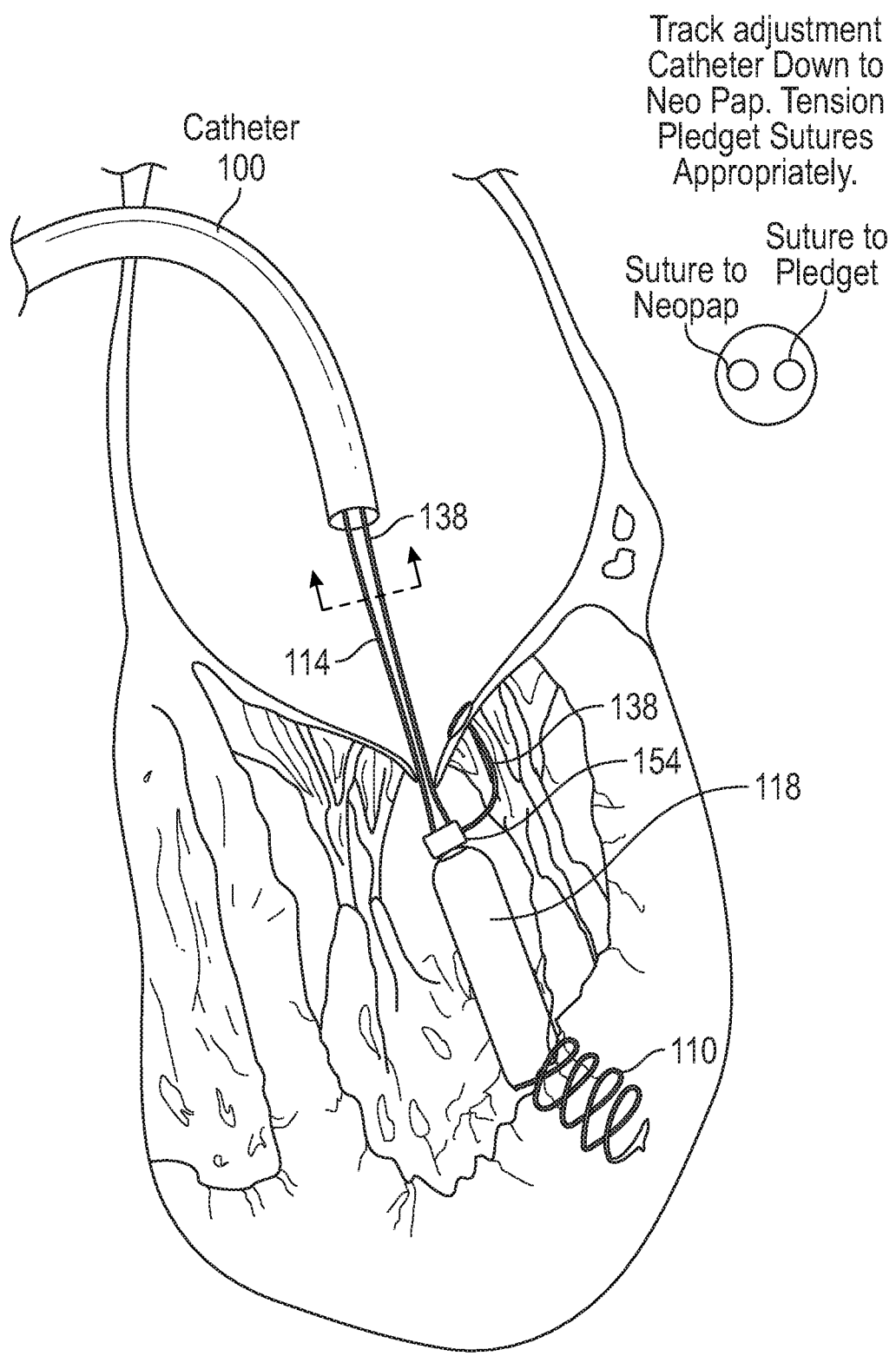
FIG. 35K schematically illustrates a fulcrum positioned at about the proximal end of the neo papillary muscle.

Referring to FIG. 35K, a fulcrum 154 may be positioned at about the distal end of the neo chord and proximal end of the neo papillary muscle. The fulcrum 154 may provide a point at which length and/or tension between the leaflet anchor 136 and the distal anchor 110 can be adjusted. At least the leaflet suture 138 passes across the fulcrum, so that proximal retraction on the leaflet suture 138 pulls the atrium direction limit of travel of the flail leaflet in the direction of the ventricle. The fulcrum 154 may be the edge of a distal opening of a lumen of an adjustment catheter which is advanced distally over the leaflet suture and potentially also the ventricle anchor suture. The fulcrum may alternatively comprise an eye or loop on the distal end of a fulcrum support such as a hypo tube or support wire. Alternatively, the fulcrum 154 may be on a suture lock, through which both of the anchor suture and leaflet suture may pass.

Prior to engaging the suture lock, the leaflet suture may be slowly proximally retracted to progressively limit prolapse of the flail leaflet into the left atrium. Mitral regurgitation can be observed via fluoroscopic imaging, and the leaflet suture can be retracted until mitral regurgitation (MR) has been eliminated or sufficiently minimized.

Figure 35L:
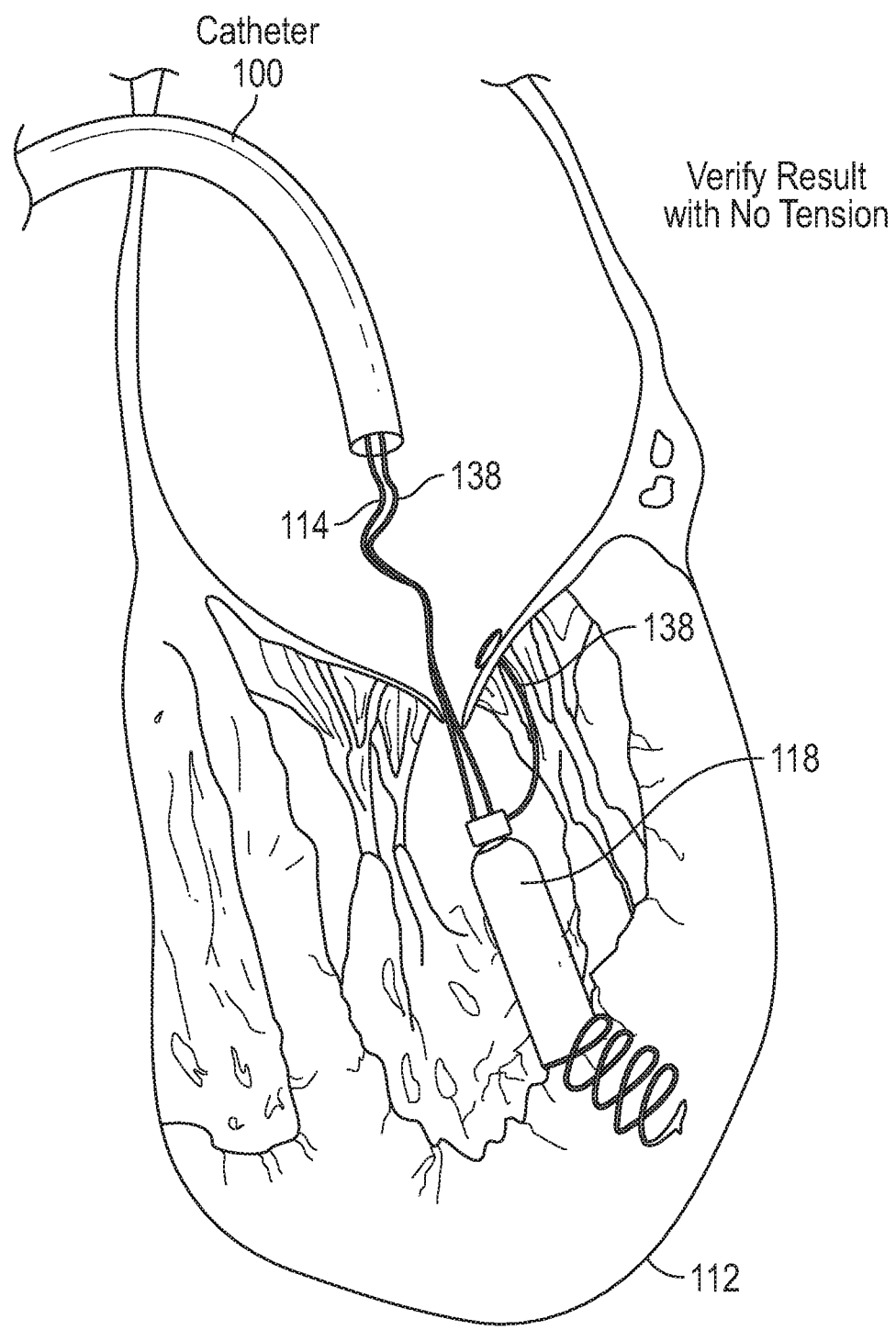
FIG. 35L illustrates verifying mitral valve function prior to removal of the deployment system.
Figure 35M:
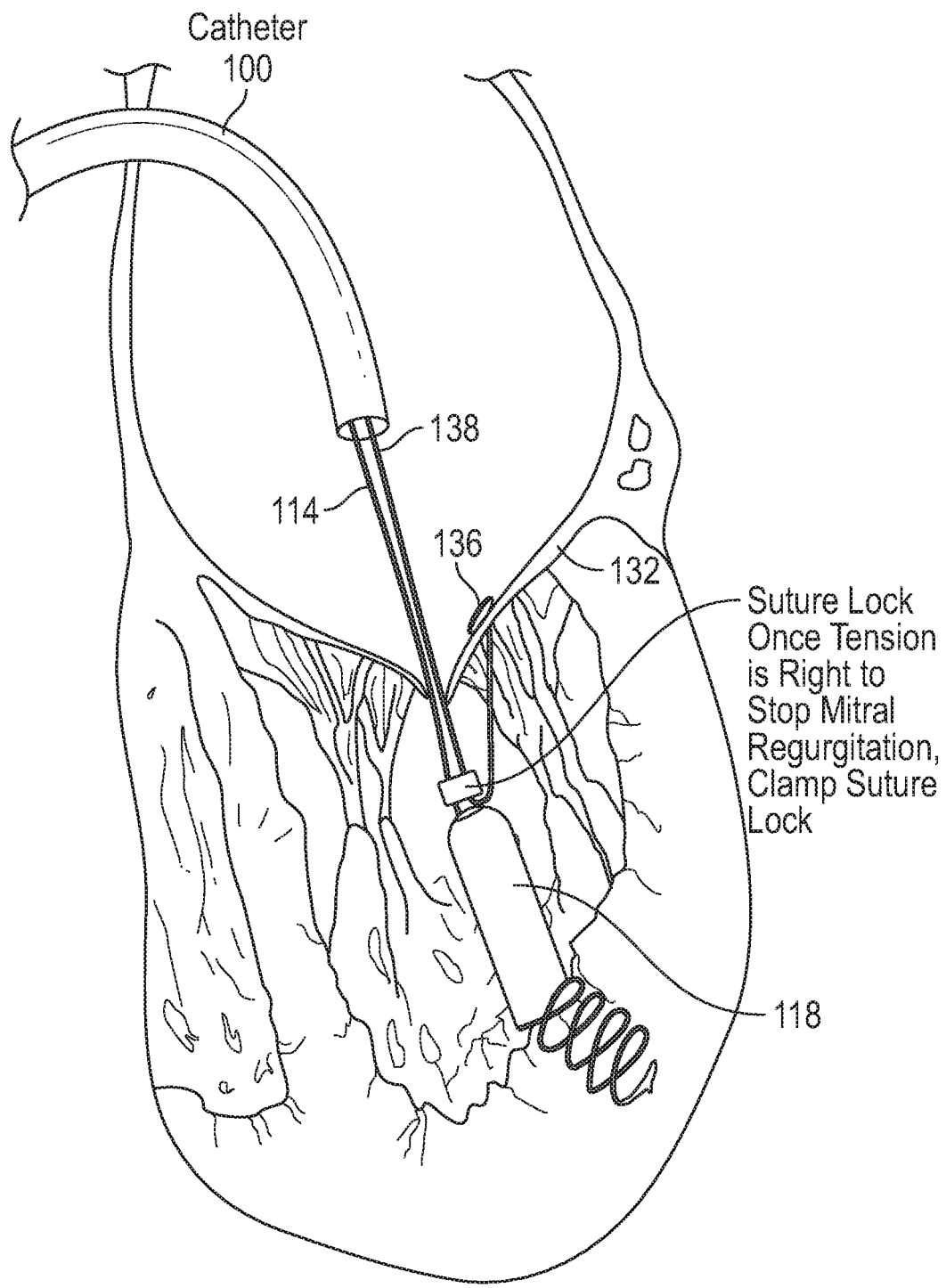
FIG. 35M illustrates the attachment of the leaflet suture to the ventricle suture following desired tensioning.

Referring to FIG. 35L, the catheter 100 maybe advanced distally to induce slack in the anchor suture and leaflet suture, thereby minimizing any influence of the catheter 100 on leaflet function. This enables the physician to evaluate the effect on mitral regurgitation at the current tension level on the leaflet suture. The leaflet suture may be retracted or advanced to further adjust the leaflet range of travel, as desired.

Once the desired cardiac function has been achieved, the suture lock may be engaged, using known techniques or techniques disclosed elsewhere herein, to fix the maximum distance between the tissue anchor 108 and the leaflet anchor, as shown in FIG. 35 M. Alternatively, if the adjustment catheter was utilized as the fulcrum, a suture lock or knot may be advanced distally through the catheter into position in the vicinity of the distal end of the neo cord and the proximal end of the neo papillary muscle, and secured prior to retracting the adjustment catheter.

Figure 35N:
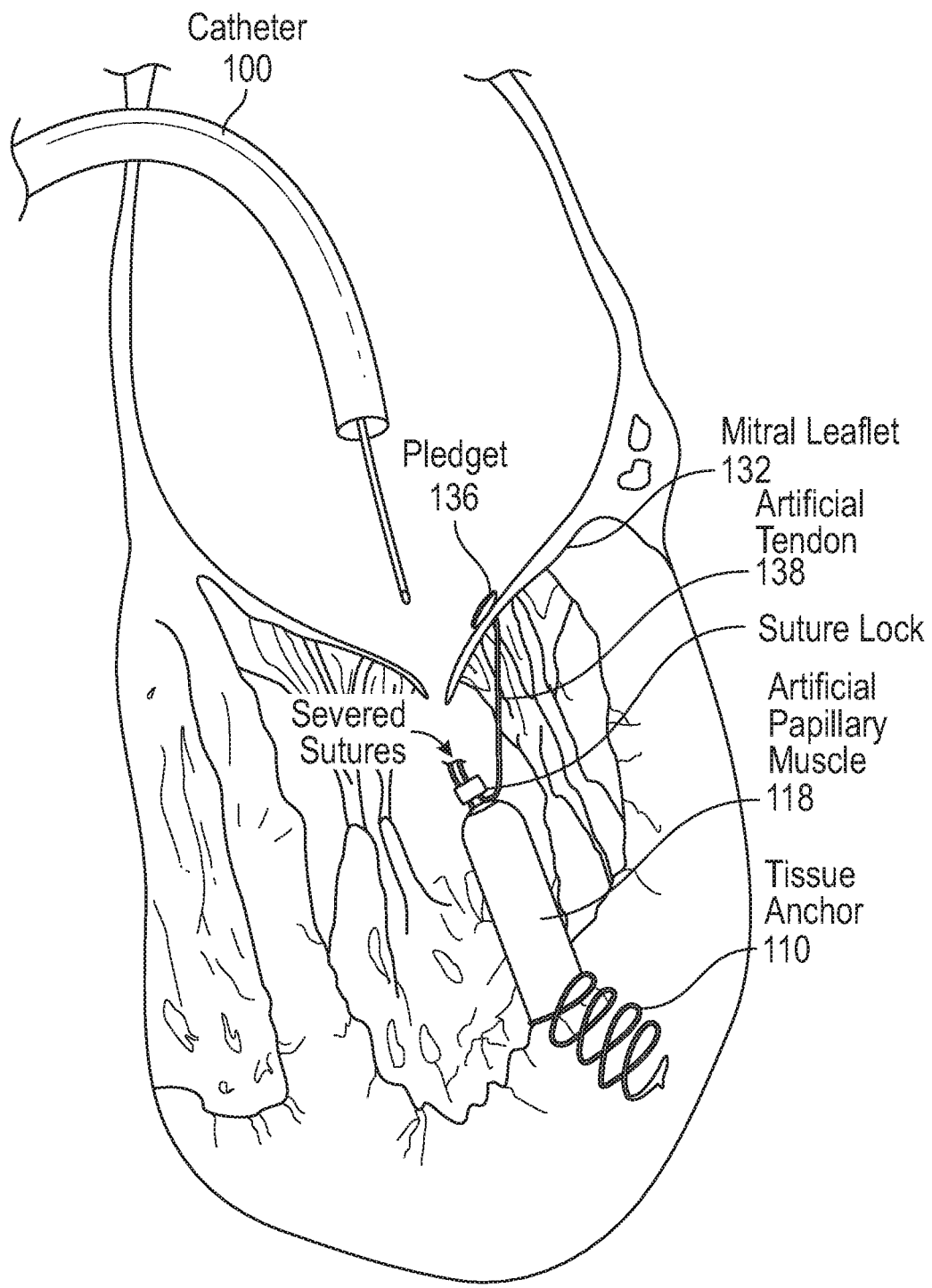
FIG. 35N illustrates severing of the leaflet suture and ventricle sutures, leaving the neo cord construct in place.

Referring to FIG. 35N, the leaflet suture 138 and anchor suture 114 may be severed proximally of the suture lock, using known techniques or techniques described elsewhere herein, and the catheter 100 may be withdrawn from the patient. This leaves a neo cord and neo papillary muscle construct in place within the left ventricle.

Figure 35O:
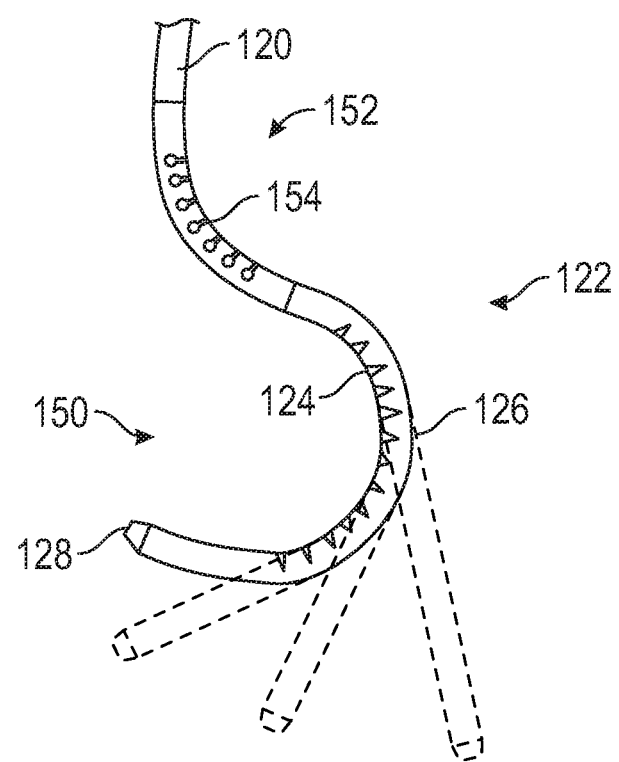
FIG. 35O illustrates a distal, steerable portion of a leaflet puncture catheter, having a compound deflected configuration.

Referring to FIG. 35O, there is illustrated a distal deflection zone 122 on a modified leaflet capture catheter 120. As with the deflection zone illustrated in FIG. 35C, the implementation of FIG. 35O includes a plurality of axially compressible slots 124 opposing a non-collapsible spine 126. Upon proximal retraction of a pull wire, this construct produces a primary concavity 150. As has been discussed, the shortest distance D at maximum flexion of the deflection zone 122 may generally be in the range of from about 0.5 to about 1.5 cm.

Depending upon the desired performance, there may be provided a secondary concavity 152 operable by axially collapsing the second plurality of slots 154. Flexion of the secondary concavity 152 may be accomplished by proximal retraction of a second pull wire. Alternatively, the primary concavity 150 and secondary concavity 152 may be simultaneously flexed by pulling a single pull wire.

In the illustrated embodiment, the secondary concavity 152 is concave in the same plane as, and in an opposite direction from the primary concavity 150. Alternatively, the second concavity 152 can be concave in the same direction as the primary concavity 150. In either configuration, the primary concavity may reside in a first plane, and the secondary concavity 152 may reside in a second plane rotationally offset from the first plane, depending upon the desired performance. Additional details of compound curvature catheter shafts can be seen in U.S. Patent Publication No. 2014/0243877, the disclosure of which is hereby incorporated in its entirety herein by reference.

Figure 36A:
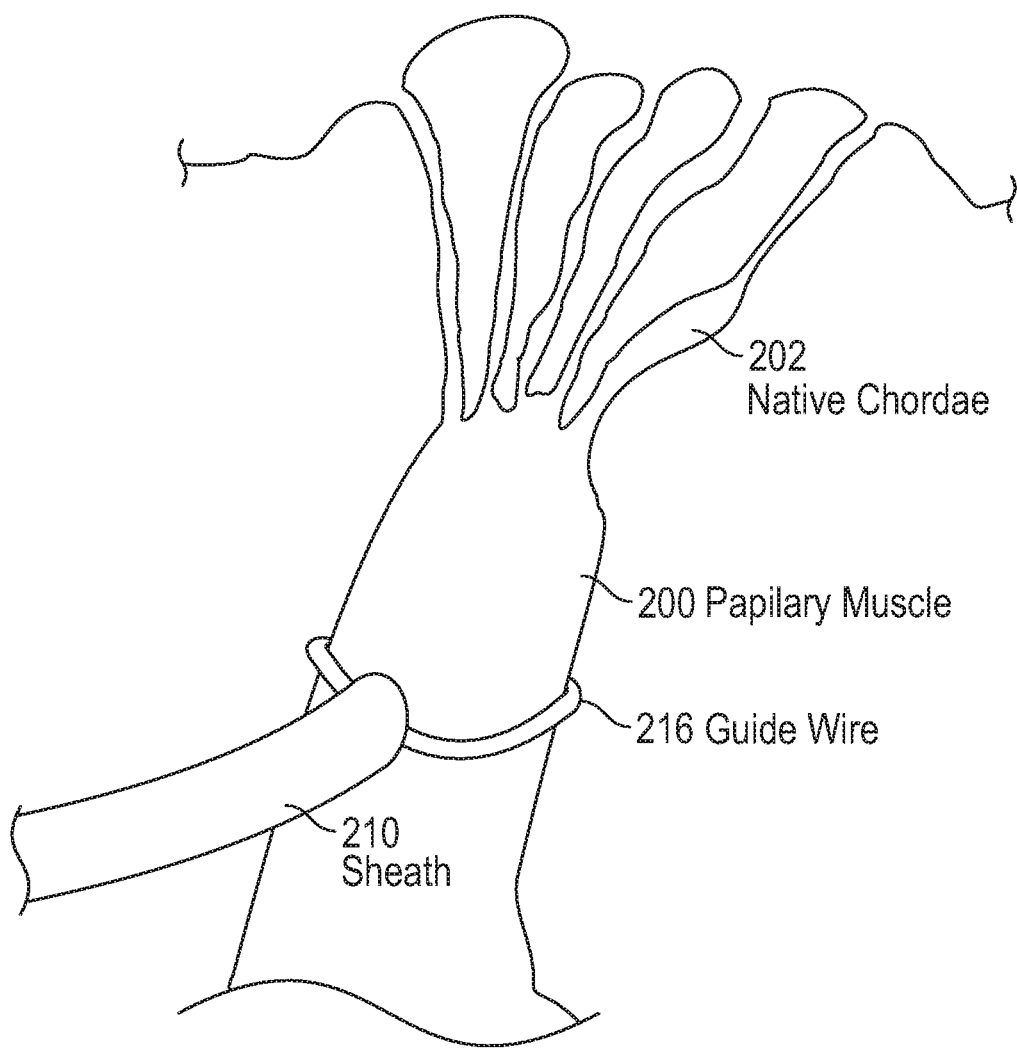
Figure 36B:
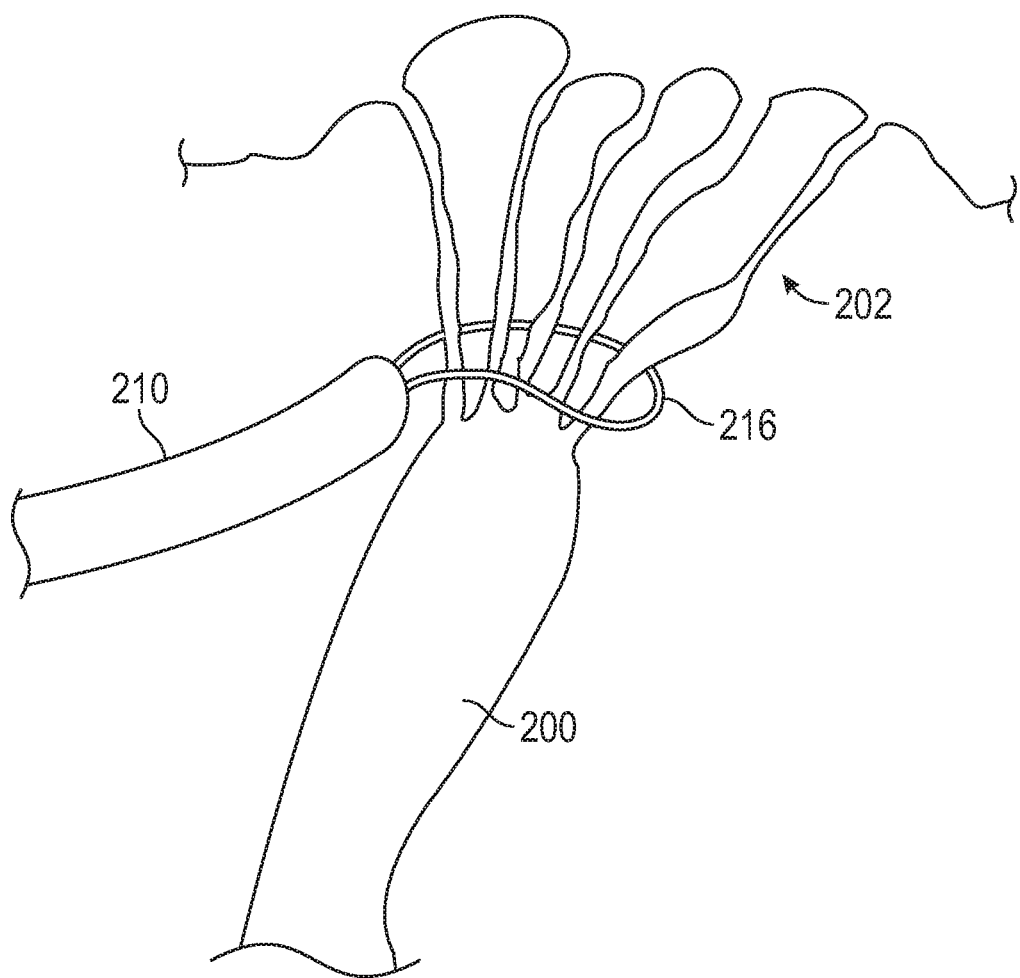
FIG. 36B shows the looped papillary pulled up onto the chords in an area where a cutting step is preferably performed.
Figure 37:
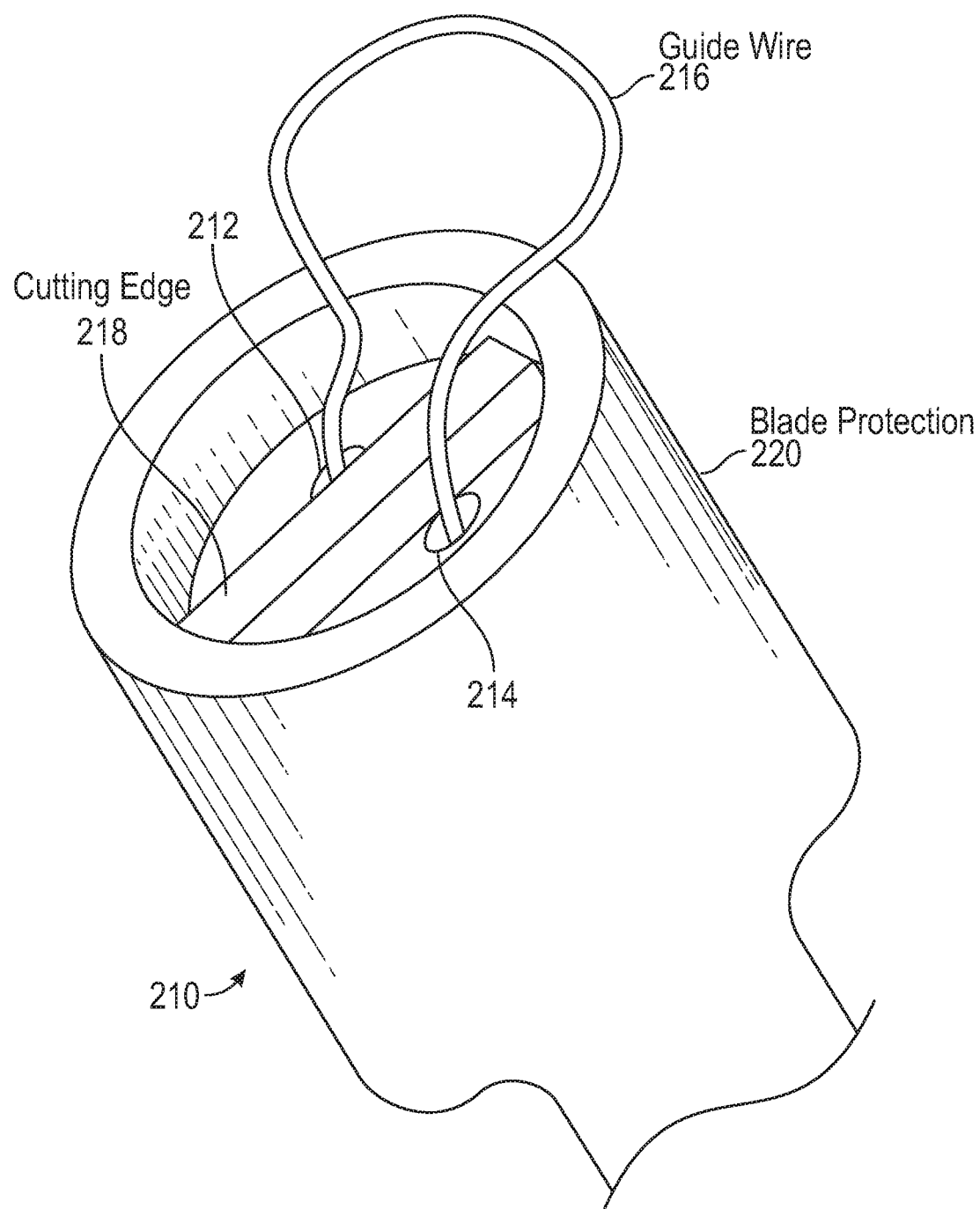
FIG. 37 illustrates one embodiment of a chordae cutting tool.

With reference now to FIGS. 36A-37, in some embodiments, rather than treating pure degenerative mitral regurgitation, embodiments of the method and devices disclosed here can also be used to treat a subset of patients with functional mitral regurgitation, where the patients have a tethered leaflet type of defect. In this anatomy, there is adequate length of the mitral valve leaflets for the leaflets to close and seal against leak, but the leaflets are not able to move up to the plane of the mitral annulus because the chordae are too short. This type of anatomy typically occurs because the annulus dilates and or the ventricle enlarges, while the chordae remain approximately the same length. Treatment of these patients can be performed by cutting all or a portion of the native chords as a step during the procedure.

In an embodiment, the chord cutting step is performed as the initial step, prior to the device implantation steps. This can prevent the possibility of accidental damage to the implant, but can create a condition of severe regurgitation during the procedure. Alternatively, the native chords can be cut at any point during the implantation of prosthetic chords, or after the other steps of implantation of the prosthetic chords is complete. Cutting as a final step can create the disadvantage that it may not be feasible to assess the exact result until after the chords have been implanted. The implanted device may be the same or similar to one of the embodiments disclosed herein.

In certain embodiments, the native chordae may be cut after placing the initial leaflet and ventricular anchors, but prior to final tensioning. In certain embodiments, this is achieved by first, prior to chord implantation, isolating the native chords by passing a guidewire around each papillary muscle, snaring the end of the wire and then advancing a sheath over the wire, in this way creating a snug loop around the papillary muscles. These loops can remain intact during the normal implantation of the ventricular and leaflet anchors. Once the ventricular and leaflet anchors are in place, using one of the devices and methods described here, and preferably partially tensioned, the native chords are cut. This can be achieved by manipulating the loops around the papillary muscles such that they move up past the papillary heads to the base of the chordae and cutting them. In one embodiment, the guidewire is simply pulled into the guide creating a cutting action. In another embodiment, a blade type tool that fits within the guide and has lumens for the guidewires is provided. By pulling both ends of the guidewire, the chordae are pulled against the blade and cut. Many other tissue cutting devices have been described in the art and would be applicable to the devices and method described here. After the native chordae are cut, the tension on the implant is adjusted. If the result is satisfactory it can be made permanent by locking the suture lock and cutting the suture tails as described in this application or by similar methods. If the result is not satisfactory, additional chordae may be added or other mitral repair procedures may be performed in conjunction.

Looping the papillary muscle instead of looping the chordae directly can ensure that all the chordae are captured, because all the normal chordae attach to the heads of the papillary muscles. Cutting using a looped guidewire is one method of cutting the native chordae but other methods and apparatuses can be used such as various types of transvascular suture cutters.

With reference now to FIGS. 36A-37, FIG. 36A is a picture of a looped papillary muscle 200 in the configuration it is first captured in. FIG. 36B shows the looped papillary 200 pulled up onto the chords 202 in the area where the cutting step is preferably performed. FIG. 37 illustrates one embodiment of the chordae cutting tool 210. The illustrated embodiment contains two lumens 212, 214, one for each end of a looped guidewire 216, a cutting edge 218 and an element 220 to protect the cutting edge 218 from contacting the sheath 210 and other portions of the device and patient that are not intended to be cut. The guidewire may be delivered through a first lumen 212 and a snare delivered through the second lumen 214 to snare the guidewire, after looping around the papillary muscle. The snare may withdraw the guidewire into the second lumen 214. As noted above, cutting using a looped guidewire is one method of cutting the native chordae but other methods and apparatuses can be used such as various types of transvascular suture cutters.

In some embodiments, the procedures described herein may be performed via specialized delivery systems and devices. The delivery systems may comprise multiple subcomponents configured for performing various steps of the procedure. In some implementations, a neo chordae tendinae deployment system, comprising an elongate, flexible tubular body such as catheter 100, may be used to access the heart of the patient (e.g., the left atrium). Multiple subsystems may be introduced into the heart via the delivery catheter 100. The subsystems may comprise catheters of smaller diameter than the internal lumen of the delivery catheter 100 such that they are configured to be inserted through the delivery catheter 100. In some implementations, some or all of the various subsystems may occupy the delivery catheter 100 simultaneously in order to perform the operations described elsewhere herein. In some implementations, some or all of the various subsystems may occupy the delivery catheter 100 in subsequent fashion in order to perform the operations described elsewhere herein. For example, the delivery system may comprise a ventricular anchor delivery system 300, a leaflet anchor delivery system 330, and/or a suture lock delivery system 370, as described elsewhere herein. FIGS. 38A-38H schematically illustrate a method of implanting a neo chordae tendinae via a delivery system comprising subsystems for ventricular anchor delivery, leaflet anchor delivery, and suture lock delivery. The procedure illustrated in FIGS. 38A-38H may be the same or substantially the same as that illustrated in FIGS. 35A-35O. In some embodiments, the neo chordae tendinae (or prosthetic chordae tendinae) comprises a suture, as illustrated in FIGS. 38A-38H. In other embodiments, the neo chordae tendinae may be another flexible element. The flexible element may be attached to a suture at its proximal end and/or its distal end for coupling to the ventricular anchor and/or the leaflet anchor.

Figure 38A:
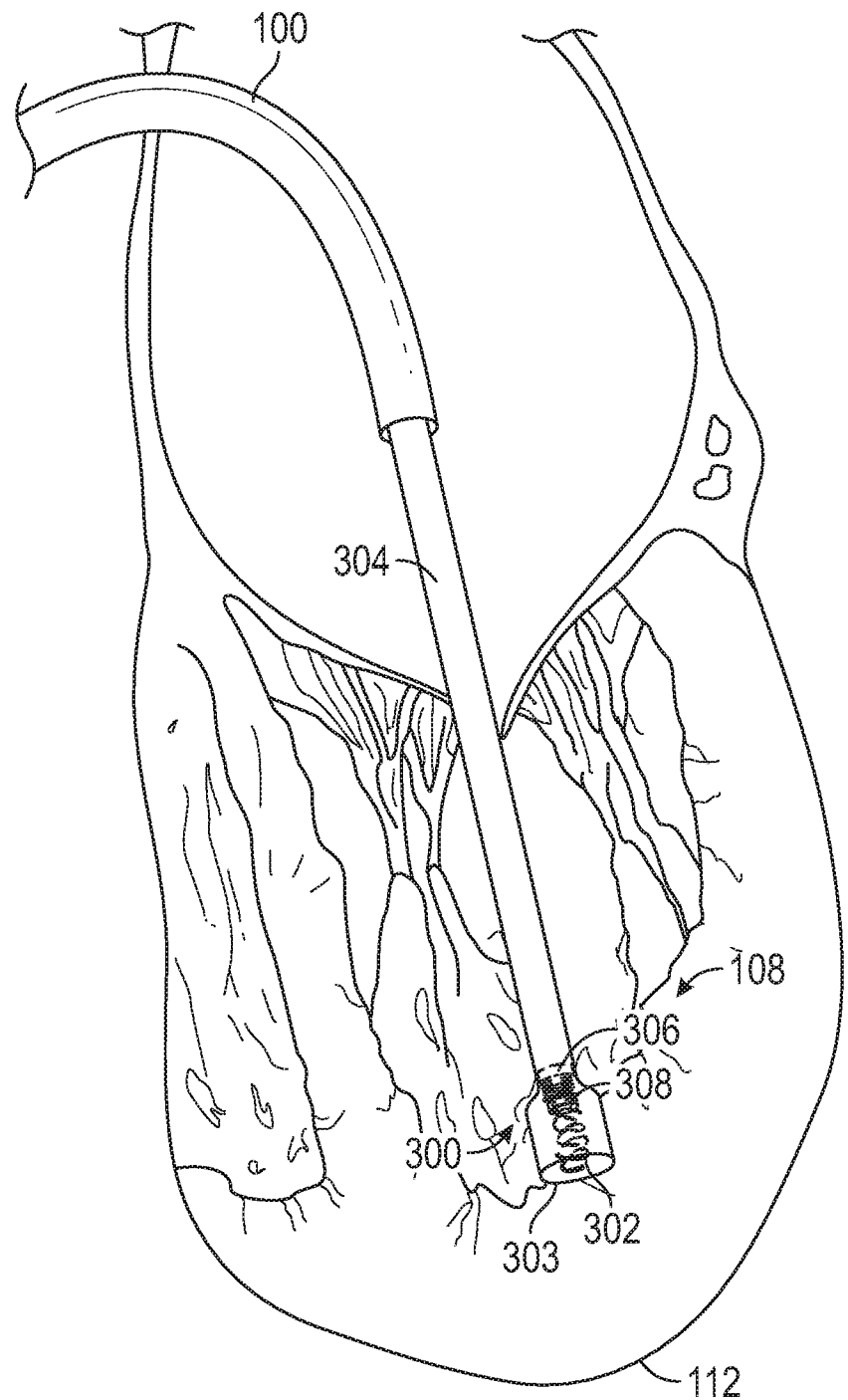
FIG. 38A depicts the installation of a helical anchor near the apex of the left ventricle via a ventricular anchor delivery subsystem.

FIG. 38A depicts the installation of a helical anchor 302 near the apex 112 of the left ventricle 196. While the helical anchor 302 is shown positioned near the apex 112 in the following figures, the anchor 302 can be attached at a point that is offset from the thin tissue of the apex, and can be instead implanted in the generally thicker adjacent wall of the ventricle, such as between the two papillary muscles. Positioning the anchor is preferably also such that the longitudinal axis of the implanted neo chord construct is aligned approximately parallel to or concentric with the original path of the native chord. In such arrangements, the tissue anchor 302 can be positioned in left ventricle between the papillary muscles as shown, for example, in see FIG. 42. In addition, while a helical anchor is illustrated the anchor can have a different structure for engaging tissue of the heart and thus as explained above other structures can be use instead of a helical structure including various piercing or hook structures for engaging tissue.

Figure 39A:
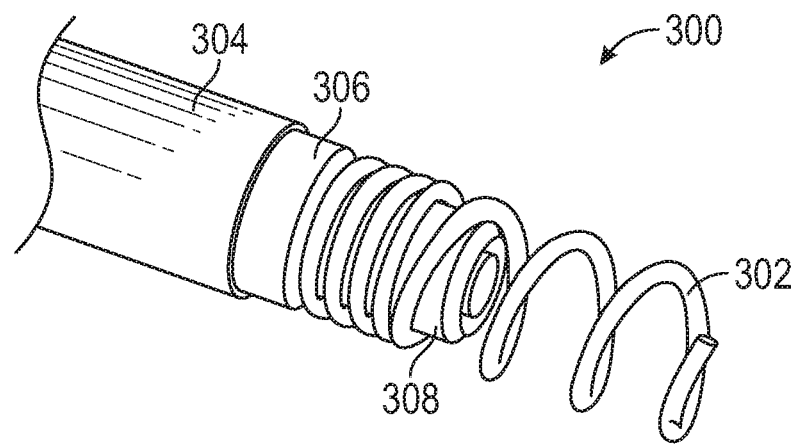
FIG. 39A depicts a perspective view of a distal end of the ventricular anchor delivery subsystem.
Figure 39B:
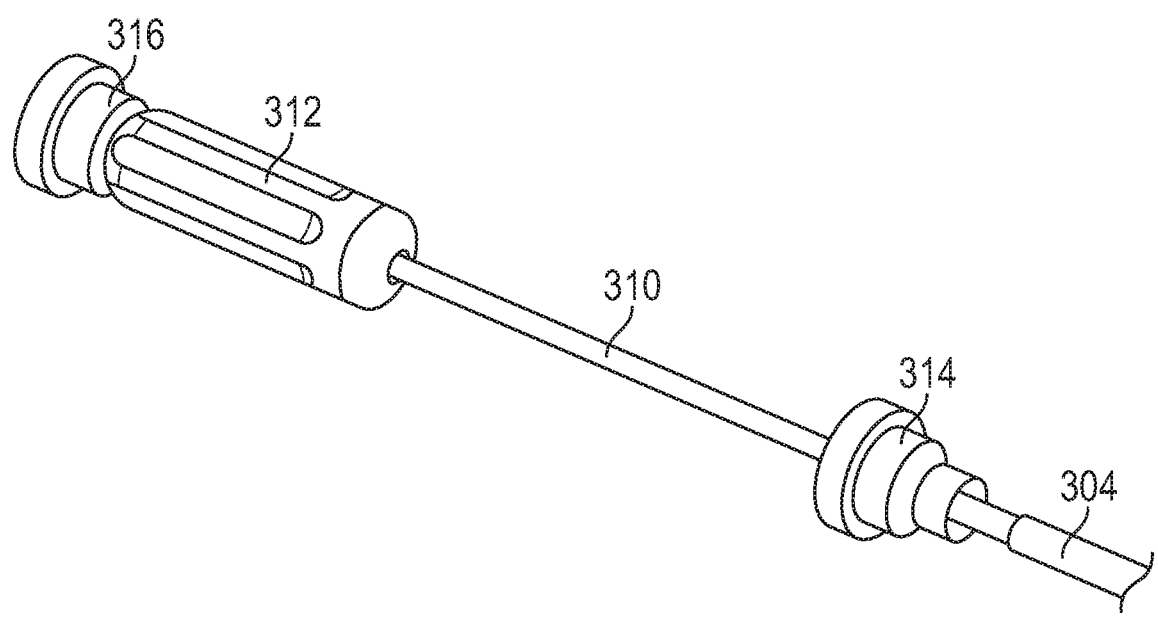
FIG. 39B depicts a perspective view of a proximal end of the ventricular anchor delivery subsystem.
Figure 39C:
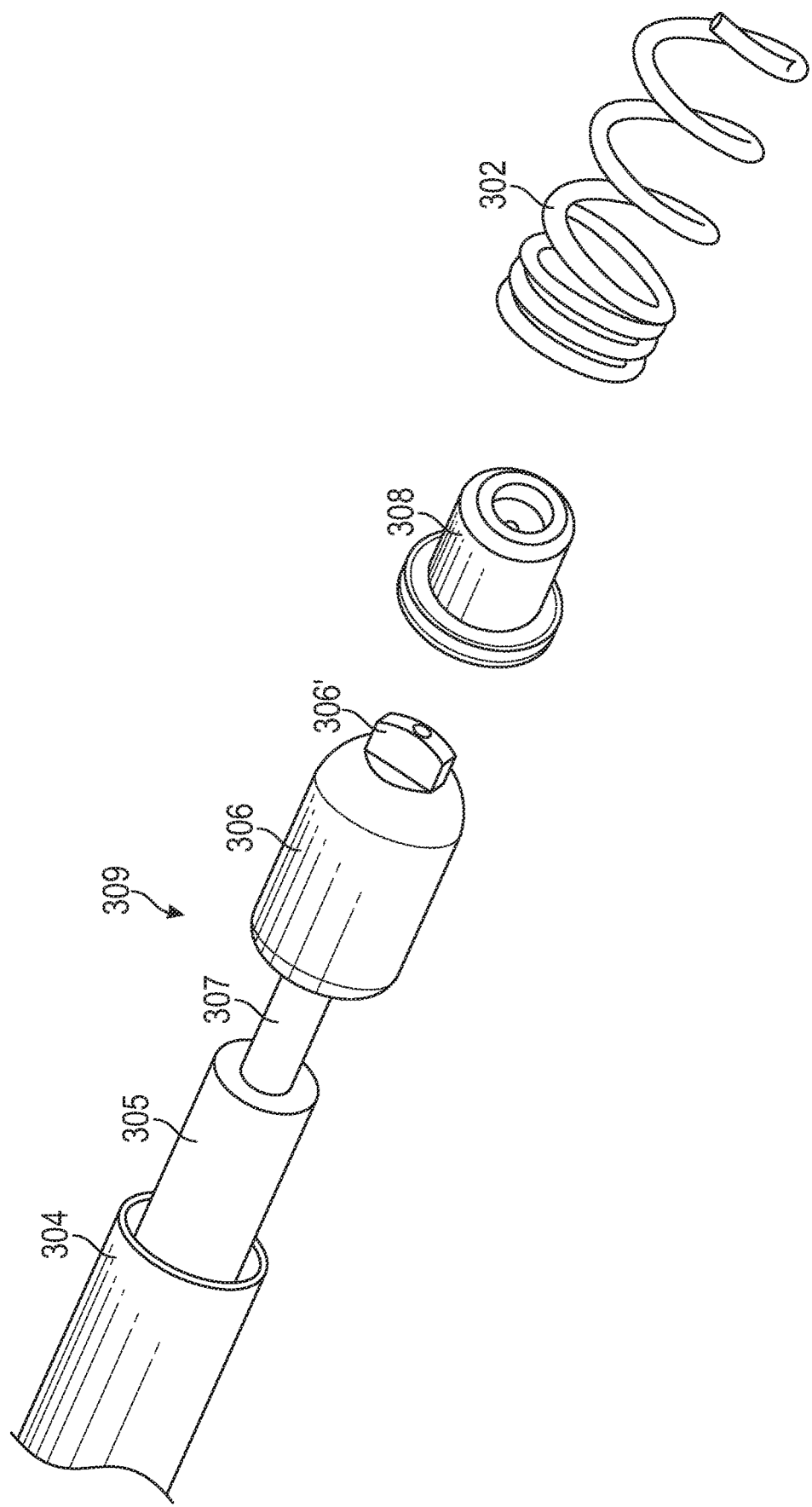
FIG. 39C depicts a partially exploded view of a distal end of the ventricular anchor delivery subsystem.

The helical anchor 302 may be delivered by a ventricular anchor delivery subsystem 300. FIGS. 39A-39C illustrate various views of the ventricular anchor delivery subsystem 300 and its components. FIG. 39A depicts a perspective view of a distal end of the subsystem 300. FIG. 39B depicts a perspective view of a proximal end of the subsystem 300. FIG. 39C depicts a partially exploded view of a distal end of the subsystem 300. The subsystem 300 may be delivered through the delivery catheter 100. The delivery catheter 100 may access the left atrium through conventional techniques, such as through an atrial trans-septal puncture. The delivery catheter 100 may be maintained in a substantially constant location throughout the procedure as various subsystems are placed and removed from the delivery catheter 100. For instance, the distal end of the delivery catheter 100 may be positioned in the left atrium. In other implementations, the distal end of the delivery catheter 100 may be positioned in the left ventricle throughout the duration of the procedure.

As shown in FIGS. 39A and 39C, the ventricular anchor delivery subsystem 300 may comprise an outer sheath 304, a guide shaft 305, a driver 309 (comprising shaft 307 and head 306), an anchor hub 308, and an anchor. The anchor may be a helical anchor 302 and the drive 309 can be configured to rotate the anchor 302 such that the driver 309 is configured to rotate the helical anchor 302. The helical anchor 302 may comprise an inner diameter configured to be received over the outer diameter of an anchor hub 308. The helical anchor 302 may be securely fixed secured to the anchor hub 308 by an interference fit or other frictional engagement. The anchor hub 308 may be left implanted along with the helical anchor 302. The anchor hub 308 may comprise a lumen positioned substantially along a central axis of the anchor hub 308 for receiving a suture 311 (not shown) and attaching the suture 311 to the helical anchor 302. In some embodiments, the suture 311 may comprise an attachment element (e.g. a knot or a washer) with a diameter sized to prevent the suture 311 from being pulled proximally through the anchor hub 308 lumen. For example, the suture 311 may be knotted on a distal side of the lumen. In some embodiments, the suture 311 may be tied to the anchor hub 308 (e.g., passed through the lumen, wrapped around the outer surface, and tied to itself). The helical anchor 302 may comprise a distal section of windings and a proximal section of windings. The proximal section of windings may be spaced closer together than the distal section of windings and may be configured for securing the helical anchor 302 to the anchor hub 308. The distal section of windings may be spaced further apart than the proximal section of windings and may be configured for insertion into the ventricular tissue. The anchor hub 308 may comprise an enlarged cross-section at its proximal end configured to abut the helical anchor 302 and/or prevent the helical anchor 302 from advancing proximally over the proximal end of the anchor hub 308. Other helical anchors, such as those described elsewhere herein, may be configured to be used with the ventricular anchor delivery subsystem 300 described herein as well.

The proximal face of the helical anchor 308 may comprise a recess for receiving an extending portion 306' of the driver head 306. The recess may be non-circular (e.g., oblong or polygonal) such that it is configured to transfer torque from the driver 309 to the anchor hub 308 upon rotation of the driver 309. The recess may be positioned around the central lumen of the anchor hub 308. In other embodiments, the anchor hub 308 may comprise an extending portion and the driver 306 may have a recess. The driver head 306 may be generally cylindrical. The driver head 306 may be fixedly coupled to a drive shaft 307. The driver 309 may comprise a central lumen through the driver head 306 and drive shaft 307 configured to receive the suture 311. The central lumen of the driver 309 may be configured to be aligned with the central lumen of the anchor hub 308. The drive shaft 307 may be received within a guide shaft 305. The diameter of the driver head 306 may be larger than the inner diameter of the guide shaft 305. The outer sheath 304 may be sized to receive the guide shaft 305 as well as the driver head 306, the anchor hub 308, and the helical anchor 302.

The outer sheath 304 may be delivered into the left ventricle and proximal to the ventricular attachment site via the delivery catheter 100. In some embodiments, the outer sheath 304 may be delivered without a delivery catheter. In some implementations, the helical anchor 308 may be concealed within the outer sheath 304 until the outer sheath 304 is positioned proximal to the ventricular attachment site then pushed distally through the outer sheath 304 so that the helical anchor 302 is exposed. The helical anchor 302 may be placed into contact with the ventricular tissue. Rotation of the drive shaft 307 may cause the driver head 306, the anchor hub 308, and the helical anchor 302 to rotate thereby screwing the ventricular anchor 302 into the ventricular tissue. Rotation of the driver 309 may axially advance the driver 309, anchor hub 308, and helical screw 302 in a distal direction with respect to the outer sheath 304. The drive shaft 307 may be rotated manually by a user using a drive handle 312, as shown in FIG. 39B. The proximal end of the ventricular anchor delivery subsystem 300, as illustrated in FIG. 39B, may comprise first and second hemostasis valves 314, 316. The first hemostasis valve 314 may be positioned distal to the drive handle 312 and may provide access to the guide shaft 305. The second hemostasis valve 316 may be positioned proximal to the drive handle 312 and may provide access to the central lumen of the driver. The ventricular anchor suture 311 may extend through the second hemostasis valve 316.

In some embodiments, the ventricular delivery subsystem 300 may include a shield or guard 303 (shown in FIG. 38A) positioned around the distal end of the outer sheath 304. Guard 303 may comprise a tubular wall attached to or advanceable out of the tubular sheath 304, having an open distal end. The guard 303 may be enlargeable from a first, reduced cross section for transluminal navigation, to a second, enlarged cross section for permitting rotation of the anchor therein.

The guard 303 may have an increasing diameter in the distal direction such that the inner diameter of the guard 303 is larger at the distal end of the guard 303 than the outer diameter at the distal end of the outer sheath 304. The expanded diameter of the guard 303 may provide sufficient space for rotation of the helical anchor 302 without contacting an inner surface of the guard 303. The guard 303 may be placed into contact with the ventricular tissue or positioned in close proximity to the ventricular tissue during installation of the helical anchor 302. The guard 303 may advantageously prevent chordae or other tissue adjacent to the helical anchor 302 from getting caught up in the windings of the helical anchor 302 during rotational insertion of the helical anchor 302. Once the helical anchor 302 is inserted into the ventricular tissue an adequate depth, the driver 309 may be withdrawn from the anchor hub 308 such that the helical anchor 302 is disengaged from the remainder of the ventricular anchor delivery subsystem 300.

In some implementations, the inserting portion 306' of the driver head 306 and the recess of the anchor hub 308 may have a frictional engagement that transiently holds the two components together. The frictional engagement may be overcome upon proximal retraction of the driver by a counter force from the ventricular tissue once the helical anchor 302 is inserted. In some implementations, proximal tension on the suture 311 may provide an engagement force between the proximal hub 308 and the driver head 306, which can be released upon retraction of the driver 309. The driver head 306 may be proximally withdrawn into the outer sheath 304 before the outer sheath 304 is withdrawn into the delivery catheter 100.

The non-implanted components of the ventricular anchor delivery subsystem 300 may be removed from the delivery catheter 100 and subsequent subsystems may be placed in the delivery catheter 100 for completing implantation of the neo chordae. In a modified embodiment, the ventricular anchor delivery subsystem 300 and subsequent subsystems such as the leaflet anchor delivery subsystem 330 may be positioned within the delivery catheter 100 at the same time and in certain arrangement the tissue and leaflet anchors can both be preloaded into the delivery catheter. In alternative embodiments, the implantation of the ventricular anchor may be performed in a different order (e.g., after the implantation of the leaflet anchor). The ventricular anchor delivery components may be proximally retracted over a proximal end of the suture 311, which may remain extending through the delivery catheter 100 to the ventricular anchor 302. FIGS. 38A-38H depict installation of a neo chordae without a neo papillary muscle 116, as depicted, for example, in FIG. 35A. However, the procedure may also be performed in combination with a neo papillary muscle 116. The neo papillary muscle 116 may be advanced over the suture 311, for example, after installation of the ventricular anchor 302. In some embodiments the neo papillary muscle may be coupled to the anchor hub 308.

FIGS. 38B-38F depict various steps comprising the installation of the leaflet anchor via a leaflet anchor delivery subsystem 330. The leaflet anchor may be delivered after the installation of the ventricular anchor. The leaflet anchor delivery subsystem 330 may be delivered through the delivery catheter 100 alongside the ventricular anchor suture 311 which remains connected to the ventricular anchor 302. In some embodiments, the leaflet anchor may be delivered prior to the installation of the ventricular anchor 302. The leaflet delivery subsystem 330 may alternatively be delivered through the ventricle wall such as transapically into the left ventricle, or transseptally from the right ventricle to the left ventricle.

Figure 40A:
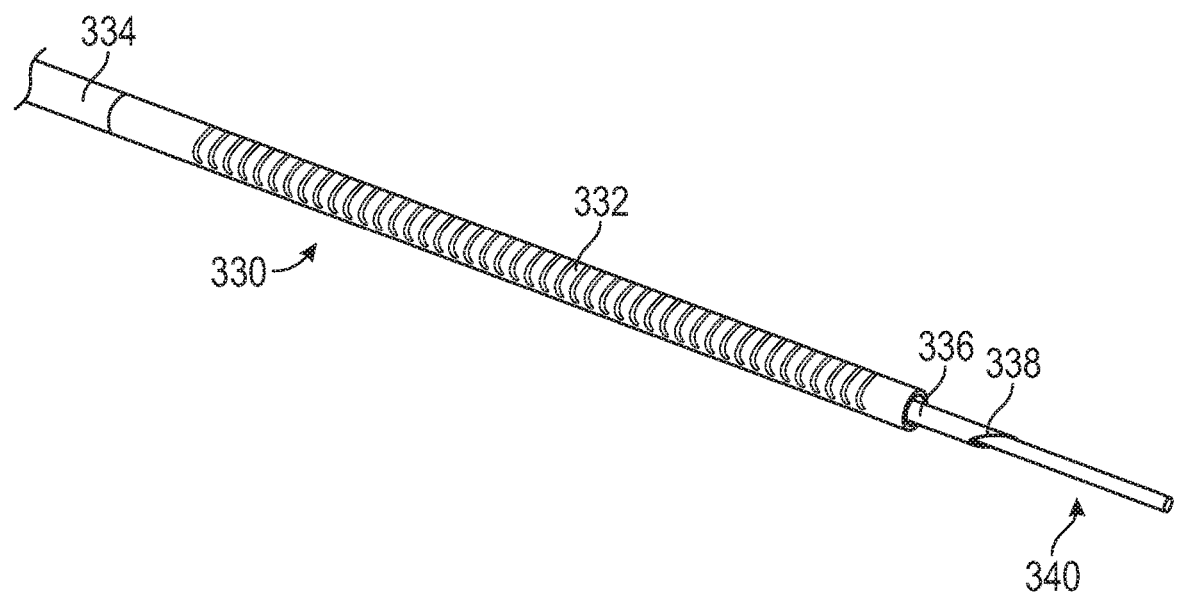
FIG. 40A depicts a perspective view of a distal end of the leaflet anchor delivery subsystem.
Figure 40B:
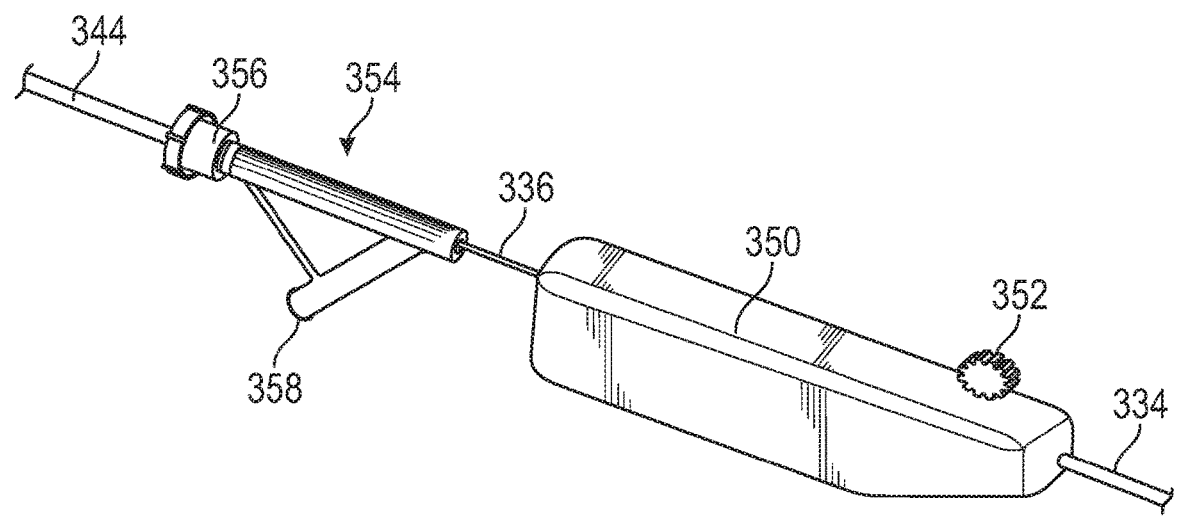
FIG. 40B depicts a perspective view of a proximal end of the leaflet anchor delivery subsystem.
Figure 40C:
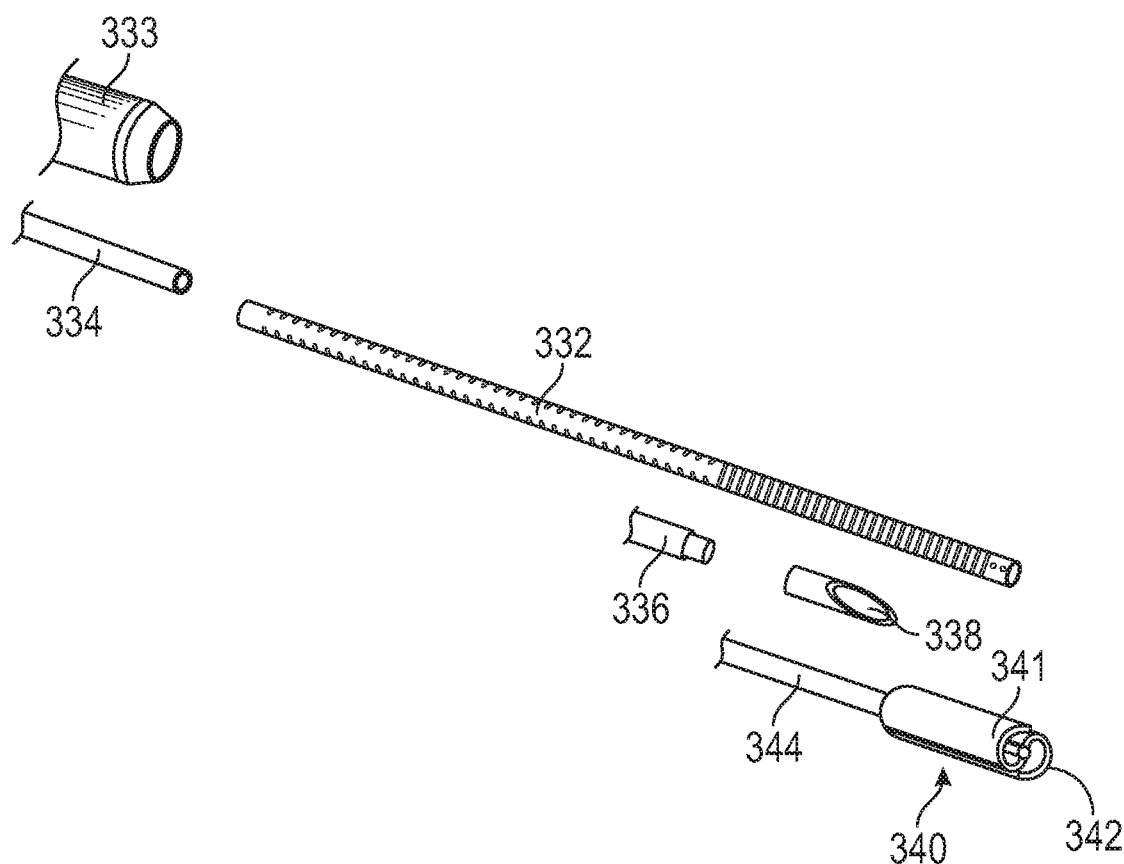
FIG. 40C depicts an exploded view of the distal end of the leaflet anchor delivery subsystem.
Figure 40D:
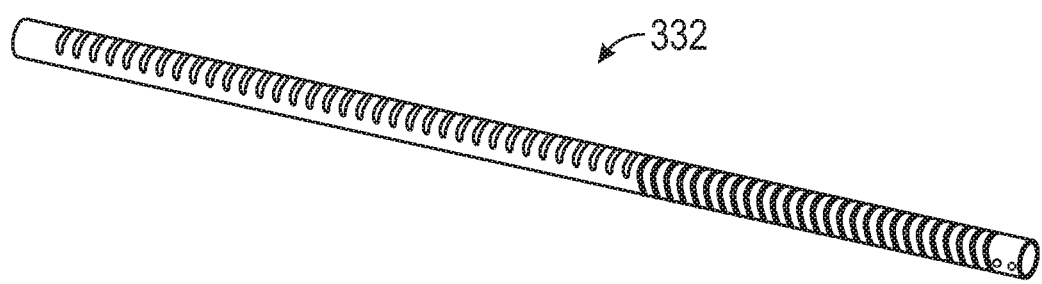
FIG. 40D depicts a perspective view of a flex tube of the leaflet anchor delivery subsystem.
Figure 40E:
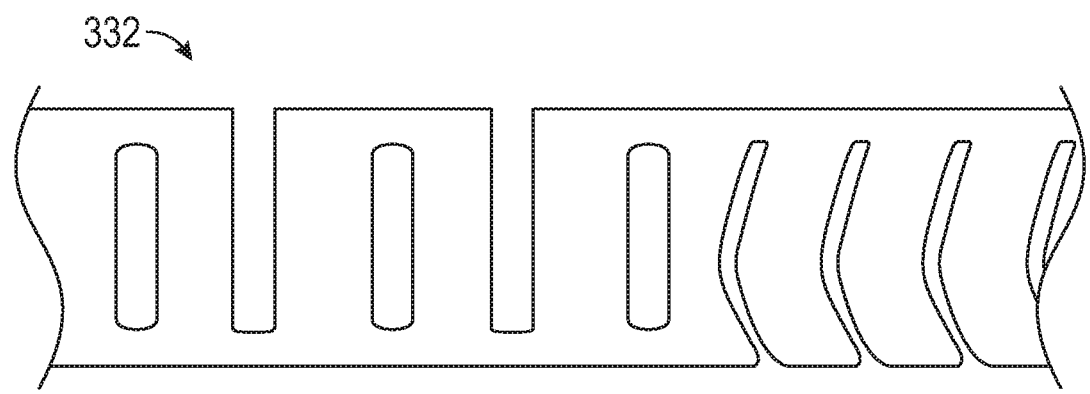
FIG. 40E depicts a side view of a transition region of the flex tube of the leaflet anchor delivery subsystem.
Figure 40F:
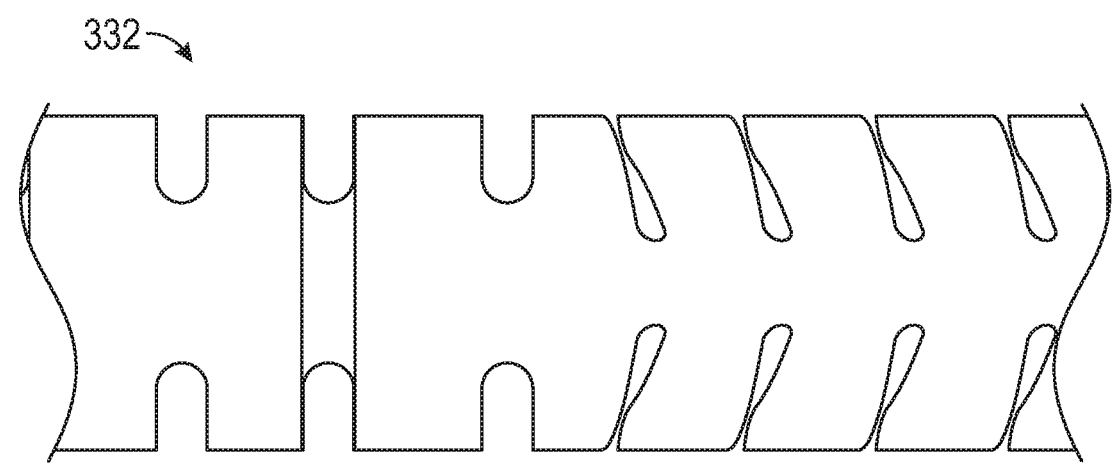
FIG. 40F depicts an orthogonal side view from that depicted in FIG. 40E of the transition region of the flex tube of the leaflet anchor delivery subsystem.

FIGS. 40A-40F illustrate various views of the leaflet anchor delivery subsystem 330 and its components. FIG. 40A depicts a perspective view of a distal end of the subsystem 330. FIG. 40B depicts a perspective view of a proximal end of the subsystem 330. FIG. 40C depicts an exploded view of the distal end of the subsystem 330. FIG. 40D depicts a perspective view of a flex tube 332. FIGS. 40E and 40F depict different side views of a transition region of the flex tube 332.

As shown in FIGS. 40A and 40C, the leaflet anchor delivery subsystem 330 may comprise a delivery shaft 334. A deflectable flex tube 332 may be coupled to the distal end of the delivery shaft 334. FIG. 40D depicts one implementation of the flex tube 332. The deflectable flex tube 332 may form a deflection zone 122 as described elsewhere herein. The deflectable flex tube 332 may be configured to be steerable by an operator as described elsewhere herein, such as by proximal retraction of one or two or more pull wires (not shown) along various sides of the flex tube 332. The operator may control the flexion of the flex tube via a knob 352 or lever or other actuation mechanism positioned on a handle 350 at the proximal end of the leaflet anchor delivery subsystem 330, as shown in FIG. 40B.

As shown in FIG. 40D, the flex tube may comprise transverse slots. The transverse slots may be positioned at various lengths of the flex tube 332 substantially opposite a side of the flex tube 332 comprising no apertures or slot to form a relatively stiff or axially incompressible spine. The axial spacing of the transverse slots, the axial width of the transverse slots, the shape of the transverse slots, the circumferential orientation of the transverse slots, and/or the circumferential length of the transverse slots may affect the degree of flexibility and/or the direction the flex tube 332 is prone to flex at a local area or generally along the overall length of the flex tube 332.

The flex tube 332 may comprise two or more sections along the length of the flex tube 332 having different patterns of transverse slots and/or different flexing properties. For example, the flex tube 332 depicted in FIG. 40D comprises a proximal section and a distal section having different patterns of transverse slots. FIGS. 40E and 40F show close up side views of the flex tube 332 near the transition between the proximal section and the distal section. The views in FIGS. 40E and 40F are approximately 90 degrees rotationally offset from each other with respect to the longitudinal axis of the flex tube 332.

Figure 38B:
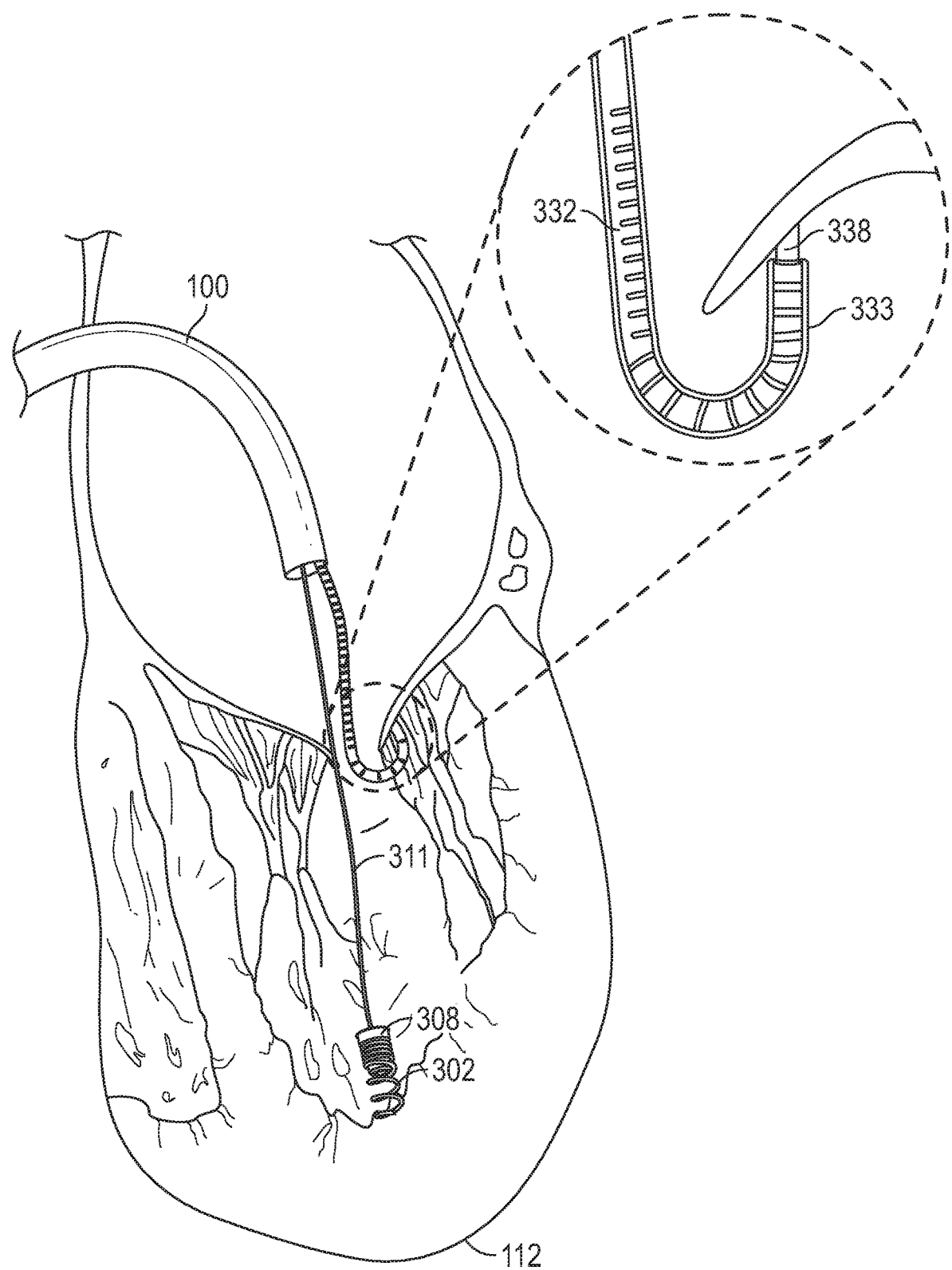
FIG. 38B depicts positioning a leaflet anchor delivery subsystem on the ventricular side of the leaflet using a distal flex tube.

The flex tube 332 may be used to steer or guide the distal end of the leaflet anchor delivery subsystem 330 to the leaflet. The flex tube 332 may be especially advantageous for positioning the distal end on the ventricular side of the leaflet when the subsystem is delivered to the heart from the right atrium. As shown in FIG. 38B, the distal end of the leaflet anchor delivery subsystem 330 may be deflected (e.g., at least approximately 180 degrees) such that proximal retraction of the subsystem exerts pressure on the ventricular surface of the leaflet. The radius or best fit radius of curvatures of the deflected flex tube 332 is generally less than about 2 cm, and preferably less than about 1.5 cm or 1.0 cm.

A flexible jacket 333 may surround the flex tube 332 and the delivery shaft 334. An internal flexible shaft 336 terminating at a distal end with a needle point may extend through the delivery shaft 334 and the flex tube 333. The internal flexible shaft 336 may comprise a braided tube or catheter which is flexible enough to conform to the shape of the flex tube 332. A needle tip 338 may be coupled to the distal end of the internal flexible shaft 336. The proximal end of the internal flexible shaft 336 may be connected to a needle handle 354, as shown in FIG. 40B. The needle handle 354 may comprise a hemostasis valve 356. The leaflet suture 344 may be inserted through valve 356. Valve 356 may be a touhy. The needle handle 354 may include additional ports 358 for accessing the lumen of the internal flexible shaft 336. The needle handle 354 may be positioned proximally to the handle 350 such that the internal flexible shaft 336 extends through the handle 350 and into the lumen of the delivery shaft 334. The handle 350 may comprise a hemostasis valve for receiving the internal flexible shaft 336 and sealing the internal components of the handle, including the opening to the delivery shaft 334, from the ambient environment. The needle 338 may be extendable and retractable by extending the needle handle 354 toward the handle 350 or retracting the needle handle 354 from the handle 350, respectively.

Figure 38C:
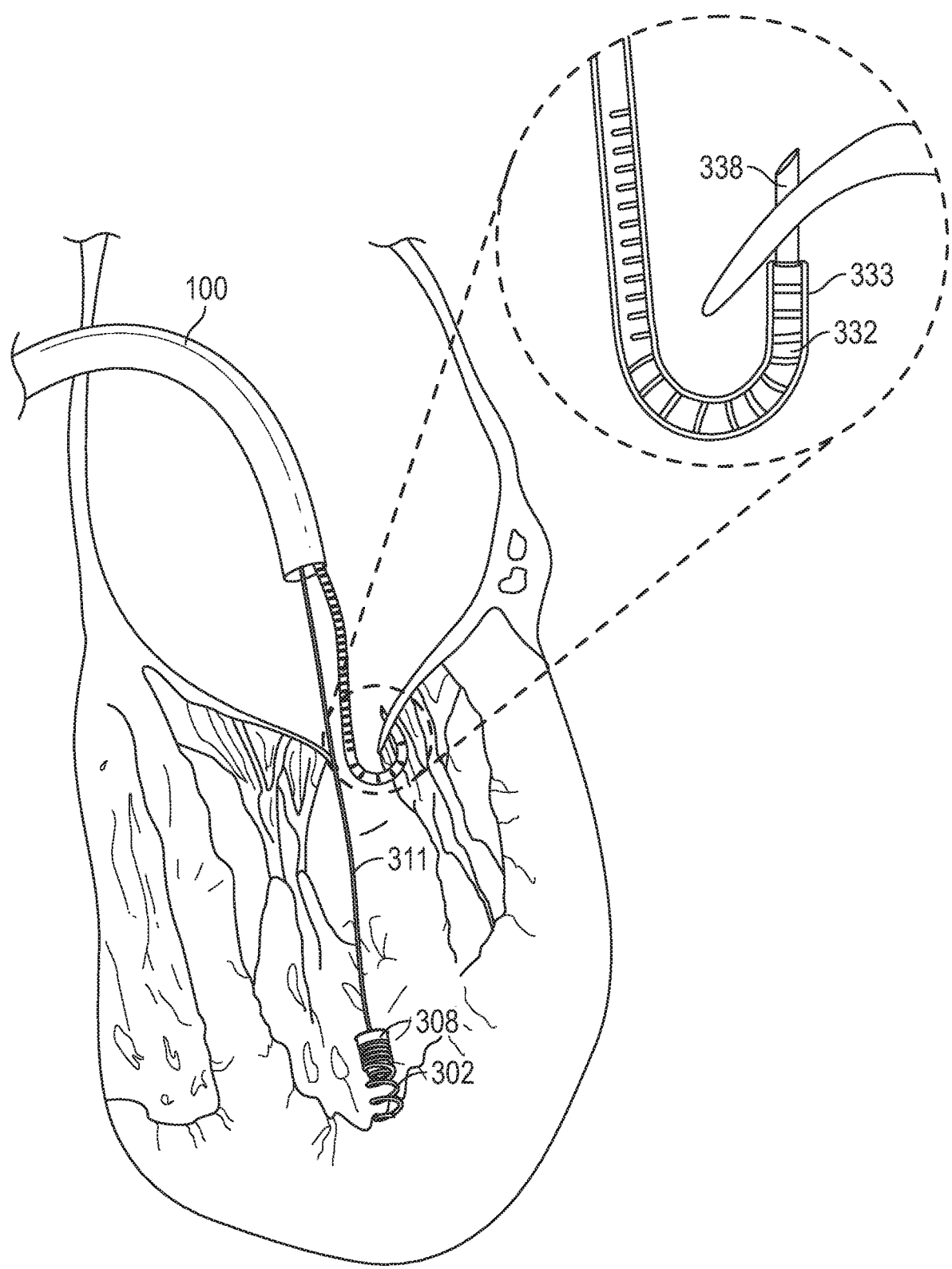
FIG. 38C depicts piercing the leaflet using a needle disposed at the distal end of the ventricular leaflet delivery subsystem.

Exertion of pressure on the leaflet when the needle tip 338 is extended distally beyond the flex tube 332 and the flexible jacket 333 may cause the needle tip 338 to puncture the leaflet such that the needle tip 338 may extend through to the opposite side (e.g., the atrial side) of the leaflet, as shown in FIG. 38C. This pressure may be exerted by extending the needle tip 338 and/or retracting the entire delivery device 330 in a proximal direction with the needle tip 338 in an extended position.

Figure 38D:
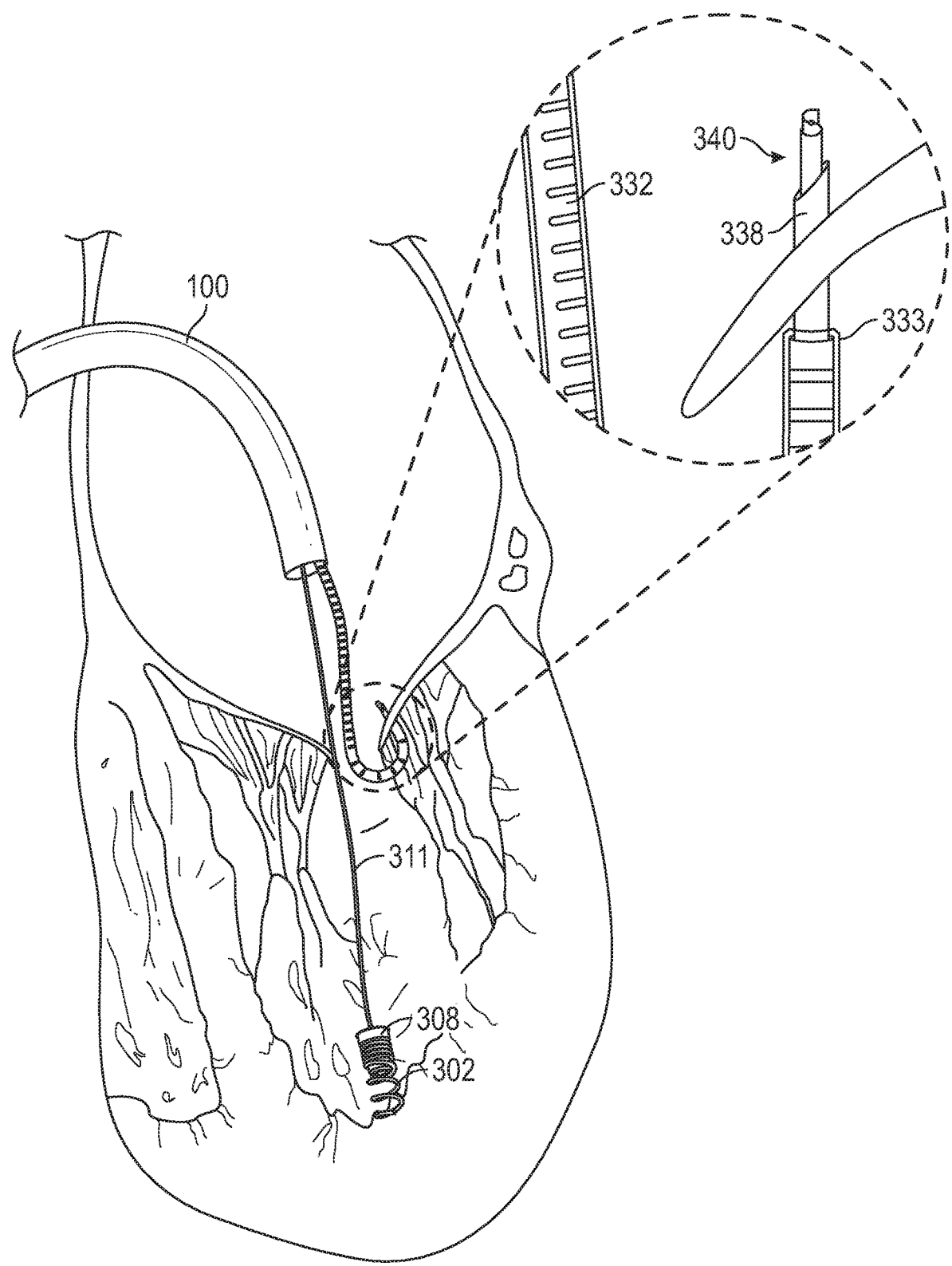
FIG. 38D depicts advancing a pledget leaflet anchor through the needle in a reduced radial cross section conformation.
Figure 38E:
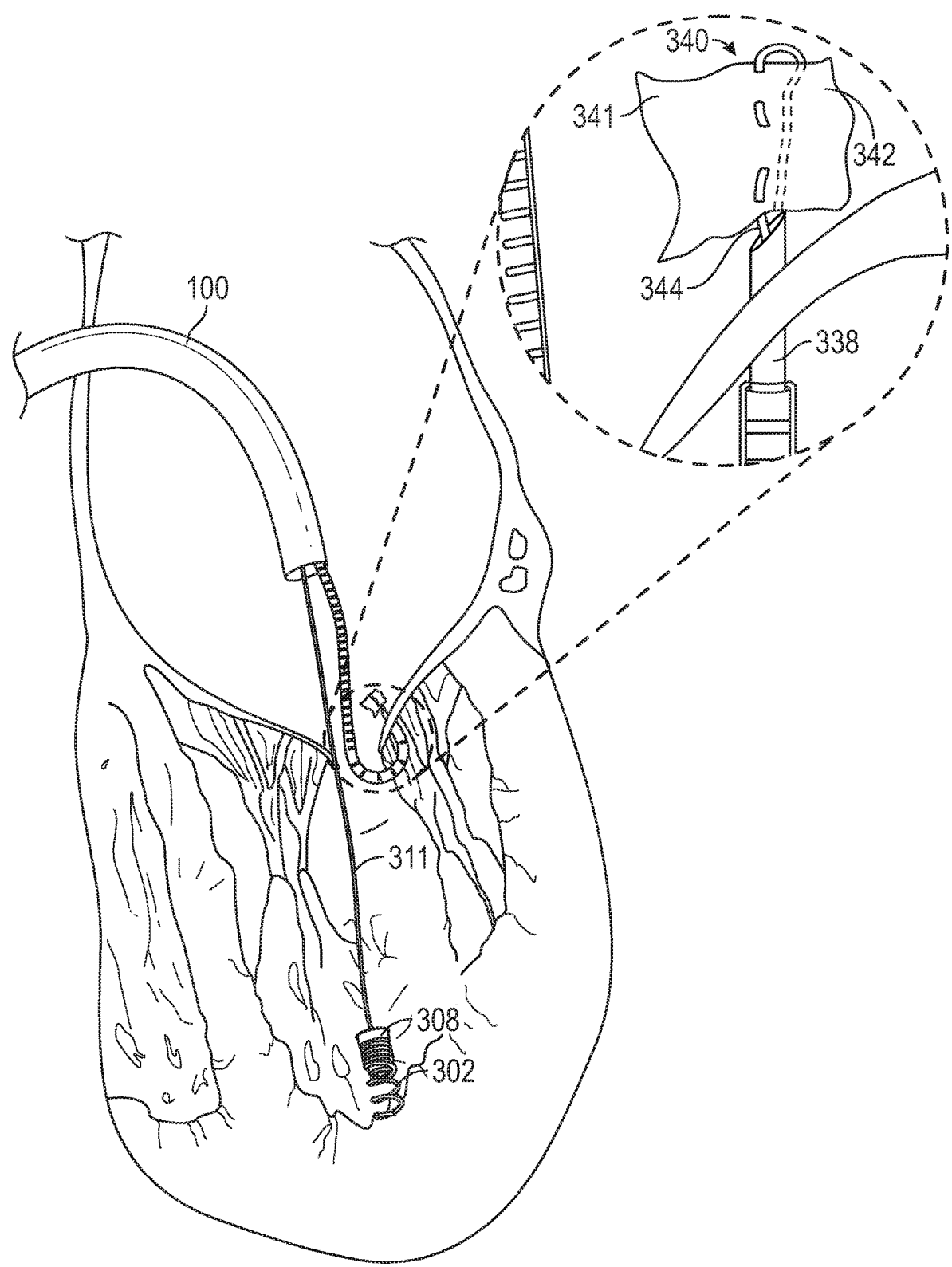
FIG. 38E depicts the pledget leaflet anchor expanding to an expanded radial cross section conformation.
Figure 38F:
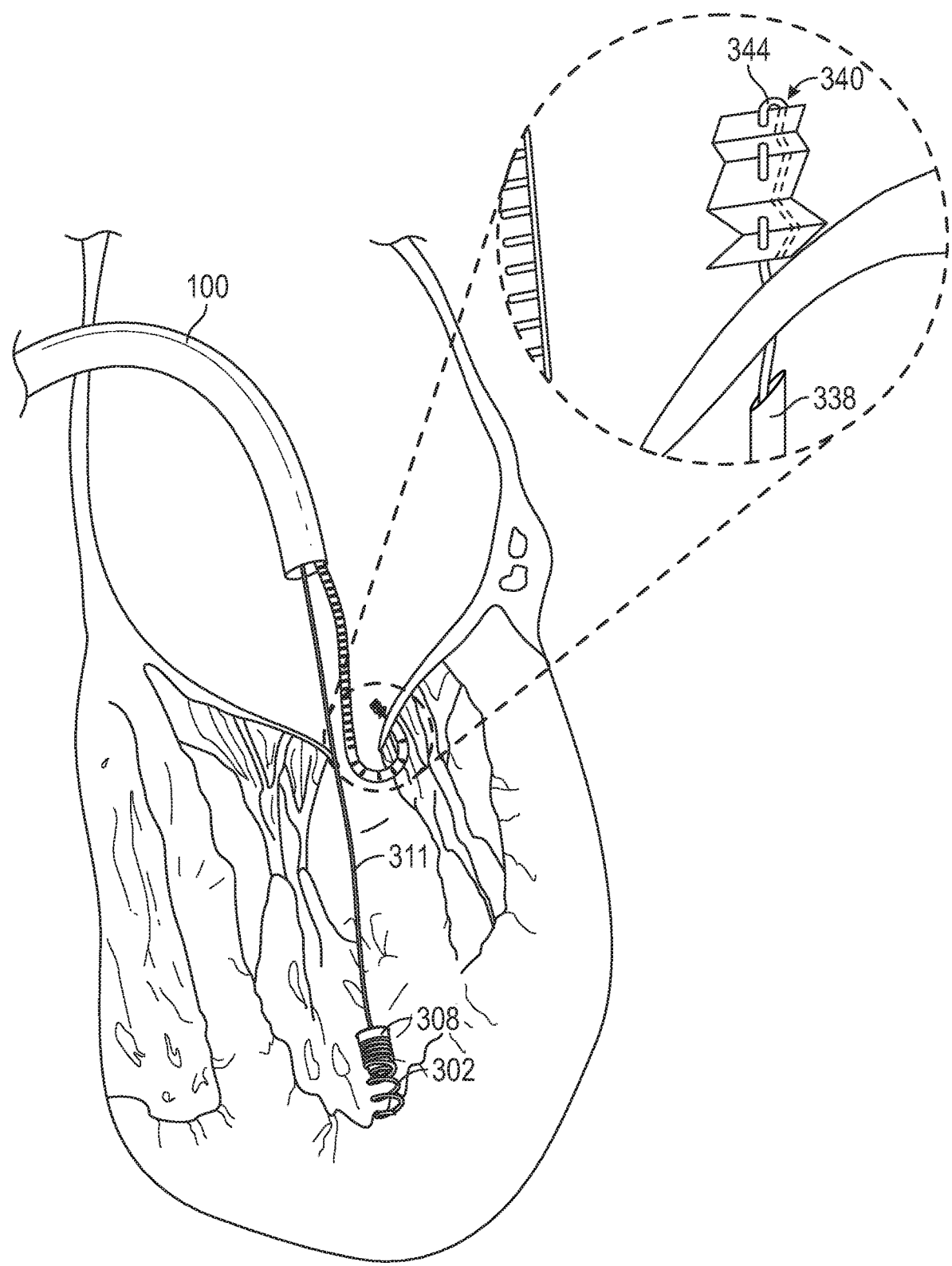
FIG. 38F depicts the pledget leaflet anchor being folded into a collapsed configuration for anchoring the suture against the atrial side of the leaflet.

FIGS. 38D-38F depict the deployment of the leaflet anchor. The leaflet anchor may be a pledget 340 similar to those described elsewhere herein. The pledget 340 may be coupled or attached to the distal end of a suture 344. The pledget may comprise a soft and/or flexible material such as a fabric. The suture 344 may extend through the internal flexible shaft 336. The pledget 340 may be folded or compressed in a conformation comprising a reduced radial cross section such that it may be disposed within the internal flexible shaft 336 for delivery, as shown in FIGS. 38D and 40A. The pledget 340 may expand to assume a larger radial cross section upon deployment from the distal end of the needle tip 338, as shown in FIG. 38E. In some embodiments, the pledget 340 may be pushed through the internal flexible shaft 336 via a push wire or release wire (not shown), similar to that illustrated in FIG. 35E. Upon delivery through the needle tip 338, proximal retraction of the leaflet suture 344 may cause the leaflet anchor to assume an axially collapsed, radially enlarged conformation which prevents the leaflet anchor from being retracted through the puncture in the leaflet and thereby anchors the leaflet suture 344 to the leaflet, as shown in FIG. 38F.

Figure 43A:
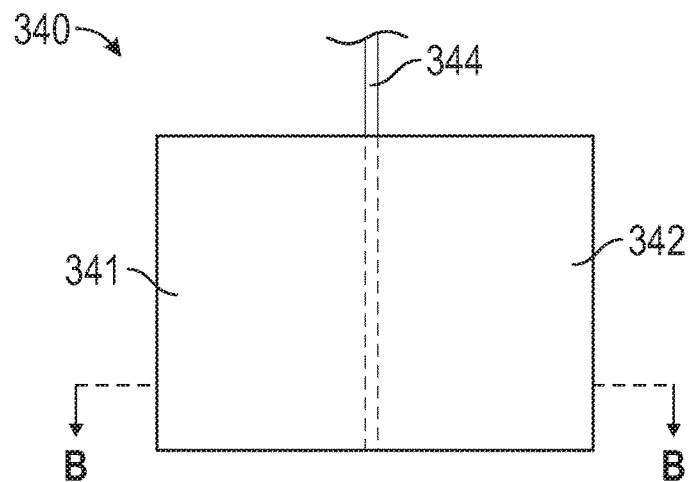
FIG. 43A schematically depicts a pledget formed by integrating a distal end of a suture between two flat sheets of the pledget.
Figure 43B:
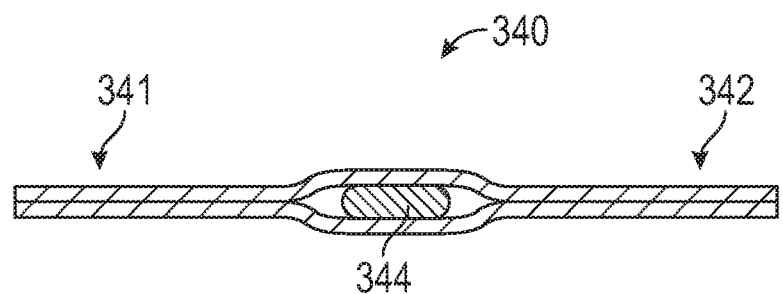
FIG. 43B schematically depicts a cross section of the pledget in FIG. 43A.
Figure 43C:
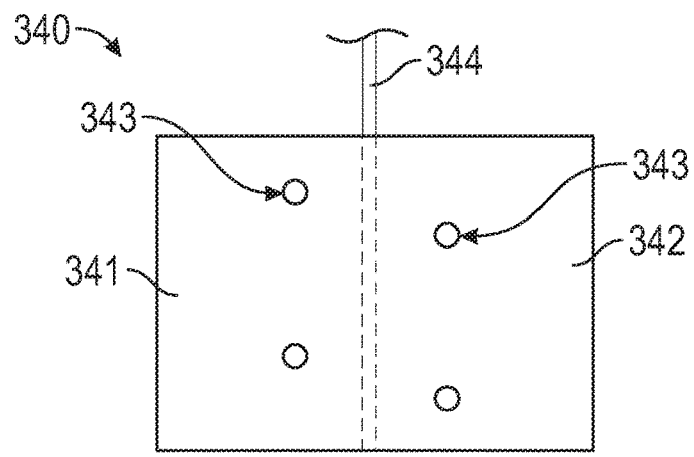
FIG. 43C schematically depicts the pledget in FIG. 43C including apertures through which the suture tail can be threaded back through to form a collapsible anchor.

FIG. 40C schematically depicts a pledget 340 connected to the distal end of a leaflet suture 344. The pledget 340 may comprise two wings 341, 342, which may be rolled/folded (e.g., both in a clockwise or counterclockwise direction) around a longitudinal axis of the pledget 340 to form a reduced cross section conformation. In some embodiments, the leaflet suture 344 may be integrally formed with the pledget 340 as described elsewhere herein (FIGS. 43A-43C). In order to produce a foldable or collapsible configuration, the proximal end of the suture 344 extending from the pledget 340 may be threaded back through one or more apertures (e.g., two apertures, three apertures, four apertures, etc.) formed in the pledget 340, as shown in FIG. 38E. In some embodiments, the apertures may be aligned along a center of the pledget 340. The apertures may extend through the pledget 340 and through the portion of the embedded portion of the suture 344 which is integral with the pledget 340. The embedded portion of the suture 344 may be at least partially flatted within the pledget 340. In some embodiments, the apertures may be place substantially near the center of the pledget (e.g., immediately to the left or right of the embedded suture 344 or alternating between the left and right side of the suture 344). When deployed the suture 344 may be effectively joined to a distal end of the pledget 340 (e.g., the suture 344 may loop back to where it inserts between the pledget sheets). The pledget 340 may be formed such that the wings 341, 342 are approximately the same size or they may be formed to be different sizes. Upon proximal retraction of the leaflet suture 344, the pledget 340 may be folded to assume an accordion-like conformation, as depicted in FIG. 38F. The pledget 340 may assume a conformation comprising a substantially planar surface which is approximately perpendicular to the longitudinal axis of the leaflet suture 344. This conformation may facilitate anchoring the suture 344 in the leaflet. Upon anchoring the leaflet suture 344 in the leaflet, the leaflet anchor delivery subsystem 340 may be withdrawn from the delivery catheter 100. The leaflet anchor delivery components may be proximally retracted over a proximal end of the suture 344, which may remain extending through the delivery catheter 100 to the leaflet anchor 340, alongside the ventricular anchor suture 311.

The ventricular anchor suture 311 and the leaflet anchor suture 344 may be coupled together in a tensioned fashion to form the neo chordae implant or to join two sections of the neo chordae implant together, such that the neo chordae extends between the ventricular anchor 302 and the leaflet anchor 340. The overall length of the neo chordae may be modulated such that an appropriate tension is applied to the leaflet, with the tension maintained by the ventricular anchor 302. The sutures 311, 344 may remain extending through the delivery catheter 100 to a location outside the body. In some embodiments, the proximal ends of the suture 311, 344 may be fed into a handle or proximal portion of a suture lock delivery system 370 during placement of the suture lock and cutting of the sutures 311, 344. In some embodiments, the proximal ends may remain free or coupled or secured by other means.

Figure 41A:
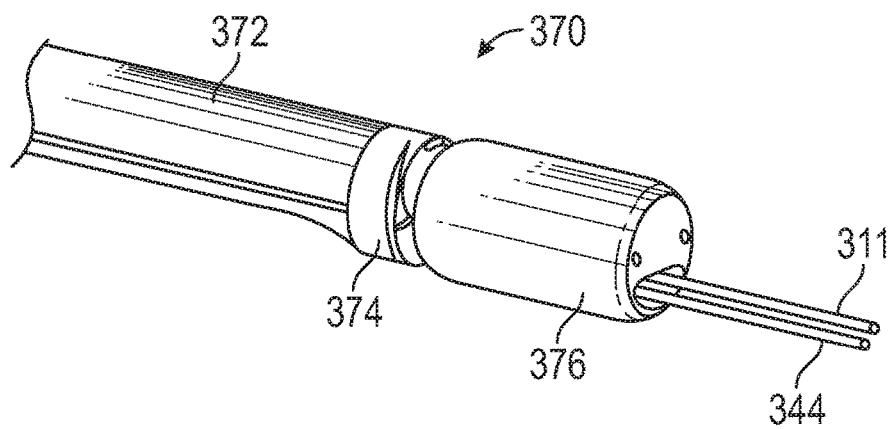
FIG. 41A depicts a perspective view of a distal end of the suture lock delivery subsystem.
Figure 41B:
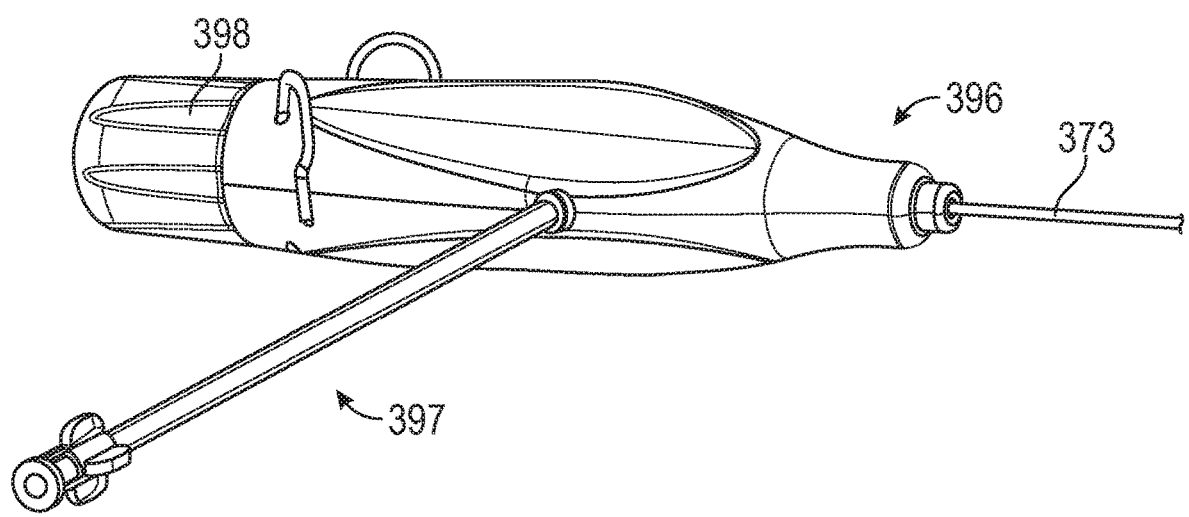
FIG. 41B depicts a perspective view of a proximal end of the suture lock delivery subsystem.
Figure 41C:
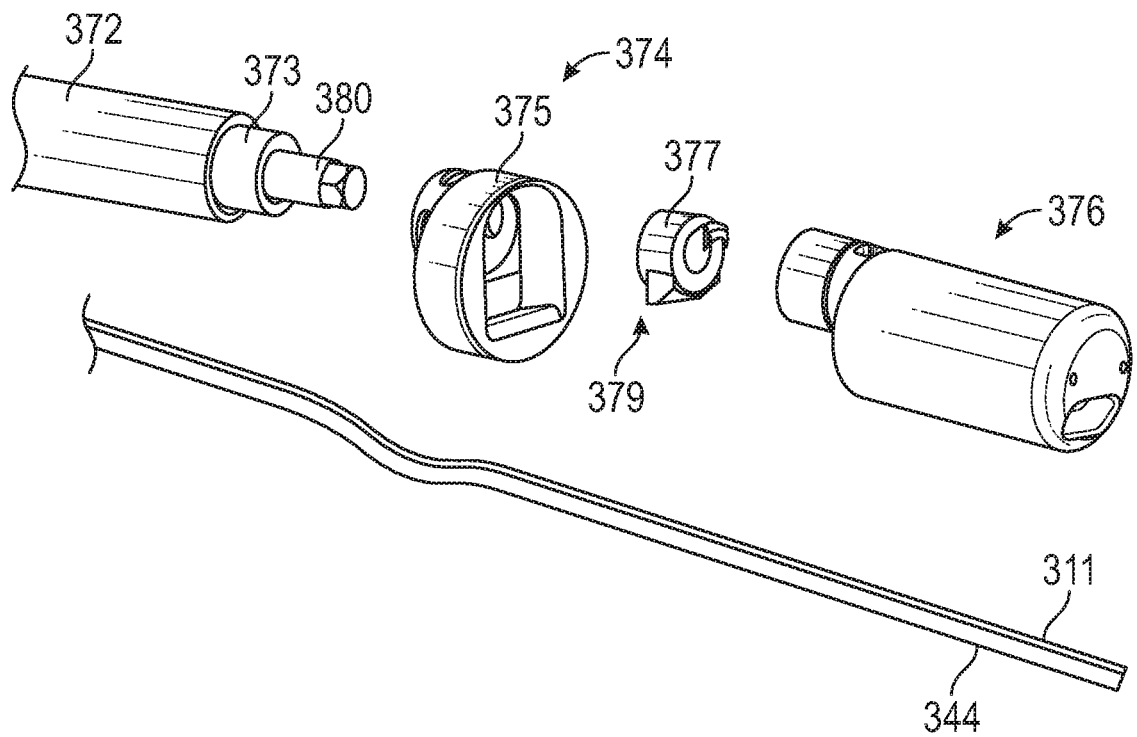
FIG. 41C depicts a partially exploded view of the distal end of the suture lock delivery subsystem.
Figure 41D:
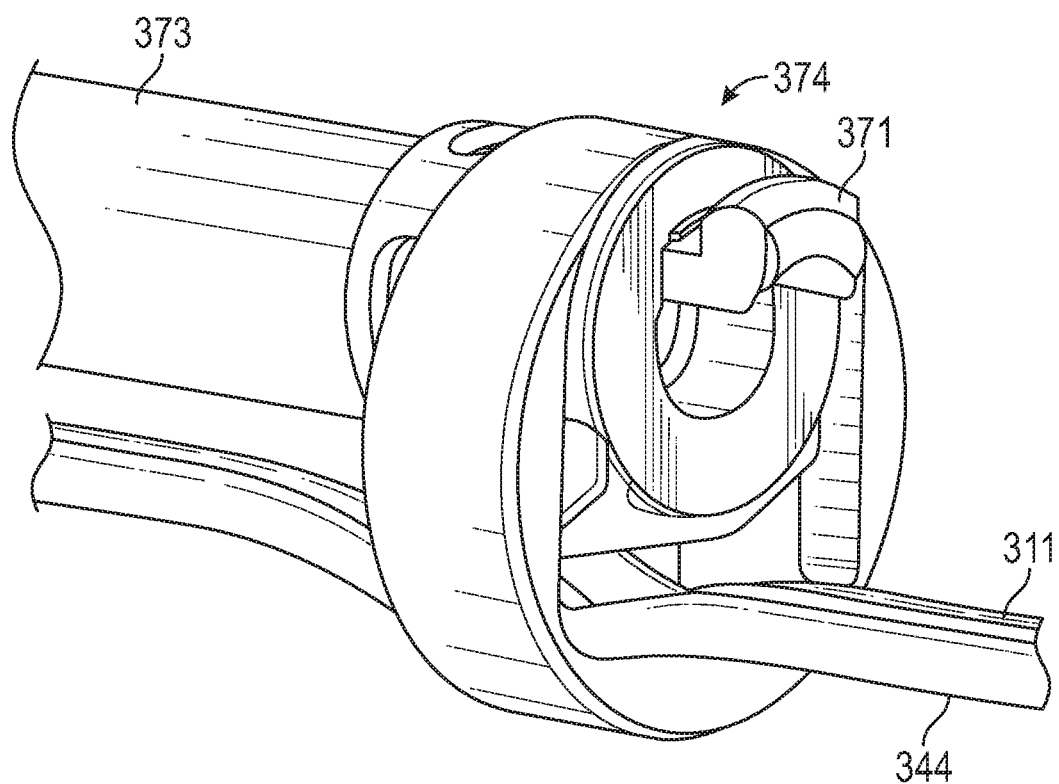
FIG. 41D depicts a perspective view of a distal end of a cutting assembly.
Figure 41E:
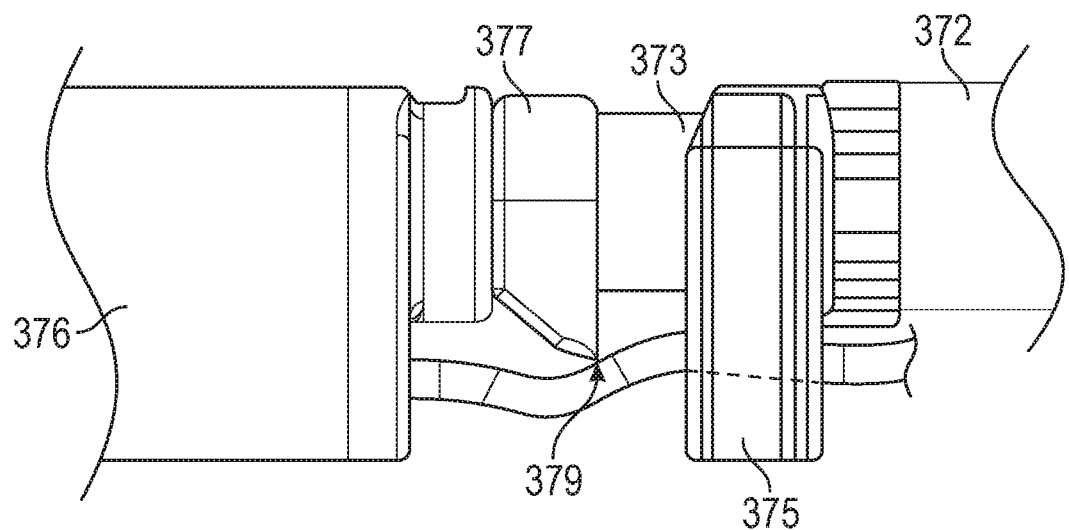
FIG. 41E depicts a side view of a cutting assembly portion of the suture lock delivery subsystem in a configuration where the cutting head is not advanced for holding the sutures prior to being severed.
Figure 41F:
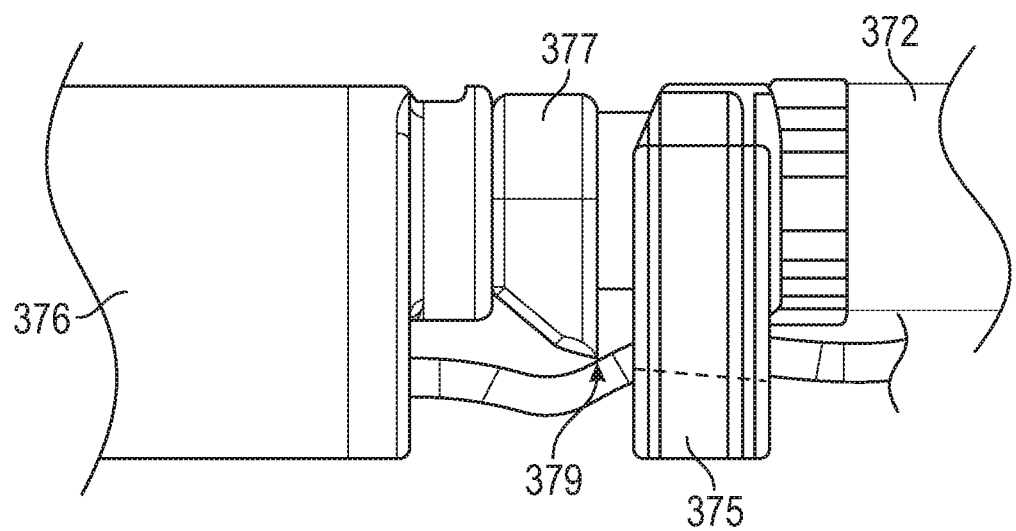
FIG. 41F depicts a side view of a cutting assembly portion of the suture lock delivery subsystem in a configuration where the cutting head is advanced for severing the sutures.
Figure 41G:
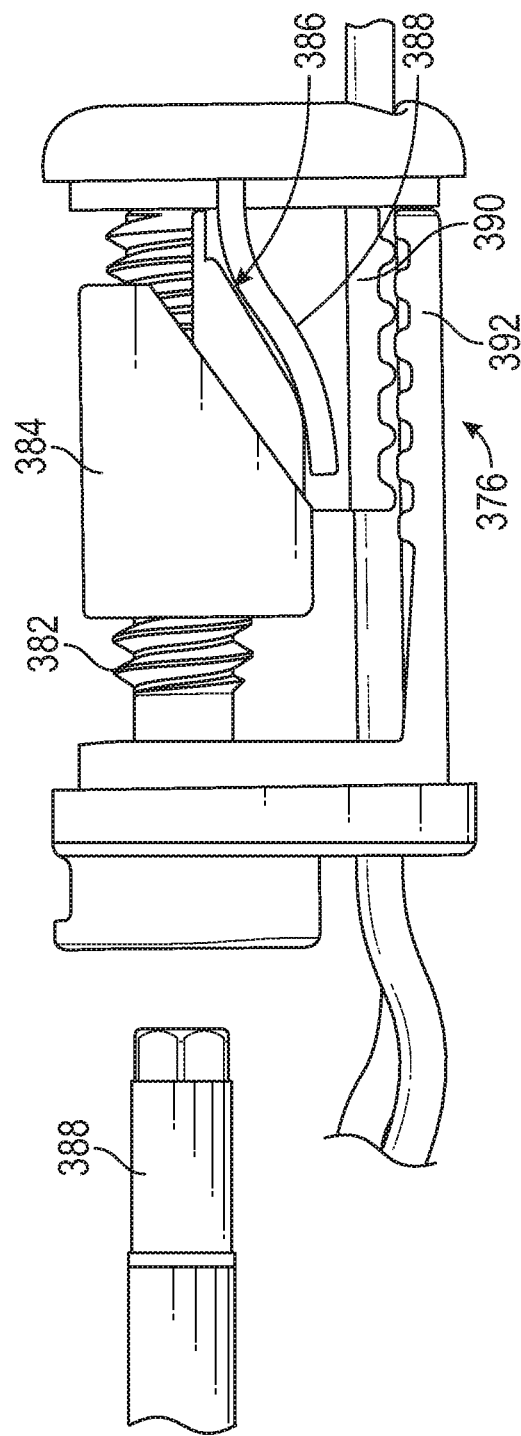
FIG. 41G depicts a side view of a suture lock and a distal end of a torque driver configured to engage the suture lock.
Figure 41H:
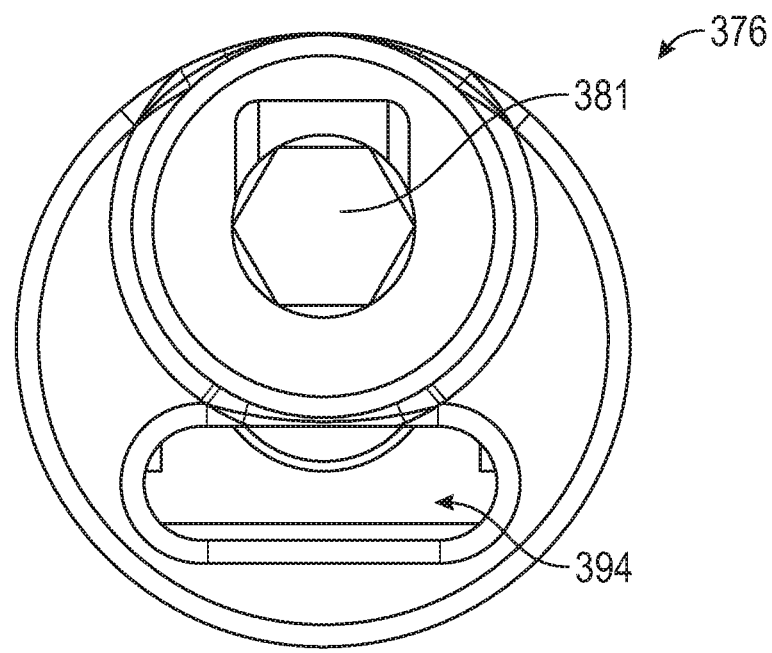
FIG. 41H depicts a proximal end view of the suture lock.
Figure 41I:
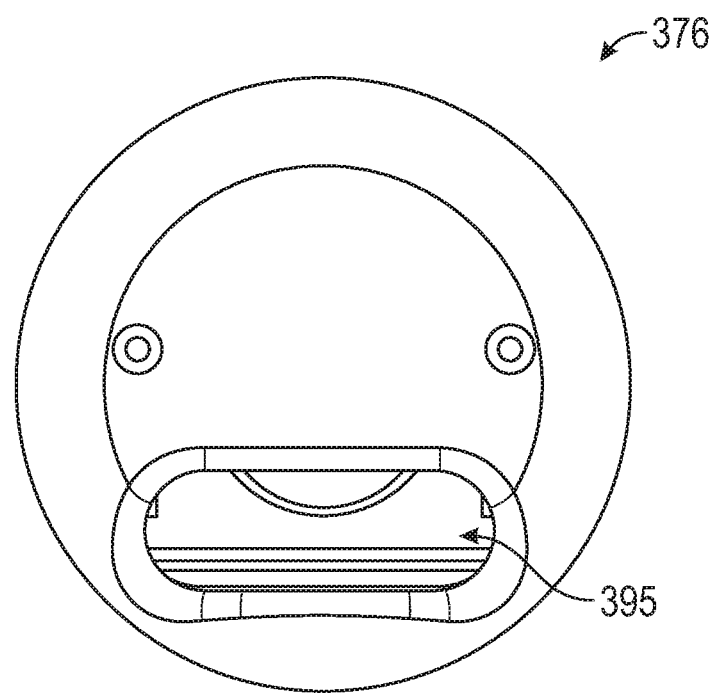
FIG. 41I depicts a distal end view of the suture lock.

FIGS. 41A-41I illustrate various views of the suture lock delivery subsystem 370 and its components. FIG. 41A depicts a perspective view of a distal end of the subsystem 370. FIG. 41B depicts a perspective view of a proximal end of the subsystem 370. FIG. 41C depicts a partially exploded view of the distal end of the subsystem 370. FIG. 41D depicts a perspective view of a distal end of a cutting assembly. FIGS. 41E and 41F depict side views of a cutting assembly portion of the subsystem 370. FIG. 41G depicts a side view of a suture lock 376 and a distal end of a torque driver 388 configured to engage the suture lock 376. FIGS. 41H and 41I depict a proximal end view and a distal end view, respectively, of the suture lock 376.

The suture lock delivery subsystem 370 may be configured to advance (e.g., slide) a suture lock 376 over both the sutures 311, 344 (or even additional sutures) securing them together. The sutures 311, 344 may each be proximally retracted to tension the sutures 311, 344 and modulate the length of each suture 311, 344 between the suture lock 376 and the respective tissue anchors 302, 340. Once the tension and length of the neo chordae implant is optimized, the suture lock 376 may be locked to fix the length of the sutures 311, 344 such that the sutures 311, 344 can no longer move with respect to the suture lock 376. The sutures 311, 344 may then be severed at a point proximal to the suture lock 376. The suture 311, 344 may be cut by the same suture lock delivery subsystem 370 which delivered the suture lock 376. In other embodiments, a separate cutting device may be inserted into the delivery catheter 100 after the suture lock has been locked in place.

Figure 38G:
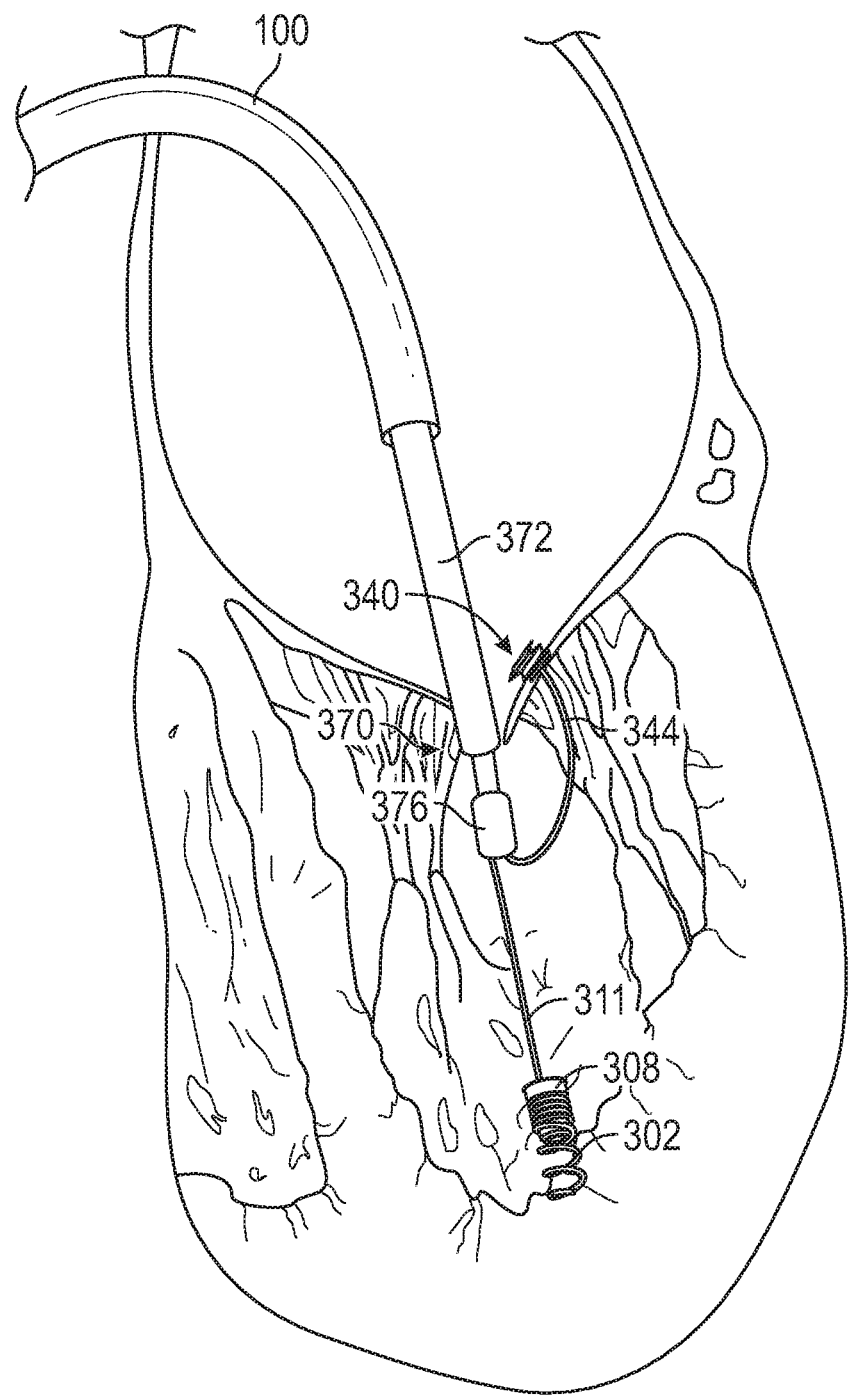
FIG. 38G depicts advancing a suture lock via a suture lock delivery subsystem over the leaflet anchor suture and ventricular anchor suture to connect the leaflet anchor to the ventricular anchor.

FIG. 38G depicts the advancement of suture lock 376 over the ventricular anchor suture 311 and the leaflet suture 344. The suture lock delivery subsystem 370 may be advanced through the delivery catheter 100 and may push a suture lock 376 along the distal direction of the sutures 311, 344, bringing proximal portions of the sutures 311, 344 into close proximity at the distal end of the suture lock 376. The suture lock 376 may be advanced along the sutures by a retainer catheter 373. The distal end of the retainer catheter 373 may be coupled to a retainer element 377 (FIG. 41C). The retainer element may comprise a flange 371 or other mechanical feature configured to engage the suture lock 376. For example, the flange 371 may be inserted into a recess at a proximal end of the suture lock 376. In some embodiments, rotation of the retainer catheter 373 and/or translation substantially perpendicular to the axial direction of the retainer catheter 373 may be used to disengage the retainer catheter 373 from the suture lock 376. The sutures 311, 344 may extend from their respective tissue anchors to pass through the suture lock 376, entering from a distal channel 395 in a distal face of the suture lock 376, shown in FIG. 41I, and exiting at a proximal channel 394 in a proximal face of the suture lock 376, shown in FIG. 41H. The sutures 311, 344 may extend through a channel in a cutter head 375 proximal to the suture lock 376 and along the outside of the retainer catheter 373 and through the delivery catheter 100. The cutter head 375 may be coupled to the distal end of a cutter catheter 372. The retainer catheter 373 may extend through an internal lumen of the cutter catheter 372 such that the two catheters 372, 373 may be extendable or retractable relative to one another.

Once the sutures 311, 344 are locked (fixedly secured) within the suture lock 376, the proximal ends of the suture 311, 344 may be cut adjacent to the proximal face of the suture lock. The sutures 311, 344 may be cut by advancing the cutter catheter 372 coupled to the cutter head 375 toward the proximal face of the suture lock 376. As schematically illustrated in FIGS. 41E-41F, as the cutter head 375 advances along the retainer catheter 373 toward the retainer element 377, the cutter head brings the sutures 311, 344 into close proximity to a cutting blade 379 positioned on the retainer element 377. The cutter head 375 is configured to advance over the retainer element 377 in such a fashion that the channel in the cutter head 375 retaining the sutures 311, 344 becomes increasingly spatially occupied by the blade 379. As the blade 379 is forced into the channel of the cutter head 375, the blade 379 shears the sutures 311, 344. Application of proximal tension to the sutures 311, 344 may facilitate the cutting of the sutures 311, 344. In other embodiments, different actuations (e.g., rotation of a cutting catheter) can be configured to sever the sutures 311, 344. In some implementations, more than two sutures may be employed and may be locked within the suture lock 376 and severed by the suture lock delivery subsystem 370 in the same fashion. In some embodiments, advancement of the cutter head 375 over the retainer element 377 may facilitate the disengagement of the retainer catheter 373 from the suture lock 376. For example, the cutter head 375 may advance to a distal position where it is configured to stabilize the suture lock 376, allowing the retainer catheter 373 to be axially and/or rotationally disengaged from the suture lock 376.

FIG. 41G illustrates a side view of an example of a suture lock 376 (shown with its outer casing/shell removed). The sutures may pass through the suture lock 376 from a distal end to a proximal end as described elsewhere herein. The suture lock 376 may comprise a screw 382 configured to distally advance or proximally retract a push wedge 384, depending on the direction of rotation of the screw. The screw 382 may be rotated by a torque shaft 388. The torque shaft 388 may comprise a driver head configured to mate with recess 381 (e.g., a polygonal recess or other non-circular shaped recess, as shown in FIG. 41H) positioned at the proximal end of the suture lock 376 such that rotation of the torque shaft 388 causes rotation of the screw 382. The torque shaft 388 may extend through an internal lumen of the retainer catheter 373. The torque shaft 388 may be rotated at its proximal end by a knob 398 or other actuation mechanism positioned at a proximal end of the subsystem handle 396. The handle 396 may include a hemostasis valve 397. In some implementations, the sutures 311, 344 may pass through the hemostasis valve 397.

Advancement of the push wedge 384 by the torque shaft 388 may cause a ramp or angled surface 386 to gradually compress one or more springs, such as spring pins 388. Compression of the one or more springs 388 may force a clamp 390 downward on the sutures 311, 344, compressing the sutures 311, 344 between two opposing surfaces. In some embodiments, the clamp 390 and the opposing surface 392 may have notched surfaces configured to mate with each other at discrete increments. The mated notched surfaces may provide enhanced retention of the sutures 311, 344 between the opposing surfaces such that they cannot be withdrawn, either proximally or distally, from the suture lock 376. In some embodiments, the tightening may be reversible by rotating the torque shaft in an opposite direction.

Figure 38H:
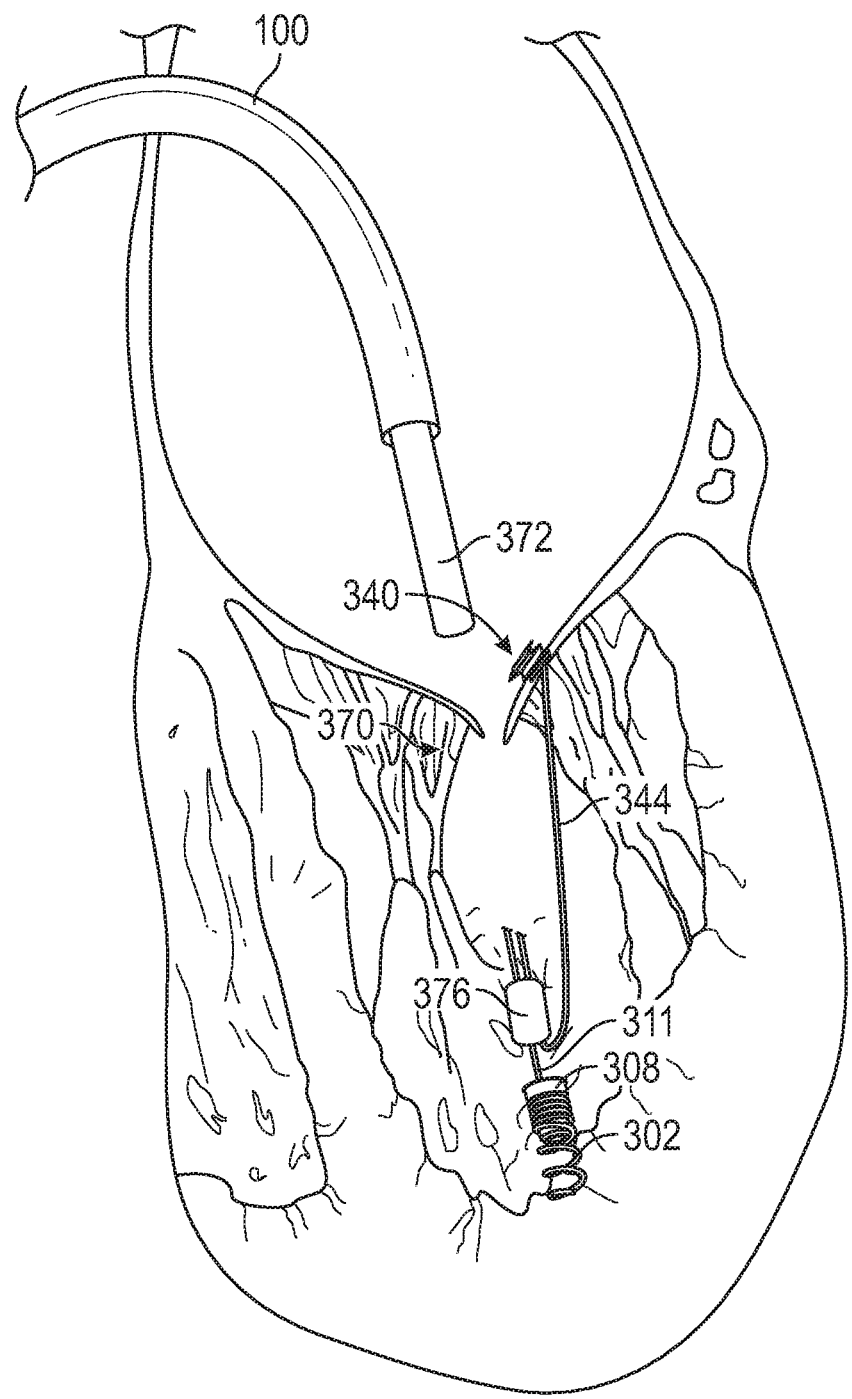
FIG. 38H depicts the suture lock in locked position after the tension has been adjusted with the suture tails having been severed.

Once the suture lock is properly positioned over the sutures 311, 344 and locked into place, the sutures 311, 344 may be severed as described elsewhere herein. FIG. 38H depicts the retraction of the suture lock delivery subsystem 370 after the sutures 311, 344 have been cut. Once the suture lock delivery subsystem 370 has been removed from the delivery catheter 100, the delivery catheter 100 may be withdrawn from the body.

Figure 42:
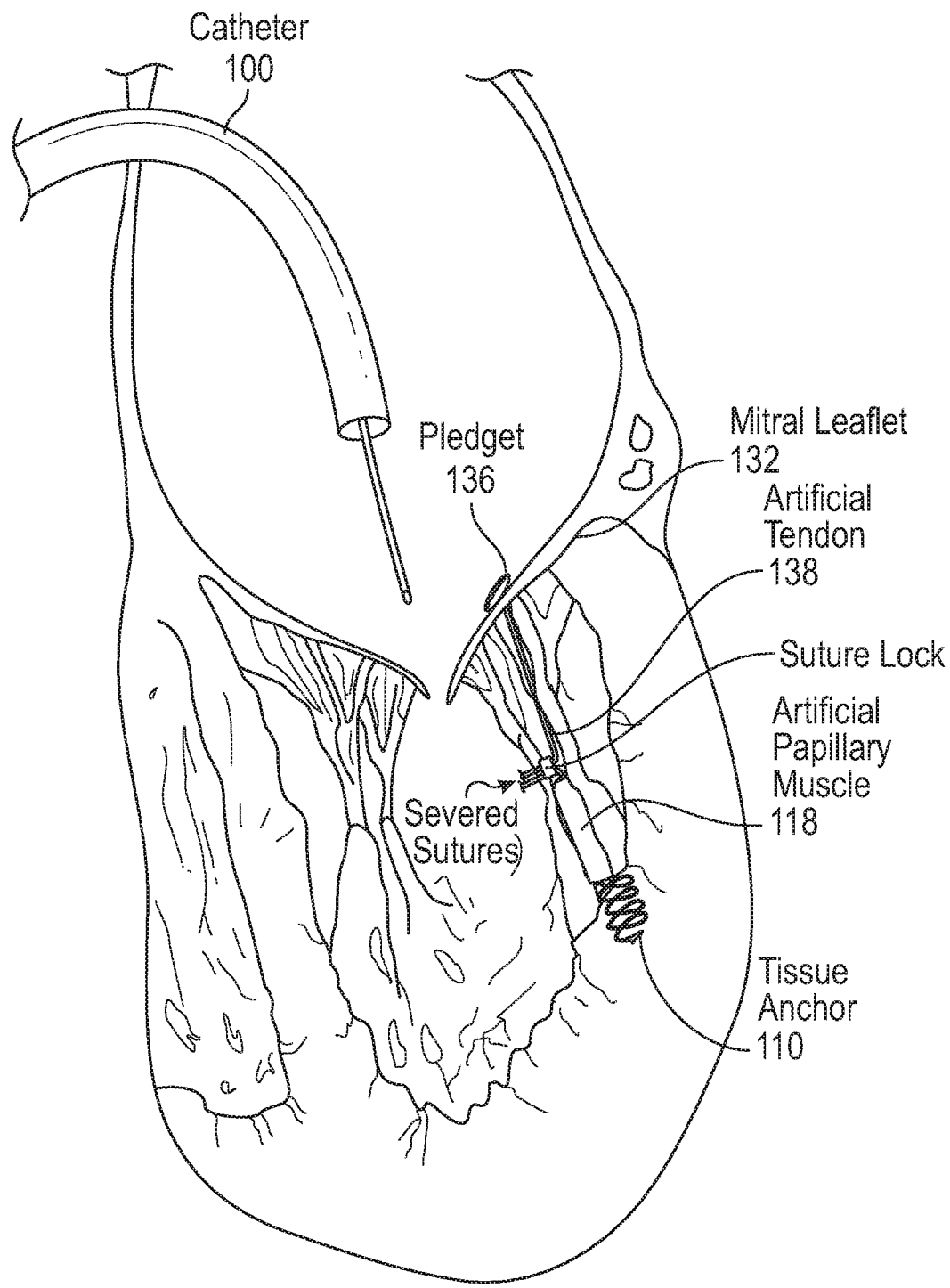
FIG. 42 schematically illustrates a neo chordae construct implanted between two papillary muscles such that the neo chordae construct can be aligned substantially parallel to the native chordae.

FIG. 42 schematically illustrates a helical anchor 110 implanted in a portion of the ventricle comprising relatively thick tissue, between two of the papillary muscles. As described elsewhere herein, the implanted neo chord construct, the optional neo papillary muscle, and/or the helical anchor may be aligned along a longitudinal axis substantially parallel to or concentric with the original path of the native chord and/or the path of the surrounding native chordae. In certain embodiments, the implanted neo chord construct, the optional neo papillary muscle, and/or the helical anchor aligned along a longitudinal axis that is within 5 degrees, 10 degrees, or 15 degrees of being parallel with the original path of the native chord and/or the path of the surrounding native chorda.

FIGS. 43A-43C schematically depict an example of a pledget as described elsewhere herein, in particular with reference to FIGS. 38E and 38F. FIG. 43A schematically depicts a pledget 340 formed by affixing a distal end (shown in dashed lines) of the suture 344 between two flat sheets, such that the sheets for left and right wings 341, 342. FIG. 43B shows a cross-section of the pledget 340 along the axis of B-B illustrated in FIG. 43A. In some embodiments, the suture 344 may be inserted between two sheets (e.g., substantially down the middle of the sheets) and pressed and/or laminated to join the three components together (e.g., under heat and/or pressure). At least one of the layers may be partially sintered. The suture 344 may be flattened and/or densified to improve resistance to suture tear out. The sheets may be flat polytetrafluoroethylene (PTFE) sheets (e.g., thin uncured expanded PTFE (ePTFE) sheets) or any other suitable material. In some implementations, the leaflet suture 344 may be disposed between the sheets in alternative configurations, such as a zig-zag or s-shaped configuration. FIG. 43C shows the pledget 340 of FIG. 43A comprising a plurality of apertures 343 through which the proximal tail end of the suture 344 may be threaded through. In some embodiments, one or more apertures 343 may be formed through the pledget, in various configurations, to form a collapsible structure, as described elsewhere herein, which is configured to anchor the suture 344 against the mitral leaflet. FIG. 43C shows apertures 343 alternating around opposing sides of the suture 344. In some embodiments, the apertures 343 may be formed on the same side of the suture 344 (e.g., in wing 341 or wing 342). In some embodiments, the apertures 343 may be formed through the suture 344. The apertures 343 may be aligned along a center of the pledget 340. The apertures 343 may be aligned along the length of the suture 344 (e.g., may form a straight line). The suture 344 may be at least partially flattened between the two opposing sheets, which may facilitate the placement of apertures 343 through the suture 344. Various combinations of apertures 343, including the positioning described above, may be used.

Although this disclosure describes certain embodiments and examples, many aspects of the above-described systems and methods may be combined differently and/or modified to form still further embodiments or acceptable examples. All such modifications and variations are intended to be included herein within the scope of this disclosure. Indeed, a wide variety of designs and approaches are possible and are within the scope of this disclosure.

Also, although there may be some embodiments within the scope of this disclosure that are not expressly recited above or elsewhere herein, this disclosure contemplates and includes all embodiments within the scope of what this disclosure shows and describes. Further, this disclosure contemplates and includes embodiments comprising any combination of any structure, material, step, or other feature disclosed anywhere herein with any other structure, material, step, or other feature disclosed anywhere herein.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

For purposes of this disclosure, certain aspects, advantages, and features are described herein. Not necessarily all such aspects, advantages, and features may be achieved in accordance with any particular embodiment. Those skilled in the art will recognize that the disclosure may be embodied or carried out in a manner that achieves one advantage or a group of advantages as taught herein without necessarily achieving other advantages as may be taught or suggested herein.

The disclosure herein of any particular feature, aspect, method, property, characteristic, quality, attribute, element, or the like in connection with various embodiments can be used in all other embodiments set forth herein. Also, any methods described herein may be practiced using any device suitable for performing the recited steps.

Moreover, while components and operations may be depicted in the drawings or described in the specification in a particular arrangement or order, such components and operations need not be arranged and performed in the particular arrangement and order shown, nor in sequential order, nor include all of the components and operations, to achieve desirable results. Other components and operations that are not depicted or described can be incorporated in the embodiments and examples. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

In summary, various illustrative embodiments and examples are described herein. Although the systems and methods have been disclosed in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow as well as their full scope of equivalents.

What is claimed is:

1. A neo chordae tendinae deployment system, comprising:
    a catheter having a proximal end and a distal end;
    a helical anchor within the catheter, having a driver configured to rotate the helical anchor extending proximally through the catheter; and
    a radially enlargeable leaflet anchor within the catheter having a suture extending proximally through the catheter;
    wherein the radially enlargeable leaflet anchor comprises the suture disposed between two sheets of material.

2. A neo chordae tendinae deployment system as in claim 1, wherein the radially enlargeable leaflet anchor comprises a pledget.

3. A neo chordae tendinae deployment system as in claim 2, wherein the pledget is transformable from an elongate strip configuration to a radially enlarged, axially shortened configuration by proximal retraction of the suture.

4. A neo chordae tendinae deployment system as in claim 1, wherein the radially enlargeable leaflet anchor is carried within a deflectable deployment tube carried within the catheter.

5. A neo chordae tendinae deployment system as in claim 4, wherein a distal deflection zone of the deployment tube is deflectable through an angle of at least about 160 degrees in response to manipulation of a proximal deflection control.

6. A neo chordae tendinae deployment system as in claim 5, wherein the distal deflection zone is within about 1.5 cm from a distal end of the deployment tube.

7. A neo chordae tendinae deployment system as in claim 5, wherein the distal deflection zone is deflectable to form a curve having a best fit radius of no more than about 1.5 cm.

8. A neo chordae tendinae deployment system as in claim 5, wherein the deflectable deployment tube comprises a slotted deflection tube.

9. A neo chordae tendinae deployment system as in claim 1, configured to deploy the helical anchor in a distal direction, and configured to deploy the radially enlargeable anchor in a proximal direction.

10. A neo chordae tendinae deployment system as in claim 1, wherein the enlargeable leaflet anchor can be sequentially inserted into the catheter after the helical anchor and driver have been removed from the catheter.

11. A neo chordae tendinae deployment system as in claim 1, wherein the enlargeable leaflet anchor and the helical anchor and driver can be preloaded within the catheter.

12. A pledget for anchoring to a heart leaflet, the pledget comprising:
    two flat sheets comprising substantially overlapping areas;
    a suture positioned between the two flat sheets, the suture having a proximal end and a distal end, wherein the proximal end extends from a first side of the two flat sheets; and
    one or more apertures extending through the two flat sheets, being sized to receive the suture;
    wherein the two flat sheets are joined together over portions of the overlapping areas on both sides of the suture.

13. The pledget of claim 12, wherein the suture is at least partially flattened between the two sheets.

14. The pledget of claim 13, wherein the one or more apertures extend through the flattened suture.

15. The pledget of claim 12, wherein the distal end of the suture extends to a second side of the two flat sheets, the second side being opposite the first side.

16. The pledget of claim 12, wherein the suture extends between the two flat sheets along a substantially straight line.

17. The pledget of claim 12, wherein the suture extends between the two flat sheets along a zig-zag or undulating direction.

18. The pledget of claim 12, wherein the two flat sheets comprise expanded polytetrafluoroethylene.

19. The pledget of claim 12, wherein at least one of the two flat sheets is at least partially sintered.

20. The pledget of claim 12, wherein a proximal end of the suture extending from the first side of the two flat sheets is threaded through the one or more apertures.

21. The pledget of claim 20, wherein the pledget comprises a collapsed configuration in which the two flat sheets are folded over at least once to form a radially enlarged cross section extending around the suture as it passes through the one or more apertures.

22. A neo chordae tendinae deployment system, comprising:
a catheter having a proximal end and a distal end;
a helical anchor within the catheter, having a driver configured to rotate the helical anchor extending proximally through the catheter; and
a radially enlargeable leaflet anchor within the catheter having a suture extending proximally through the catheter;
wherein the radially enlargeable leaflet anchor is carried within a deflectable deployment tube carried within the catheter,
wherein a distal deflection zone of the deployment tube is deflectable through an angle of at least about 160 degrees in response to manipulation of a proximal deflection control, and
wherein the radially enlargeable leaflet anchor comprises the suture disposed between two sheets of material.

23. A neo chordae tendinae deployment system as in claim 22, wherein the radially enlargeable leaflet anchor is transformable from an elongate strip configuration to a radially enlarged, axially shortened configuration by proximal retraction of the suture.

24. A neo chordae tendinae deployment system as in claim 22, wherein the distal deflection zone is deflectable to form a curve having a best fit radius of no more than about 1.5 cm.

25. A neo chordae tendinae deployment system as in claim 22, wherein the enlargeable leaflet anchor can be sequentially inserted into the catheter after the helical anchor and driver have been removed from the catheter.

26. A neo chordae tendinae deployment system as in claim 22, wherein the enlargeable leaflet anchor and the helical anchor and driver can be preloaded within the catheter.

27. A neo chordae tendinae deployment system, comprising:
a catheter having a proximal end and a distal end;
a helical anchor within the catheter, having a driver configured to rotate the helical anchor extending proximally through the catheter; and
a radially enlargeable leaflet anchor within the catheter having a suture extending proximally through the catheter;
wherein the system is configured to deploy the helical anchor in a distal direction, and configured to deploy the radially enlargeable anchor in a proximal direction.

28. A neo chordae tendinae deployment system as in claim 27, wherein the radially enlargeable leaflet anchor comprises a pledget.

29. A neo chordae tendinae deployment system as in claim 28, wherein the pledget is transformable from an elongate strip configuration to a radially enlarged, axially shortened configuration by proximal retraction of the suture.

30. A neo chordae tendinae deployment system as in claim 27, wherein the radially enlargeable leaflet anchor comprises the suture inserted disposed between two sheets of material.

31. A neo chordae tendinae deployment system as in claim 27, wherein the radially enlargeable leaflet anchor is carried within a deflectable deployment tube carried within the catheter.

32. A neo chordae tendinae deployment system as in claim 31, wherein a distal deflection zone of the deployment tube is deflectable through an angle of at least about 160 degrees in response to manipulation of a proximal deflection control.

33. A neo chordae tendinae deployment system as in claim 32, wherein the distal deflection zone is within about 1.5 cm from a distal end of the deployment tube.

34. A neo chordae tendinae deployment system as in claim 32, wherein the distal deflection zone is deflectable to form a curve having a best fit radius of no more than about 1.5 cm.

35. A neo chordae tendinae deployment system as in claim 27, wherein the enlargeable leaflet anchor can be sequentially inserted into the catheter after the helical anchor and driver have been removed from the catheter.

36. A neo chordae tendinae deployment system as in claim 27, wherein the enlargeable leaflet anchor and the helical anchor and driver can be preloaded within the catheter.

37. A neo chordae tendinae deployment system, comprising:
a catheter having a proximal end and a distal end;
a helical anchor within the catheter, having a driver configured to rotate the helical anchor extending proximally through the catheter; and
a radially enlargeable leaflet anchor within the catheter having a suture extending proximally through the catheter;
wherein the radially enlargeable leaflet anchor is carried within a deflectable deployment tube carried within the catheter,
wherein a distal deflection zone of the deployment tube is deflectable through an angle of at least about 160 degrees in response to manipulation of a proximal deflection control, and
wherein the deflectable deployment tube comprises a slotted deflection tube.

38. A neo chordae tendinae deployment system as in claim 37, wherein the radially enlargeable leaflet anchor comprises a pledget.

39. A neo chordae tendinae deployment system as in claim 38, wherein the pledget is transformable from an elongate strip configuration to a radially enlarged, axially shortened configuration by proximal retraction of the suture.

40. A neo chordae tendinae deployment system as in claim 37, wherein the distal deflection zone is deflectable to form a curve having a best fit radius of no more than about 1.5 cm.

41. A neo chordae tendinae deployment system as in claim 37, wherein the enlargeable leaflet anchor can be sequentially inserted into the catheter after the helical anchor and driver have been removed from the catheter.

42. A neo chordae tendinae deployment system as in claim 37, wherein the enlargeable leaflet anchor and the helical anchor and driver can be preloaded within the catheter.

\* \* \* \* \*

UNITED STATES PATENT AND TRADEMARK OFFICE
CERTIFICATE OF CORRECTION

PATENT NO. : 10,925,731 B2
APPLICATION NO. : 15/858671
DATED : February 23, 2021
INVENTOR(S) : Gordon B. Bishop et al.

It is certified that error appears in the above-identified patent and that said Letters Patent is hereby corrected as shown below:

On the Title Page

Page 3, Column 2, item (56), Lines 12-13, delete "III-30-III-34." and insert --III-30-34.--.

In the Specification

Column 41, Lines 25-26, delete "sub combination" and insert --subscombination--.

In the Claims

Column 44, Line 14, Claim 30, after "suture" delete "inserted".

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*